US010835549B2

(12) United States Patent
Duvall et al.

(10) Patent No.: US 10,835,549 B2
(45) Date of Patent: Nov. 17, 2020

(54) POLYPLEXES

(71) Applicants: Vanderbilt University, Nashville, TN (US); The United States as represented by the Department of Veterans Affairs, Washington, DC (US)

(72) Inventors: Craig Duvall, Nashville, TN (US); Brian Connor Evans, Bartlett, TN (US); Colleen Brophy, Nashville, TN (US); Kyle Hocking, Alpharetta, GA (US)

(73) Assignees: Vanderbilt University, Nashville, TN (US); The United States as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/784,017

(22) PCT Filed: Apr. 11, 2014

(86) PCT No.: PCT/US2014/033873
§ 371 (c)(1),
(2) Date: Oct. 12, 2015

(87) PCT Pub. No.: WO2014/169256
PCT Pub. Date: Oct. 16, 2014

(65) Prior Publication Data
US 2016/0058876 A1    Mar. 3, 2016

Related U.S. Application Data

(60) Provisional application No. 61/811,078, filed on Apr. 11, 2013.

(51) Int. Cl.
| | |
|---|---|
| *A61K 31/7105* | (2006.01) |
| *A61K 47/32* | (2006.01) |
| *A61K 9/00* | (2006.01) |
| *A61K 38/55* | (2006.01) |
| *A61K 47/69* | (2017.01) |
| *A61K 47/58* | (2017.01) |
| *A61K 31/711* | (2006.01) |
| *A61K 38/00* | (2006.01) |
| *A61L 27/26* | (2006.01) |
| *A61L 27/54* | (2006.01) |

(52) U.S. Cl.
CPC ........ *A61K 31/7105* (2013.01); *A61K 9/0019* (2013.01); *A61K 31/711* (2013.01); *A61K 38/005* (2013.01); *A61K 38/55* (2013.01); *A61K 47/32* (2013.01); *A61K 47/58* (2017.08); *A61K 47/6927* (2017.08); *A61L 27/26* (2013.01); *A61L 27/54* (2013.01); *A61L 2300/252* (2013.01)

(58) Field of Classification Search
None
See application file for complete search history.

(56) References Cited

U.S. PATENT DOCUMENTS

| | | | | |
|---|---|---|---|---|
| 2003/0203865 | A1* | 10/2003 | Harvie | A61K 9/1272 514/44 R |
| 2004/0176282 | A1* | 9/2004 | Dalby | C12N 15/90 514/44 R |
| 2010/0150952 | A1* | 6/2010 | Stayton | A61K 39/0011 424/193.1 |
| 2010/0158968 | A1* | 6/2010 | Panitch | A61K 38/04 424/422 |
| 2011/0288036 | A1 | 11/2011 | Lander et al. | |
| 2013/0183379 | A1 | 7/2013 | Devore | |

FOREIGN PATENT DOCUMENTS

| | | |
|---|---|---|
| EP | 2284210 A1 | 2/2011 |
| EP | 2138575 B1 | 6/2013 |
| WO | WO2007001448 A2 | 1/2007 |
| WO | WO2009021137 A2 | 2/2009 |
| WO | WO2014144842 | 9/2014 |

OTHER PUBLICATIONS

As van de Wetering, P. et al, 2-(dimethylamino)ethyl methacrylate based (co)polymers as gene transfer agents, Journal of Controlled Release 53 (1998) 145-153.*
Muto et al. 'Inhibition of Mitogen Activated Protein Kinase Activated Protein Kinase II with MMI-0100 reduces intimal hyperplasia ex vivo and in vivo,' Vascular Pharmacology, Jan. 1, 2012 (Jan. 1, 2012)., vol. 56, pp. 47-55.
Go, A.S. et al. Heart disease and stroke statistics—2013 update: a report from the American Heart Association. Circulation 127, e6-e245 (2013).
Alexander, J.H. et al. Efficacy and safety of edifoligide, an E2F transcription factor decoy, for prevention of vein graft failure following coronary artery bypass graft surgery: PREVENT IV: a randomized controlled trial. JAMA 294, 2446-2454 (2005).
Saunders, P.C. et al. Vein graft arterialization causes differential activation of mitogen-activated protein kinases. J Thorac Cardiovasc Surg 127, 1276-1284 (2004).

(Continued)

*Primary Examiner* — Thomas S Heard
(74) *Attorney, Agent, or Firm* — Stites & Harbison PLLC; Sean P. Ritchie

(57) ABSTRACT

The present disclosure relates to compounds comprising (i) an active agent, wherein the active agent includes a charge at a predetermined pH, (ii) a polymer, wherein the polymer includes an opposite charge than the active agent at the predetermined pH; and (iii) a polyplex comprising the peptide and the polymer electrostatically bond together at the predetermined pH. In some embodiments, the active agent is a peptide, such as a peptide comprising MAPKAP kinase II inhibitory peptide, and in some embodiments the peptide includes a cell-penetrating peptide. In further embodiments, the disclosure provides methods for treating a disease or condition by administering a composition according to the present disclosure to a subject in need thereof.

6 Claims, 39 Drawing Sheets

Specification includes a Sequence Listing.

(56) References Cited

OTHER PUBLICATIONS

Raingeaud, J. et al. Pro-inflammatory cytokines and environmental stress cause p38 mitogen-activated protein kinase activation by dual phosphorylation on tyrosine and threonine. J Biol Chem 270, 7420-7426 (1995).
Zarubin, T. & Han, J. Activation and signaling of the p38 MAP kinase pathway. Cell Res 15, 11-18 (2005).
Engel, K., Kotlyarov, A. & Gaestel, M. Leptomycin B-sensitive nuclear export of MAPKAP kinase 2 is regulated by phosphorylation. EMBO J 17, 3363-3371 (1998).
Xu, J.J., Hendriks, B.S., Zhao, J. & de Graaf, D. Multiple effects of acetaminophen and p38 inhibitors: towards pathway toxicology. FEBS Lett 582, 1276-1282 (2008).
Dambach, D.M. Potential adverse effects associated with inhibition of p38alpha/beta MAP kinases. Curr Top Med Chem 5, 929-939 (2005).
Ward, B., Seal, B.L., Brophy, C.M. & Panitch, A. Design of a bioactive cell-penetrating peptide: when a transduction domain does more than transduce. Journal of Peptide Science 15, 668-674 (2009).
Hayess, K. & Benndorf, R. Effect of protein kinase inhibitors on activity of mammalian small heat-shock protein (HSP25) kinase. Biochem Pharmacol 53, 1239-1247 (1997).
Lopes, L.B. et al. A novel cell permeant peptide inhibitor of MAPKAP kinase II inhibits intimal hyperplasia in a human saphenous vein organ culture model. J Vasc Surg 52, 1596-1607 (2010).
Flynn, C.R. et al. Internalization and intracellular trafficking of a PTD-conjugated anti-fibrotic peptide, AZX100, in human dermal keloid fibroblasts. J Pharm Sci 99, 3100-3121 (2010).
Jones, R.A. et al. Poly(2-alkylacrylic acid) polymers deliver molecules to the cytosol by pH-sensitive disruption of endosomal vesicles. Biochem J 372, 65-75 (2003).
Lackey, C.A., Press, O.W., Hoffman, A.S. & Stayton, P.S. A biomimetic pH-responsive polymer directs endosomal release and intracellular delivery of an endocytosed antibody complex. Bioconjugate Chemistry 13, 996-1001 (2002).
Murthy, N., Robichaud, J.R., Tirrell, D.A., Stayton, P.S. & Hoffman, A.S. The design and synthesis of polymers for eukaryotic membrane disruption. J Control Release 61, 137-143 (1999).
Foster, S., Duvall, C.L., Crownover, E.F., Hoffman, A.S. & Stayton, P.S. Intracellular delivery of a protein antigen with an endosomal-releasing polymer enhances CD8 T-cell production and prophylactic vaccine efficacy. Bioconjug Chem 21, 2205-2212 (2010).
Crownover, E., Duvall, C.L., Convertine, A., Hoffman, A.S. & Stayton, P.S. RAFT-synthesized graft copolymers that enhance pH-dependent membrane destabilization and protein circulation times. J Control Release 155, 167-174 (2011).
Sorkin, A. & Von Zastrow, M. Signal transduction and endocytosis: close encounters of many kinds. Nat Rev Mol Cell Biol 3, 600-614 (2002).
Evans, B.C. et al. Ex vivo red blood cell hemolysis assay for the evaluation of pH-responsive endosomolytic agents for cytosolic delivery of biomacromolecular drugs. J Vis Exp, e50166 (2013).
Humphries, W.H.t. & Payne, C.K. Imaging lysosomal enzyme activity in live cells using self-quenched substrates. Anal Biochem 424, 178-183 (2012).
Rousseau, S. et al. Inhibition of SAPK2a/p38 prevents hnRNP A0 phosphorylation by MAPKAP-K2 and its interaction with cytokine mRNAs. EMBO J 21, 6505-6514 (2002).
Hitti, E. et al. Mitogen-activated protein kinase-activated protein kinase 2 regulates tumor necrosis factor mRNA stability and translation mainly by altering tristetraprolin expression, stability, and binding to adenine/uridine-rich element. Mol Cell Biol 26, 2399-2407 (2006).
Ronkina, N. et al. MAPKAP kinases MK2 and MK3 in inflammation: complex regulation of TNF biosynthesis via expression and phosphorylation of tristetraprolin. Biochem Pharmacol 80, 1915-1920 (2010).
Chen, H.F., Xie, L.D. & Xu, C.S. Role of heat shock protein 27 phosphorylation in migration of vascular smooth muscle cells. Mol Cell Biochem 327, 1-6 (2009).
Schleimer, K. et al. Training a sophisticated microsurgical technique: interposition of external jugular vein graft in the common carotid artery in rats. J Vis Exp (2012).
Mueller, L. et al. TNF-alpha similarly induces IL-6 and MCP-1 in fibroblasts from colorectal liver metastases and normal liver fibroblasts. Biochem Biophys Res Commun 397, 586-591 (2010).
Mitchell, R.N. & Libby, P. Vascular remodeling in transplant vasculopathy. Circ Res 100, 967-978 (2007).
Stark, V.K., Hoch, J.R., Warner, T.F. & Hullett, D.A. Monocyte chemotactic protein-1 expression is associated with the development of vein graft intimal hyperplasia. Arterioscl Throm Vas 17, 1614-1621 (1997).
Walensky, L.D. et al. Activation of apoptosis in vivo by a hydrocarbon-stapled BH3 helix. Science 305, 1466-1470 (2004).
Heitz, F., Morris, M.C. & Divita, G. Twenty years of cell-penetrating peptides: from molecular mechanisms to therapeutics. British Journal of Pharmacology 157, 195-206 (2009).
LaBelle, J.L. et al. A stapled BIM peptide overcomes apoptotic resistance in hematologic cancers. J Clin Invest 122, 2018-2031 (2012).
Walensky, L.D. et al. A stapled BID BH3 helix directly binds and activates BAX. Mol Cell 24, 199-210 (2006).
Okamoto, T. et al. Stabilizing the pro-apoptotic BimBH3 helix (BimSAHB) does not necessarily enhance affinity or biological activity. ACS Chem Biol 8, 297-302 (2013).
Mislick, K.A. & Baldeschwieler, J.D. Evidence for the role of proteoglycans in cation-mediated gene transfer. Proc Natl Acad Sci U S A 93, 12349-12354 (1996).
Richard, J.P. et al. Cellular uptake of unconjugated TAT peptide involves clathrin-dependent endocytosis and heparan sulfate receptors. J Biol Chem 280, 15300-15306 (2005).
Mietus-Snyder, M., Friera, A., Glass, C.K. & Pitas, R.E. Regulation of scavenger receptor expression in smooth muscle cells by protein kinase C: a role for oxidative stress. Arterioscler Thromb Vasc Biol 17, 969-978 (1997).
Li, H., Freeman, M.W. & Libby, P. Regulation of smooth muscle cell scavenger receptor expression in vivo by atherogenic diets and in vitro by cytokines. J Clin Invest 95, 122-133 (1995).
Voigt, J., Christensen, J. & Shastri, V.P. Differential uptake of nanoparticles by endothelial cells through polyelectrolytes with affinity for caveolae. Proc Natl Acad Sci U S A 111, 2942-2947 (2014).
Alam, M.R. et al. The biological effect of an antisense oligonucleotide depends on its route of endocytosis and trafficking. Oligonucleotides 20, 103-109 (2010).
Meier, O. et al. Adenovirus triggers macropinocytosis and endosomal leakage together with its clathrin-mediated uptake. J Cell Biol 158, 1119-1131 (2002).
Rossman, J.S., Leser, G.P. & Lamb, R.A. Filamentous influenza virus enters cells via macropinocytosis. J Virol 86, 10950-10960 (2012).
Hewlett, L.J., Prescott, A.R. & Watts, C. The coated pit and macropinocytic pathways serve distinct endosome populations. J Cell Biol 124, 689-703 (1994).
Wadia, J.S., Stan, R.V. & Dowdy, S.F. Transducible TAT-HA fusogenic peptide enhances escape of TAT-fusion proteins after lipid raft macropinocytosis. Nat Med 10, 310-315 (2004).
Muto, A. et al. Inhibition of Mitogen Activated Protein Kinase Activated Protein Kinase II with MMI-0100 reduces intimal hyperplasia ex vivo and in vivo. Vascul Pharmacol 56, 47-55 (2012).
Kalra, M. & Miller, V.M. Early remodeling of saphenous vein grafts: proliferation, migration and apoptosis of adventitial and medial cells occur simultaneously with changes in graft diameter and blood flow. J Vasc Res 37, 576-584 (2000).
Zwolak, R.M., Adams, M.C. & Clowes, A.W. Kinetics of vein graft hyperplasia: association with tangential stress. J Vasc Surg 5, 126-136 (1987).

(56) References Cited

OTHER PUBLICATIONS

Alexander, J.H. et al. The PRoject of Ex-vivo Vein graft ENgineering via Transfection IV (PREVENT IV) trial: study rationale, design, and baseline patient characteristics. Am Heart J 150, 643-649 (2005).

Goldberg, M., Langer, R. & Jia, X. Nanostructured materials for applications in drug delivery and tissue engineering. J Biomater Sci Polym Ed 18, 241-268 (2007).

Li, H., Nelson, C.E., Evans, B.C. & Duvall, C.L. Delivery of intracellular-acting biologics in pro-apoptotic therapies. Curr Pharm Des 17, 293-319 (2011).

Ferrito, M.a.T., D. A. Poly(2-ethylacrylic acid). Macromolecular Syntheses 11, 59-62 (1992).

Convertine, A.J., Benoit, D.S., Duvall, C.L., Hoffman, A.S. & Stayton, P.S. Development of a novel endosomolytic diblock copolymer for siRNA delivery. J Control Release 133, 221-229 (2009).

Henry, S.M., El-Sayed, M.E., Pirie, C.M., Hoffman, A.S. & Stayton, P.S. pH-responsive poly(styrene-alt-maleic anhydride) alkylamide copolymers for intracellular drug delivery. Biomacromolecules 7, 2407-2414 (2006).

Bolte, S. & Cordelieres, F.P. A guided tour into subcellular colocalization analysis in light microscopy. J Microsc-Oxford 224, 213-232 (2006).

Jiang, Z. et al. A novel vein graft model: adaptation to differential flow environments. Am J Physiol Heart Circ Physiol 286, H240-245 (2004).

Duvall et al. Mol Pharm. 2010;7(2):468-476.

Evans, et al., Endosomolytic Nano-Polyplex Platform Technology for Cytosolic Peptide Delivery to Inhibit Pathological Vasoconstriction; Acsnano; 2015; vol. 9, No. 6, pp. 5893-5907.

Evans, et al., MK2 inhibitory peptide delivered in nanopolyplexes prevents vascular graft intimal hyperplasia, ScienceTranslationalMedicine,Jun. 10, 2015, vol. 7 Issue 291, pp. 1-11.

Gupta Ketal: "Nanoparticle formation from poly(acrylic acid) and oppositely charged peptides", Biophysical Chemistry, North-Holland, Amsterdam, NL, vol. 119, No. 3, Feb. 1, 2006 (Feb. 1, 2006 ), pp. 303-306.

Gupta Ketal: "Nanoparticles of cationic chimeric peptide and sodium polyacrylate exhibit striking antinociception activity at lower dose", Journal of Controlled Release, Elsevier, Amsterdam, NL, val. 134, No. 1, Feb. 20, 2009 (Feb. 20, 2009), pp. 47-54.

Albarran et al: "Efficient intracellular delivery of a proapoptotic peptide with a pH-responsive carrier", Reactive & Functional Polymers, Elsevier Science Publishers BV, NL, val. 71, No. 3, Sep. 17, 2010 (Sep. 17, 2010), pp. 261-265.

Brian Connor Evans: "Biomedical Engineering Enhanced Intracellular Peptide Delivery With PH-Responsive, Endosomolytic Nano-Polyplexes to Modulate Vascular Smooth Muscle Cell Behavior", May 1, 2013.

Craig L. Duvall et al: "Intracellular Delivery of a Proapoptotic Peptide via Conjugation to a RAFT Synthesized Endosomolytic Polymer", Molecular Pharmaceutics, val. 7, No. 2, Apr. 5, 2010 (Apr. 5, 2010), pp. 468-476.

Lopes L Bet al: "A novel cell permeant peptide inhibitor of MAPKAP kinase II inhibits intimal hyperplasia in a human saphenous vein organ culture model", Journal of Vascular Surgery, C.V. Mosby Co., St. Louis, MO, US, val. 52, No. 6, Dec. 1, 2010 (Dec. 1, 2010 ), pp. 1596-1607.

Brian C Evans et al: "Nan 0 M E D I C I N E MK2 inhibitory peptide delivered in nanopolyplexes prevents vascular graft intimal hyperplasia", Jun. 10, 2015 (Jun. 10, 2015), vol. 7, Issue 291.

Brian C. Evans et al: "Endosomolytic Nano-Polyplex Platform Technology for Cytosolic Peptide Delivery to Inhibit Pathological Vasoconstriction", ACS NANO, val. 9, No. 6, Jun. 23, 2015 (Jun. 23, 2015), pp. 5893-5907.

Evans Be et al: "Enhanced Intracellular Peptide Delivery with pHresponsive, Endosomolytic Nano-Polyplexes to Prevent Intimal Hyperplasia in Human Saphenous Vein Grafts", Apr. 2013.

Takuya Wada et al: "[alpha]-amino acid pendant polymers as endosomal pH-responsive gene carriers", Macromolecular Research, vol. 20, No. 3, Mar. 1, 2012 (Mar. 1, 2012 ), pp. 302-308.

Sedlak, Marian,; Homopolymer Self-Assembly into Stable Nanoparticles: Concerted Action of Hydrophobic Association and Hydrogen Bonding in Thermoresponsive Poly(alkylacrylic acids)s, J. Jphys. Chem. B, 2012, 116, pp. 2356-2364.

Murthy, et al., The design and synthesis of polymers for eukaryotic membrane disruption, J. Control. Release, 1999, 61, pp. 137-143.

* cited by examiner

| NH2:COOH | Z-ave diameter (nm) | PDI |
|---|---|---|
| 10 to 1 | 27180 ± 25330 nm | 1 |
| 5 to 1 | 1335 ± 94.78 nm | 0.483 |
| 4 to 1 | 730.8 ± 821.2 nm* | 0.656 |
| 3 to 1 | 11750 ± 6316 nm | 1 |
| 2 to 1 | 3604 ± 1559 nm | 0.567 |
| 1 to 1 | 10990 ± 3748 nm | 1 |
| 1 to 2 | 660.5 ± 54.13 nm | 0.242 |
| 1 to 3 | 155.4 ± 14.65 nm | 0.251 |
| 1 to 4 | 193.0 ± 46.75 nm* | 0.313 |
| 1 to 5 | 392.5 ± 91.81 nm* | 0.458 |
| 1 to 10 | 261.8 ± 35.51 nm* | 0.583 |

| NH2:COOH | Z-ave diameter (nm) | PDI |
|---|---|---|
| 10 to 1 | 3255 ± 1413 | 0.761 |
| 5 to 1 | 7809 ± 4860* | 0.753 |
| 4 to 1 | 4554 ± 1662 | 0.958 |
| 3 to 1 | 5024 ± 2651 | 0.794 |
| 2 to 1 | 3888 ± 300* | 0.803 |
| 1 to 1 | 1955 ± 929.7 | 0.452 |
| 1 to 2 | 230.6 ± 35.62 | 0.432 |
| 1 to 3 | 159.8 ± 9.405 | 0.298 |
| 1 to 4 | 197.6 ± 12.99* | 0.465 |
| 1 to 5 | 202.9 ± 47.63* | 0.784 |
| 1 to 10 | 1352 ± 798.5* | 0.647 |

POLYPLEXES

RELATED APPLICATION

This application claims priority from International Patent Application No. PCT/US2014/033873, filed Apr. 11, 2014, which claims benefit to United States Provisional Patent Application Ser. No. 61/811,078, which was filed on Apr. 11, 2013, the entire disclosures of which are incorporated herein by this reference.

GOVERNMENT INTEREST

This subject matter of the present disclosure was made with support from the United States Government under Grant No. 11SDG4890030, awarded by the American Heart Association, Grant No. 1R21HL110056-01, awarded by the National Institutes of Health, and Fellowship No. DGE-090966, awarded by the National Science Foundation. The United States Government has certain rights in the subject matter of the present disclosure.

TECHNICAL FIELD

The presently-disclosed subject matter relates to polyplexes. In particular, the presently-disclosed subject matter relates to compositions comprising polyplexes that include oppositely charged polymers and active agents, wherein the active agents can be peptides.

INTRODUCTION

Peptides have significant potential for development of more specific and/or potent drugs when compared to synthetic small molecules. However, delivery barriers have limited translation of peptide-based drugs. For example, peptides typically have a larger molecular weight and are more hydrophilic than small molecule drugs, inhibiting their ability to directly diffuse through cell membranes. As a result, they are internalized via endosomal pathways that often result in entrapment in vesicles targeted for degradation in lysosomes or recycling out of the cell by exocytosis. Indeed, inefficient cell penetration and poor intracellular pharmacokinetics have been the major limitations to widespread clinical translation of peptide therapeutics, which are otherwise desirable drugs for disrupting intracellular protein-protein interactions based on their specificity, safety, and ease of manufacturing.

For example, MAPKAP Kinase II inhibitory peptide (MK2i) is a peptide that may have significant potential as a drug. MAPKAP Kinase II (MK2) signaling occurs in vascular smooth muscle cells (VSMCs). MK2 activation results in vasoconstriction and pathological VSMC proliferation, migration, and excess ECM production that lead to graft blockage. MK2i is therefore believed to theoretically reduce vasoconstriction and subsequent intimal hyperplasia in human saphenous vein (HSV).

In this regard, the signaling of MK2 is often triggered by environmental and mechanical stresses, such as those experienced when implanting a graft during surgical transplantation. Thus, while coronary artery bypass grafting with autologous conduits remains the standard treatment for multi-vessel coronary heart disease, almost half of these saphenous vein grafts fail within the first 18 months due to intimal hyperplasia. Current methods for delivering MK2i to treat intimal hyperplasia caused by grafts have not been successful, though, since peptides in current compositions are often sequestered within endo-lysosomal vesicles that are trafficked for exocytosis or lysosomal degradation.

Hence, there remains a need for improved compositions and methods for administering active agents, and particularly peptides, to a subject in need thereof.

SUMMARY

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of features.

The presently-disclosed subject matter provides, in some embodiments, a compound comprising (i) an active agent, wherein the active agent includes a charge at a predetermined p, and (ii) a polymer, wherein the polymer includes an opposite charge than the active agent at the predetermined pH. In some embodiments an electrostatic bond being formed between the active agent and the polymer at the predetermined pH, in some embodiments the bound active agent and polymer is referred to as a polyplex. In some embodiments, the predetermined pH is from about 6.5 to about 8. Furthermore, in some embodiments the electrostatic bond between the active agent (e.g., peptide) and the polymer is broken at an activation pH, which may be pH lower than the predetermined pH or lower than about 6.5.

In some embodiments the active agent is cationic at the predetermined pH and the polymer is anionic at the predetermined pH, and in other embodiments the active agent is anionic at the predetermined pH and the polymer is cationic at the predetermined pH. In some embodiments the active agent includes a peptide, such as a MAPKAP kinase II inhibitory peptide. In other embodiments the peptide includes one or more sequences selected from SEQ. ID. NOS: 1-4. In some embodiments the composition can further comprise a second active agent, such as a peptide, a polynucleotide, and combinations thereof, including in some embodiments siRNA, DNA, and combinations thereof.

In some embodiments the composition comprises a polymer that includes poly(($C_1$-$C_6$)alkyl-acrylic acid), poly(($C_1$-$C_6$)alkyl-methacrylic acid), poly(($C_1$-$C_6$)alkyl-ethacrylic acid), or combinations thereof. In certain embodiments the polymer includes poly(propylacrylic acid) (PPAA). Exemplary polymers can further include a hydrophilic block, which may comprise polyethylene glycol ("PEG"), N-(2-hydroxypropyl)methacrylamide ("HPMA"), poly(N,N-dimethylacrylamide) ("pDMA"), poly(PEG methacrylate) ("pPEGMA"), or a combination thereof.

Furthermore, some embodiments of the present disclosure comprise a charge ratio of a polymer to a peptide that is between about 10:1 and about 1:10. Further, in certain embodiments, the charge ratio of the polymer to the peptide is about 1:3.

The polyplex may have, in some embodiments, a size of about 50 nm to about 500 nm in at least one dimension, such as the diameter.

In certain embodiments, the present disclosure provides a pharmaceutical composition that comprises any composition described in the present disclosure, together with a pharmaceutically acceptable carrier.

In still other embodiments, the presently-disclosed subject matter provides a vascular graft, wherein the vascular graft comprises a composition according to any embodiment described herein.

And in still further embodiments, the present disclosure provides methods of treating a disease or condition, such as a vascular condition. These methods comprise at least the step of administering an effective amount of any composition of the present disclosure to a subject in need thereof. In certain embodiments, the vascular condition is intimal hyperplasia.

Finally, in certain embodiments, the present disclosure provides methods of synthesizing the compositions described herein.

DETAILED DESCRIPTION OF EXEMPLARY EMBODIMENTS

Figure 1:
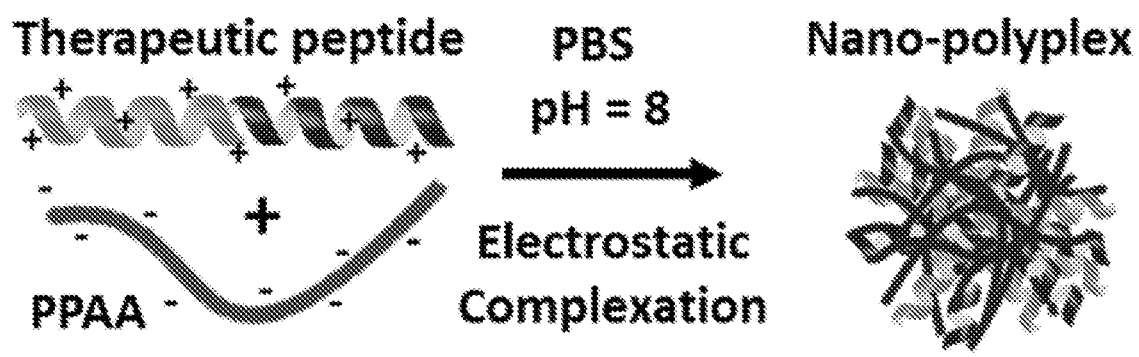
FIG. 1 provides a schematic for the synthesis of embodiments of polyplexes that comprise a cationic peptide, such as a peptide comprising MAPKAP Kinase 2 (MK2i), and an anionic, endosomolytic polymer, such as PPAA.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional components or limitations described herein or otherwise useful.

There is a need for compositions and methods for delivering active agents, including peptides, that can avoid the endosomal pathway, that have improved access to cytosolic targets, that have increased intracellular retention times, and that have improved bioactivity of intracellular-acting peptide drugs. The subject matter of the present disclosure meets at least each of these needs.

The presently-disclosed subject matter includes compositions comprising a peptide and a polymer, wherein the peptide and the polymer are electrostatically bound to one another to form a polyplex at a predetermined pH. The term "polyplex" is used herein to refer to electrostatically-bound peptide and polymer that form a cluster, particle, agglomeration, or the like. Thus, embodiments of the presently-disclosed subject matter include compositions that comprise polyplexes of a peptide and a polymer.

Polymer

The term "polymer" is used herein to refer to a polymeric compound prepared by polymerizing monomers, whether of the same or a different type. The generic term "polymer" thus includes the term homopolymer, or a polymer formed of the same type of monomer units, and the term copolymer, or a polymer formed of two or more different types of monomer units.

In some embodiments the polymer can include one or more monomers selected from ($C_1$-$C_6$)alkyl-acrylic acid, ($C_1$-$C_6$)alkyl-methacrylic acid, and ($C_1$-$C_6$)alkyl-ethacrylic acid, and combinations thereof. For example, in some embodiments the ($C_1$-$C_6$)alkyl-acrylic acid monomer includes propyl acrylic acid (PAA), propyl acrylic acid, butyl acrylic acid, and so forth. The resulting polymer can consist of or comprise poly(($C_1$-$C_6$)alkyl-acrylic acid), poly(($C_1$-$C_6$)alkyl-methacrylic acid), and poly(($C_1$-$C_6$)alkyl-ethacrylic acid), and combinations thereof. In specific embodiments the polymer is a poly(propylacrylic acid) (PPAA) polymer.

The term "alkyl" refers to alkyl groups with the general formula $C_nH_{2+1}$, where n=about 1 to about 18 or more. The groups can be straight-chained or branched. Alkyl, when used herein, also comprise "lower alkyls," which refer to alkyl groups with the general formula $C_nH_{2+1}$, where n=1 to about 6. In some embodiments, n=1 to about 3. Examples include methyl, ethyl, propyl, isopropyl, n-butyl, sec-butyl, t-butyl, isobutyl, n-pentyl, isopentyl, neopentyl, n-hexyl, and the like. In this regard, the term "cycloalkyl" refers to a non-aromatic carbon-based rings composed of at least three carbon atoms, such as cyclopropyl, cyclohexyl, and the like. The term alkyl is inclusive of cycloalkyls.

In some embodiments, functionalized versions of monomers are optionally used in the present polymers. A functionalized monomer, as used herein, is a monomer comprising a masked or non-masked functional group, e.g. a group to which other moieties can be attached following the polymerization. The non-limiting examples of such groups are primary amino groups, carboxyls, thiols, hydroxyls, azides, and cyano groups. Several suitable masking groups are available (see, e.g., T. W. Greene & P. G. M. Wuts, Protective Groups in Organic Synthesis (2nd edition) J. Wiley & Sons, 1991. P. J. Kocienski, Protecting Groups, Georg Thieme Verlag, 1994).

In some embodiments, the polymer is a pH-responsive polymer. In certain instances, the term polymer as used herein in inclusive of pH-response polymers. A pH-response polymer includes a polymer that experiences a change in its charge depending on pH. The polymer can be cationic or anionic at a predetermined pH, which can include a specific pH, a range of pH, above a certain pH, and/or below a certain pH. For instance, poly(alkyl acrylic acid) comprises carboxylic acid groups, and poly(propylacrylic acid) has a pKa of about 6.7. Poly(propylacrylic acid) has an anionic character when it is at a pH higher than its pKa. However, when it is at a pH at about or below its pKa, the carboxylic acid group become protonated, and poly(propylacrylic acid) no longer has an anionic character or at least not as great an anionic character as it did at the predetermined pH. This change in charge makes poly(propylacrylic acid) and other poly(alkyl acrylic acid) exemplary pH-responsive polymers.

Those of ordinary skill in the art will appreciate other polymers that comprise groups that will have different charges depending on the pH of the polymer's environment. The pH at which the polymer's charge changes can be at a pH that is lower than, equal to, or higher than its pKa. Thus, polymers having charged groups at a predetermined pH can be desirable for use in forming a polyplex, and in certain embodiments of the present disclosure, the polymer comprises a charge when at a physiological pH.

Thus, exemplary monomers and polymers can be either anionic or cationic at about physiological pH and/or at about pH 6.0, about pH 7.0, about pH 8.0, at about endosomal pH (e.g., about pH 5 to pH 6), or a combination thereof. In some embodiments the monomers become increasingly protonated at a pH of below about pH 7.4, below about pH 7.0, below about pH 6.5, below about pH 6.0, below about pH 5.0, below about pH 4.5, or below about pH 4.0.

The at least partially disassembly of the polyplexes can expose the polynucleotides that are bound to in the core of the polyplexes to the surrounding environment. Thus, at least partial disassembly of the polyplexes can allow the polynucleotides to be delivered to their final target. At least partial disassembly can also expose the cationic monomers and/or hydrophobic monomers to the surrounding environment, and the cationic monomers and/or hydrophobic monomers can have a membrane disruptive character. Thus, exposure of these monomers can induce disruption of membranes that contain the polyplexes. In some embodiments, after the uptake of the polyplexes into a cell, the polyplexes can at least partially disassemble to deliver the polynucleotide to the cytosol in a pH-responsive manner. In some embodiments the polyplexes at least partially disassemble at or below about endosomal pH, and the at least partially disassembled polyplexes can disrupt the endosomal or liposomal membranes so that the polynucleotide can be delivered to the cytosol of a particular cell.

In this regard, the present monomers and polymers can have a membrane disruptive character. Thus, exposure of these monomers can induce disruption of membranes that contain the polyplexes. In some embodiments, after the uptake of the polyplexes into a cell, the polyplexes can at least partially disassemble to deliver the polynucleotide to the cytosol in a pH-responsive manner. In some embodiments the polyplexes at least partially disassemble at or below about a predetermined pH (e.g., endosomal pH), and the at least partially disassembled polyplexes can disrupt the endosomal or liposomal membranes so that the active agent can be delivered to the cytosol of a particular cell.

Still further, embodiments of polymers comprise a copolymer that includes one or more hydrophilic blocks. The term "hydrophilic block" means a block comprising at least about 50 mol % of water-soluble and/or water-dispersible monomers. In such embodiments, the remaining monomers that have been described above form what is referred herein as the "pH-responsive block." In some embodiments, a polymer that includes a hydrophilic block can form a particle (e.g., polyplex) that includes a corona substantially comprising the hydrophilic blocks and a core substantially comprising the pH-responsive blocks of the polymers.

Thus, the hydrophilic block and the remaining block(s) of the polymer can assemble the polymers into micelles that include hydrophilic surface groups (i.e., a corona) made of hydrophilic polymer blocks. The hydrophilic polymer blocks can include monomers selected from polyethylene glycol (PEG), N-(2-hydroxypropyl)methacrylamide (HPMA), poly(N,N-dimethylacrylamide) (pDMA), poly (PEG methacrylate) (pPEGMA), combinations thereof, and the like. Some compositions comprising hydrophilic blocks in the polymer can achieve a higher stability and enhanced delivery of the peptide when administered intravenously, intra-arterially, or the like. In some embodiments the molar ratio of hydrophilic monomers relative to the other monomers (i.e., pH-responsive monomers) can be about 10 mol %, 15 mol %, 20 mol %, 25 mol %, 30 mol %, 35 mol %, 40 mol %, 45 mol %, 50 mol %, 55 mol %, 60 mol %, 65 mol %, 70 mol %, 75 mol %, 80 mol %, 85 mol %, and/or 95 mol %.

The present polymers can vary in size. The size may or may not depend on the subject being treated, the active agent being delivered, the monomers that form the polymer, or the like. Exemplary polymers can include a size of about 10,000 Da, 15,000 Da, 20,000 Da, 25,000 Da, 30,000 Da, 35,000 Da, 40,000 Da, 45,000 Da, or 50,000 Da. In certain embodiments wherein the polymer includes a hydrophilic block, the hydrophilic block can be about 500 Da, 5,000 Da, 10,000 Da, 15,000 Da, or 20,000 Da, and the pH-responseive block can be about 5,000 Da, 10,000 Da, 15,000 Da, 20,000 Da, 25,000 Da, 30,000 Da, 35,000 Da, 40,000 Da, 45,000 Da, or 50,000 Da.

Active Agent

The presently-disclosed subject matter further comprises active agents to be used in conjunction with embodiments of the present polymers. In some embodiments the active agents comprise an electrostatic charge when at, below, or above a predetermined pH. The term "active agent" is used herein to refer to a compound or entity that alters, promotes, speeds, prolongs, inhibits, activates, eliminates, or otherwise affects biological or chemical events in a subject. In some embodiments, the present polyplexes further comprise a second active agent or additional active agents. In certain embodiments the active agent is a peptide, nucleic acids (e.g., DNA, siRNA), antibiotics, or the like.

The terms "polypeptide", "protein", and "peptide", are used interchangeably herein to refer to a polymer of the amino acids, or amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, non-naturally occurring proteins, homologs, orthologs, paralogs, fragments and other equivalents, variants, and analogs of the foregoing. Furthermore, the term "fusion polypeptide" is used herein to generally refer to a polypeptide formed from two or more distinct polypeptides.

In some embodiments, the peptide that is an active agent comprises MAPKAP Kinase II inhibitory peptide (MK2i). Without being bound by theory or mechanism, it is believed that the MK2i peptide has activity as an anti-inflammatory, and it inhibits F-actin stress fiber formation that drives smooth muscle cell migration, which can cause neointima formation and constriction of vessels. MK2i is therefore believed to enhance vaso-relaxation and to reduce the formation of neointima. Accordingly, MK2i can be beneficial when used in conjunction with vascular grafting procedures, particularly saphenous vein grafting.

For additional information regarding the MK2 peptide and/or MK2i peptide, see U.S. Patent Application Publication Nos. 2012/0263680, 2011/0288036, and 2008/0293640, which are hereby incorporated by reference in their entirety.

The peptides can be electrostatically charged. In some embodiments, the peptides of the present disclosure are electrostatically charged when they are at a predetermined pH. For example, peptides can be cationic or anionic at, below, or above, the predetermined pH. Those of ordinary skill in the art will appreciate that various peptides having functional groups (e.g., amine groups) that have a charge at least when the peptide is at a pH that is lower than, equal to, or higher than the pKa of the peptide. Some preferred embodiments comprise peptides that are charged (e.g., cationic) at physiological pH.

Some exemplary embodiments of compositions of the present disclosure comprise the MK2i peptide, which includes primary amines that impart a cationic character on MK2i when the MK2i is at a pH that is lower the pKa of the primary amines (i.e., about pH 9 to about pH 12). Other exemplary peptides include BH3 mimetic inhibitors of Bak, which can be used to trigger cancer cell apoptosis, and which can be charged at a predetermined pH. Another exemplary peptide includes the AZX100 peptide (SEQ ID NO: 2), which can be utilized for airway relaxation. In yet other embodiments the active agent can be a proapoptotic peptide, including, but not limited to, the RN22 peptide (SEQ ID NO: 3) and the Penetratin-Bak-BH3 peptide (SEQ ID NO: 4). Thus, depending on the peptide used in a composition, the composition can be used to treat a variety of different conditions and/or diseases.

In some embodiments, the peptide can be a fusion peptide that includes two distinct peptides. The peptide that is a fusion peptide can include a first peptide that comprises an active agent and a second peptide that comprises a cell-penetrating peptide. Cell-penetrating peptides generally are peptides that trigger, accelerate, activate, or facilitate the cellular uptake of the cell-penetrating peptide and/or any molecule bound thereto.

For instance, in some embodiments, the cell-penetrating peptide is "YARA". YARA can be bound to a first peptide that includes an active agent. Other cell-penetrating peptides include the TAT peptide, the Antennapedia (AntP) peptide, as well as other cell penetrating peptides that are known in the art. In some embodiments, the cell-penetrating peptide and the active agent of a peptide are YARA and MK2i, respectively. As used herein, "YARA-MK2i" (SEQ ID NO: 1) refers to a peptide comprising both a cell penetrating peptide (YARA) and a MAPKAP Kinase II inhibitor peptide (MK2i).

Accordingly, in some embodiments the active agent is a peptide. In some embodiments the peptides further comprise a cell penetrating peptide. The cell penetrating peptide can be the same peptide or a separate peptide from the active agent peptide. Furthermore, in some embodiments the active agent is a fusion peptide that includes a portion that is an active agent peptide and another portion that is a cell-penetrating peptide.

Polyplex

The presently-disclosed subject matter further comprises polyplexes that comprise the polymers and the active agents that are described herein. In some embodiments, the polymer and the active agent have opposite charges at a predetermined pH, and therefore can electrostatically bind to form polyplexes when at the predetermined pH. The predetermined pH can be above the pKa of the active agent (e.g., peptide) or polymer and below the pKa of the other of the active agent or the polymer. For example, the predetermined pH can be a pH of about 6.5 to about 8.0, and more specifically can be about pH 6.5, about pH 6.6, about pH 6.7, about pH 6.8, about pH 6.9, about pH 7.0, about pH 7.1, about pH 7.2, about pH 7.3, about pH 7.4, about pH 7.5, about pH 7.6, about pH 7.7, about pH 7.8, about pH 7.9, or about pH 8.0. The predetermined pH can also be a physiological pH of a subject. As used herein, the term "at a predetermined pH" can refer to a pH that is a specific pH, below a particular pH, above a particular pH, or within a range of pH.

Embodiments of the present polyplexes can form with particular polymers and active agents that are oppositely charged at a predetermined pH. Formation of embodiments of the present polyplexes can occur when polymer and active agent is both present at a predetermined pH. Thus, in some embodiments a polyplex includes a polymer and an active agent that are held together at least via electrostatic interactions. As described herein, the charge of the present polymers and/or active agents can neutralize, strength, or change from positive to negative or negative to positive when the pH is changed from the predetermined pH to a pH that is not the predetermined pH. When this occurs the polymer and the active agent can change such that they no longer have opposing charges and/or have less of a degree of opposing charges, thereby permitting disassembly of the polyplexes.

In this regard, at least partially disassembly of the polyplexes can expose the active agents (e.g., polynucleotides), which were bound to and comprise the polyplexes, to the surrounding environment. Thus, at least partial disassembly of the polyplexes can allow the active agents to be delivered to their final target. As described herein, at least partial disassembly can also expose polymers that can have a membrane disruptive character. In some embodiments, after the uptake of the polyplexes into a cell, the polyplexes can at least partially disassemble to deliver the active agent to the cytosol in a pH-responsive manner. In some embodiments the polyplexes at least partially disassemble at or below about endosomal pH, and the at least partially disassembled polyplexes can disrupt the endosomal or liposomal membranes so that the active agent can be delivered to the cytosol of a particular cell. Accordingly, embodiments of the present polymers that form polyplexes with an active agent are endosomolytic, and thereby can permit and/or enhance the cytosolic delivery of active agents that have entered a cell via the polyplex.

A specific embodiment of a polyplex comprises a composition of MK2i and poly(propylacrylic acid). At a predetermined pH of about 6.5 to about 8.0, the MK2i is anionic and the poly(propylacrylic acid) is cationic. The composition can therefore form and/or comprise a polyplex of MK2i and poly(propylacrylic acid) when at the predetermined pH of about 6.5 to about 8.0.

The compositions can be activated when subjected to an activation pH. In some embodiments, the activation pH is a pH that is lower than the predetermined pH. In some embodiments, the activation pH is about a pH found in the early endosomes of a subject's cells. When the composition is at the activation pH, the electrostatic bond between the peptide and the polymer can be broken (e.g., cleaved). The bond is broken whenever it is weakened or eliminated such that the two or more bound molecules can dissociate from one another.

For instance, some embodiments of compositions that include a MK2i peptide and a poly(propylacrylic acid) polymer also have an activation pH of about 6.5 of lower. Thus, when an MK2i and poly(propylacrylic acid) polyplex is exposed to a pH of 6.5 or lower, the MK2i and poly (propylacrylic acid) can dissociate from one another.

By virtue of being activated at an activation pH, compositions of polyplexes that are at an activation pH can activate the active agent from an inert bound state to an active unbound state. The dissociation of the polymer and active agent can also activate membrane-disruptive activity that enables endosome interaction and/or disruption and the escape of the peptide from the endo-lysosomal or recycling pathway, which can permit the peptide to be delivered from the endosome or the like into the cytosol. Subsequently, the active agent can target one or more cytosolic or other targets within the cell.

Thus, unlike prior compositions, and without being bound by theory or mechanism, embodiments of the presently-disclosed subject matter can first enter the endosomal pathway of target cells, and are then capable of being pH-activated to at least partially escape from the endosomes into the cytosol of the target cell. This has the advantage of increasing the efficacy of the peptide active agent. This can also increase the intracellular retention time and/or the bioactivity of the peptides relative to peptides administered alone or bound only to a cell-penetrating peptide.

Further still, the composition and/or polyplex can comprise a wide range of different concentrations of active agent and polymer. In some embodiments, the relative concentrations of active agent and/or polymer are determined by a charge ratio, or the molar ratio of charged groups on the active agent to the molar ratio of charged groups on the polymer. For example, if the composition comprises MK2i and poly(acrylic acid), the charge ratio can be defined as the molar ratio of $[NH_3^+]:[COO^-]$. Exemplary compositions comprise charge ratios of about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10.

Peptide bioactivity is shown, in some embodiments, in terms of inhibition of inflammatory signal production (TNF-alpha) in response to the pathological signal angiotensin II (Ang II) in vascular smooth muscles cells. In human saphenous vein (HSV), PPAA polyplexes are shown to enhance vasorelaxation of HSV and to reduce the formation of neointima in HSV.

In certain embodiments, the predetermined pH is selected with respect to the pKa values of the primary amines present on a peptide active agent and/or the carboxylic acid groups present in the polymer. In certain embodiments, the pKa of the peptide is between about 9 and about 12 and/or the pKa of the polymer is between about 6 and about 7. This mixing results in the formation of the polyplexes.

In some embodiments, the compositions/compounds of the present disclosure comprise polyplexes that have dimensions that can be measured at least on a nanoscale or other submicron scale. The size of the polyplexes can be optimized for cellular delivery and especially for cellular delivery via the endosomal pathway. In other embodiments, the composition can comprise polyplexes that measure about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, about 200 nm, about 210 nm, about 220 nm, about 230 nm, about 240 nm, about 250 nm, about 260 nm, about 270 nm, about 280 nm, about 290 nm, about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, or about 500 nm in at least one dimension. In certain embodiments the polyplexes have a size of about 90 nm to about 200 nm in at least one dimension, such as the diameter. Because certain polyplexes can be measured on a nanoscale, polyplexes may also be referred to nanoparticles or nano-polyplexes herein.

In some embodiments the polymers include a hydrophilic block that can form an outer shell (corona) of the polyplex and that can protect the polyplexes. In some embodiments such blocks on the polymers can reduce or eliminate the extent to which the polyplexes adsorb proteins. Hydrophilic outer shells on exemplary polyplexes can also inhibit hemolysis or aggregation of erythrocytes, avoid immune stimulation, improve circulation time, protect the cargo (e.g., active agent) from enzymatic degradation, provide colloidal stability and 'stealth', or a combination thereof.

The presently-disclosed subject matter still further includes methods for synthesizing any of the compositions described herein, including the polyplexes and/or pharmaceutical compositions thereof described herein. In some embodiments, the method comprises mixing a polymer and an active agent at a predetermined pH so that the polymer and peptide are partially or completely oppositely charged and electrostatically bind to form at least one polyplex. The concentration of the polymer and the peptide used to form the composition are not particularly limited. In some embodiments, the polymer and the peptide are mixed at concentrations such that the charge ratio achieved by the two components is about 10:1 to about 1:10. In some embodiments the polymer and the peptide are mixed in a buffer, such as a PBS buffer.

As described above, in some embodiments, the active agent can include a peptide that further comprises a cell-penetrating peptide. In this regard, methods for synthesizing polyplexes that include a cell-penetrating peptide can comprise a step of fusing the active agent (e.g., peptide) to the cell-penetrating peptide before the step of mixing the active agent and the polymer. The resulting composition therefore comprises at least one polyplex that includes the polymer and a fusion peptide of an active agent peptide and the cell-penetrating peptide.

In some embodiments, the disclosure is directed to a method of synthesizing a polyplex composition, wherein the method includes the step of mixing an active agent, such a peptide (e.g., a YARA-MK2i fusion peptide), with a polymer, such as the pH-responsive, endosomolytic polymer PPAA, at a pre-determined pH.

During use, in a method of treatment, or to disassemble the polyplexes the polyplexes can transitioned from the predetermined pH, which may be a range of pH, to an activation pH, which can be a range of pH. This transition can facilitate the at least partial disassembly of the polymers and active agents comprising the polyplexes.

Compositions and Devices

The presently-disclosed subject matter further includes pharmaceutical compositions of the compositions, polyplexes, peptides and/or polymers disclosed herein. Further, the presently-disclosed subject matter also includes any pharmaceutically-acceptable salts, solvates, physiologically functional derivative and/or pharmaceutically-acceptable derivative of the compounds described herein.

Such pharmaceutical compositions may include a pharmaceutically-acceptable carrier. In this regard, the term "pharmaceutically acceptable carrier" refers to sterile aqueous or non-aqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars, such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

The compositions can also be formulated as a preparation for implantation or injection. Thus, for example, the compositions can be formulated with suitable polymeric or hydrophobic materials (e.g., as an emulsion in an acceptable oil). In some embodiments the composition is prepared with or on a device or material for implantation. Exemplary devices that can be used with embodied compositions include vascular grafts (e.g., saphenous vein grafts) that include the composition, such as MK2i-containing compositions. The composition can be provided within the material that forms a device, on a surface of a device, or the like. Embodiments of graft devices that comprise the composition can have the capability of delivering the composition directly to a point where the graft may cause intimal hyperplasia, or the like. Devices can include a broad array of medical devices for implantation in a subject. Devices are also inclusive of materials, including biomaterials, that may be implanted in or on a subject.

The presently-disclosed subject matter further includes a kit that can include a composition or pharmaceutical composition as described herein, packaged together with a device useful for administration of the composition or pharmaceutical composition. As will be recognized by those or ordinary skill in the art, the appropriate administration-aiding device will depend on the formulation of the composition or pharmaceutical composition that is selected and/or the desired administration site. For example, if the formulation of the composition is appropriate for injection in a subject, the device could be a syringe. For another example, if the desired administration site is cell culture media, the device could be a sterile pipette. For yet another example, if the desired administration site is a vein or artery, the device could be a graft.

Furthermore, since exemplary compositions can increase the efficacy of the associated peptide, some embodiments of compositions are capable of elongating the time period that a dose of a peptide shows activity in a subject. This can be particularly helpful in applications where administration is difficult or can only be given a limited number of times. For instance, vascular grafts are typically treated only one time with an active agent (i.e., during surgery and/or transplantation), and therefore it is desirable that compositions administered in conjunction with vascular grafts be capable of elongating the time period that the associated peptides exhibit biological activity.

Methods of Use

The presently-disclosed subject matter further includes methods for treating conditions and/or disease with a composition. The methods of the present disclosure comprise administering an effective amount of any of the compositions (i.e., composition comprising polymer and active agent) described herein to a subject. In some embodiments, the condition for treatment is a vascular condition, such as intimal hyperplasia. Those of ordinary skill in the art will also appreciate various other conditions affecting the vascular, as well as other, systems, which can be treated with compositions that include active agents according to the present disclosure. In some embodiments the subject is being treated for a disease or condition treatable by an active agent that is a peptide, including peptides that are or that include cell-penetrating peptides. Certain embodiments therefore provide methods for administering active agents to treat certain conditions, wherein the method of treating the condition with the composition can increase the efficacy, longevity, or the like of the active agents.

The term "administering" refers to any method of providing a composition and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can comprise topically administering the composition be submerging a tissue to be treated, such as a vein, in a solution that includes the composition. Administration can also be accomplished by providing a device or material that includes the composition or pharmaceutical composition thereof, and then implanting or otherwise providing the device or material to a subject. Administration can be continuous or intermittent. In various aspects, a preparation can be administered therapeutically; that is, administered to treat an existing disease or condition (e.g., intimal hyperplasia, etc.). In further various aspects, a preparation can be administered prophylactically; that is, administered for prevention of a disease or condition.

In some embodiments, a subject will be administered an effective amount of the composition. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compositions employed; the duration of the treatment; drugs used in combination or coincidental with the specific compositions employed and like factors well known in the medical arts. For example, it is well within the skill of the art to start doses of a composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Additionally, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

The terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

EXAMPLES

The presently-disclosed subject matter is further illustrated by the following specific but non-limiting examples. The examples may include compilations of data that are representative of data gathered at various times during the course of development and experimentation related to the presently-disclosed subject matter.

The inventors of the present disclosure have developed a generalizable approach for cytoplasmic delivery and retention of therapeutic peptides by formulation of endosomolytic nano-polyplexes (NPs). This technology may be used, for example, for delivery of an anti-inflammatory cell penetrating peptide (CPP), such as inhibitor of MAPKAP Kinase 2 (MK2i) to block intimal hyperplasia (IH) within vascular bypass grafts.

The potency and longevity of action of MK2i, like many CPPs, suffer from entrapment within the endolysosomal pathways and limited bioavailability to cytoplasmic targets. However, it has been discovered that formulation into MK2i-NPs significantly enhances peptide uptake, endosomal escape, intracellular half-life, and bioactivity in vitro. Indeed, MK2i-NPs block inflammatory signaling and inhibit IH in human saphenous vein ex vivo and significantly reduce IH in vivo in a rabbit vein transplant model. Thus, the presently-disclosed NP technology provides a new delivery platform with potential for broader use for the intracellular delivery of peptide therapeutics, and the promising MK2i-NP data presented herein motivate continued clinical translation of this approach for reducing vein graft failure.

Here, a novel peptide delivery system has been developed with an initial focus on therapy for the leading killer, coronary heart disease (CHD). Coronary artery bypass grafting with autologous saphenous vein and internal mammary artery is the current standard of treatment for multi-vessel CHD; however, almost half of saphenous vein grafts fail within 18 months due to intimal hyperplasia (IH). One of the underlying causes of IH is activation of the p38 mitogen activated protein kinase pathway in vascular smooth muscle cells (VSMCs) due to mechanical and biochemical stresses on the graft during harvest and post-transplantation arterialization/adaptation to the faster and more pulsatile blood flow in the heart. Activated p38 phosphorylates MAPKAP Kinase II (MK2), triggering translocation of phosphorylated MK2 from the nucleus to the cytosol, where it propagates signals that induce an inflammatory response, vasoconstriction, and a pathological VSMC phenotype that, when combined, lead to IH, and ultimately, graft occlusion and failure. During revascularization procedures, the autologous vein is typically explanted for 30 minutes prior to transplant. As a result, treatment during explant provides a situation for topical treatment to enhance delivery to the target tissue while limiting off-target, systemic effects. However, this brief treatment window benefits from a therapeutic approach that maximizes uptake and the duration of action to ensure therapeutic efficacy throughout the entire vein graft arterialization/adaptation phase.

Clinical trials on p38 inhibitors have failed because of the toxicity associated with blocking the pleotropic effects of this upstream mediator. This motivated pursuit of MK2 as an anti-inflammatory target, but small molecule MK2 inhibitors have also failed at gaining FDA approval due to lack of specificity and water solubility. However, an effective cell-penetrating peptide (CPP) MK2 inhibitor (MK2i) has been developed that has some activity in human saphenous vein; unfortunately, MK2i potency is hindered by poor cell uptake and sequestration within late endosomes/early lysosomes, resulting in inefficient intracellular bioavailability to activated MK2 localized to the cytoplasm.

Herein, a simple and translational method is disclosed for formulation of endosomolytic, electrostatically-complexed polyplexes that efficiently deliver MK2i into vascular cells and tissues, enhancing peptide bioactivity by an order of magnitude in vitro, ex vivo, and in vivo. MK2i-NPs have strong potential for clinical translation to improve performance of vascular bypass grafts, and the NP approach represents a significant breakthrough in pharmaceutical technology poised for generalized use as a delivery vector for bioactive peptides.

Example 1

A poly(propylacrylic acid) (PPAA) homopolymer (Mn=22,000, PDI=1.47) was synthesized via reversible addition fragmentation chain transfer (RAFT) polymerization. The MK2i peptide (sequence: YARAAARQARAKA-LARQLGVAA) was synthesized through standard FMOC chemistry and purified via reverse-phase high-performance liquid chromatography (HPLC). The MK2i peptide and PPAA polymer were mixed at a range of charge ratios (CR, defined [$NH_3^+$]/[$COO^-$]) from 10:1 to 1:10 to form polyplexes.

The size, polydispersity, and zeta potential of the polyplexes was measured with dynamic light scattering (DLS). A charge ratio of 1:3 was chosen as the optimal formulation for further study, which creates polyplexes having a hydrodynamic diameter of about 119±27 nm and a zeta potential ($\zeta$) of about −11.9±3.2 mV). The pH-dependent peptide release and membrane disruptive (i.e., endosomolytic) behavior of the polyplexes was characterized using DLS and a red blood cell hemolysis assay. In vitro MK2 inhibition was assessed through an ELISA to quantify downstream inhibition of Interleukin-6 (IL-6) production in TNFα-stimulated human coronary artery vascular smooth muscle cells (HCAVSMCs). Human saphenous vein (HSV) explants were obtained from consenting human patients, and vasorelaxation of 1 mm thick vein ring segments were assayed ex vivo using a muscle bath/force transducer.

Rings were treated for two hours with MK2i polyplexes, MK2i alone, or controls and subsequently were contracted with phenylephrine ($10^{-6}$ to $10^{-7}$ M) and then relaxed with cumulative log doses of sodium nitroprusside to determine percent relaxation. Additional vein rings are cultured for 14 days, fixed, embedded in paraffin, sectioned, stained with Verhoeff-van Gieson stain, and used to quantify intimal and medial thickness to assess the ability of the polyplex treatments to abrogate graft intimal hyperplasia.

Figure 2:
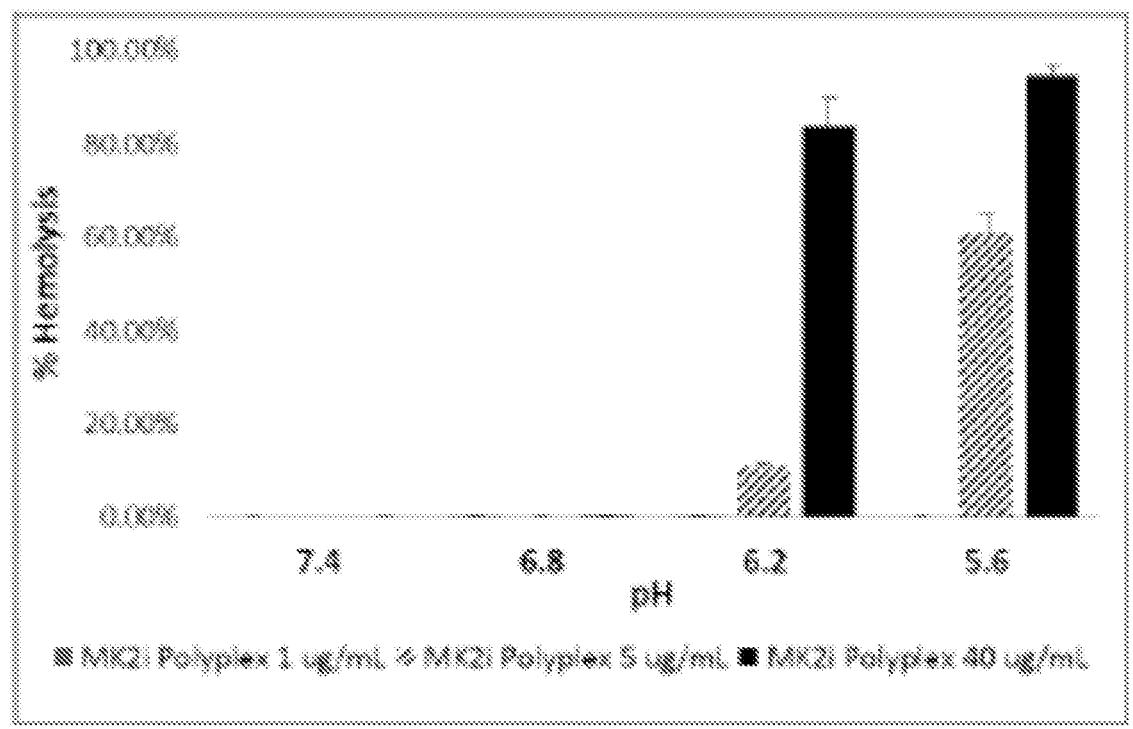
FIG. 2 presents the results of a hemolysis assay, which demonstrate that embodiments of polyplexes can be tuned for escape from endolysosomal pathways with a pH-dependent membrane disruption mechanism.

The results from dynamic light scattering are that polyplexes (CR=1:3) are about 119 nm in size at pH 7.4 and demonstrate dissociation into individual polymer and peptide unimers at or below pH 6.8, providing an effective mechanism for release of the peptide from the polyplex in endosomes. Polyplexes showed no hemolytic behavior at pH 7.4 or 6.8, but show switch-like, robust hemolysis at pH 6.2 and 5.6. These data suggest that, following polyplex dissociation and peptide release, further acidification of endosomal vesicles triggers pH-dependent endosomolytic activity and enables peptide cytosolic delivery (FIG. 2).

Figure 3:
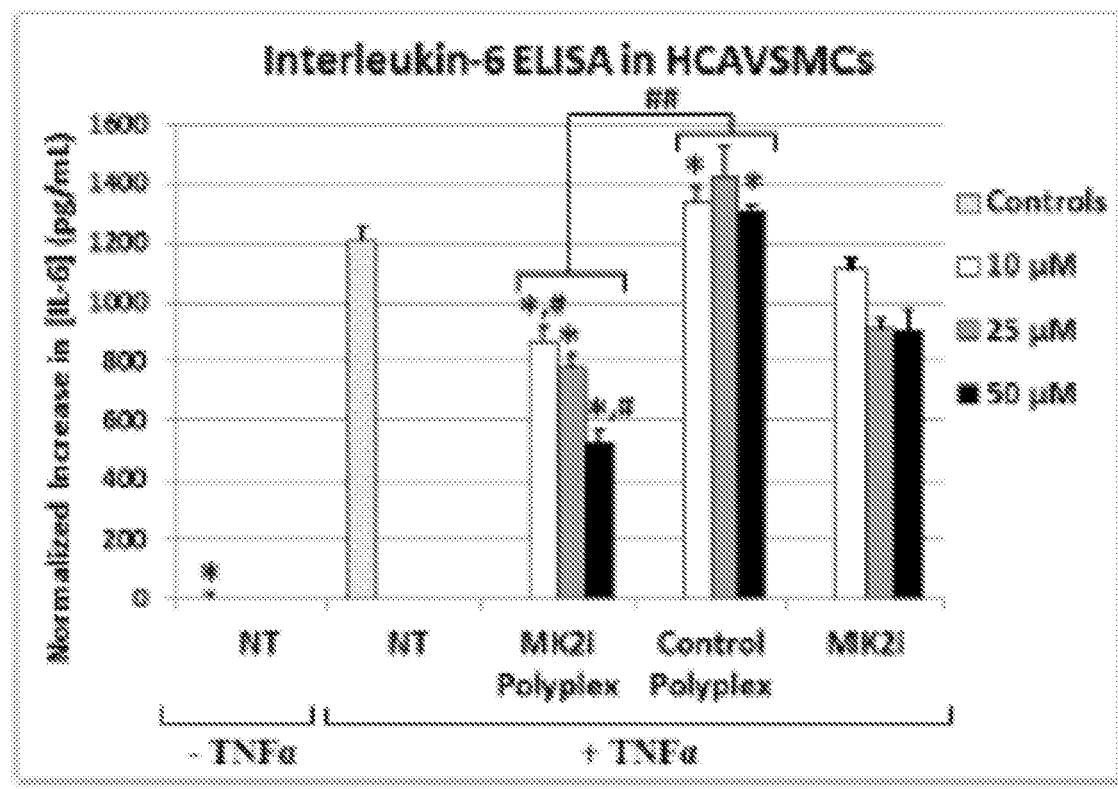
FIG. 3 shows some embodiments of the polyplexes of the present disclosure abrogating Interleukin-6 (IL-6) production relative to control polyplexes and to free MK2i in human coronary artery vascular smooth muscle cells (HCAVSMCs). All data provided in FIG. 3 is normalized to cell number. Further, "NT" means no treatment. *$p<0.05$ compared to NT+TNFα, *$p<0.01$ compared to NT+TNFα, #$p<0.05$ compared to MK2i at same concentration, ## $p<0.05$ compared to CPP polyplexes at same concentration, n=4.

Bioactivity of MK2i polyplexes was confirmed in vitro. It was observed that polyplexes comprising MK2i inhibited TNFα induced IL-6 secretion in HCAVSMCs compared to MK2i alone (FIG. 3).

Figure 4:
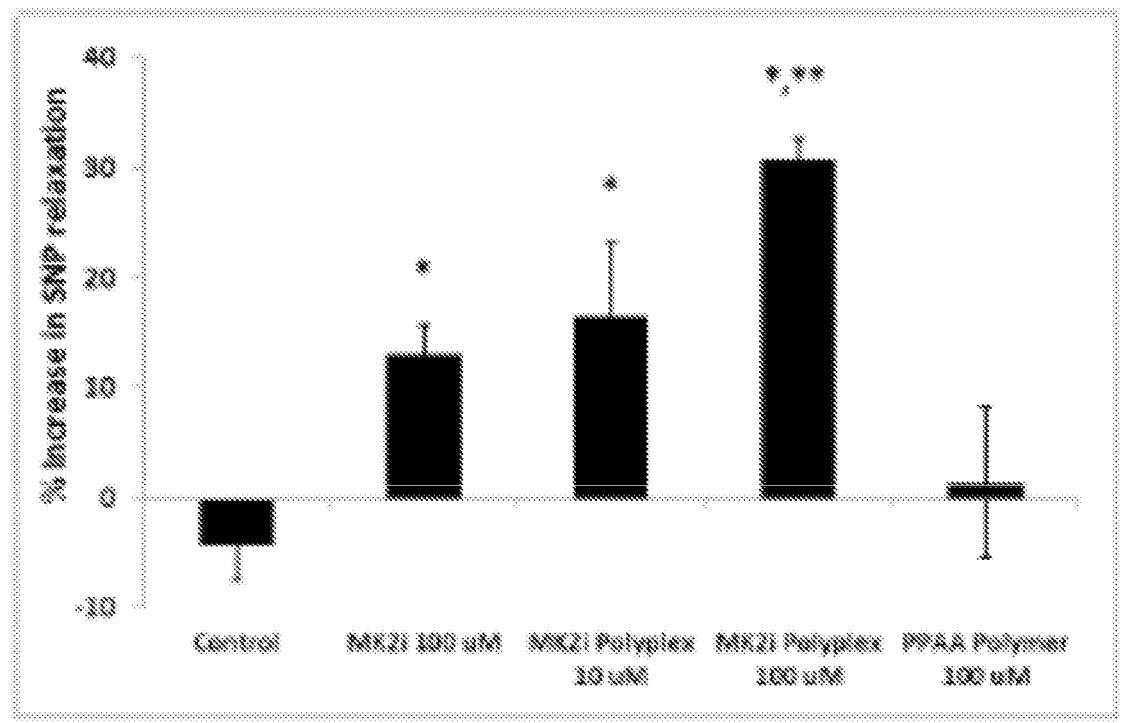
FIG. 4 provides a bar graph that illustrates the percent increase in relaxation of human saphenous vein (HSV) samples that were treated with blank polyplexes, with MK2i alone, with PPAA alone, or with embodiments of polyplexes comprising MK2i. *$p<0.05$ compared to control, **$p<0.05$ compared to 100 μm MK2i, n=3.

Smooth muscle physiology in HSV explants that were treated with MK2i-polyplexes also show significantly more relaxation than HSV explants that were exposed to MK2i alone. Furthermore, certain polyplexes achieved the same level of relaxation enhancement as MK2i alone at a 10-fold lower dose. For instance, as shown in FIG. 4, both polyplexes comprising about 10 µM of MK2i and 100 µM doses of non-polyplexed MK2i showed about 15%-20% relaxation.

Figure 5:
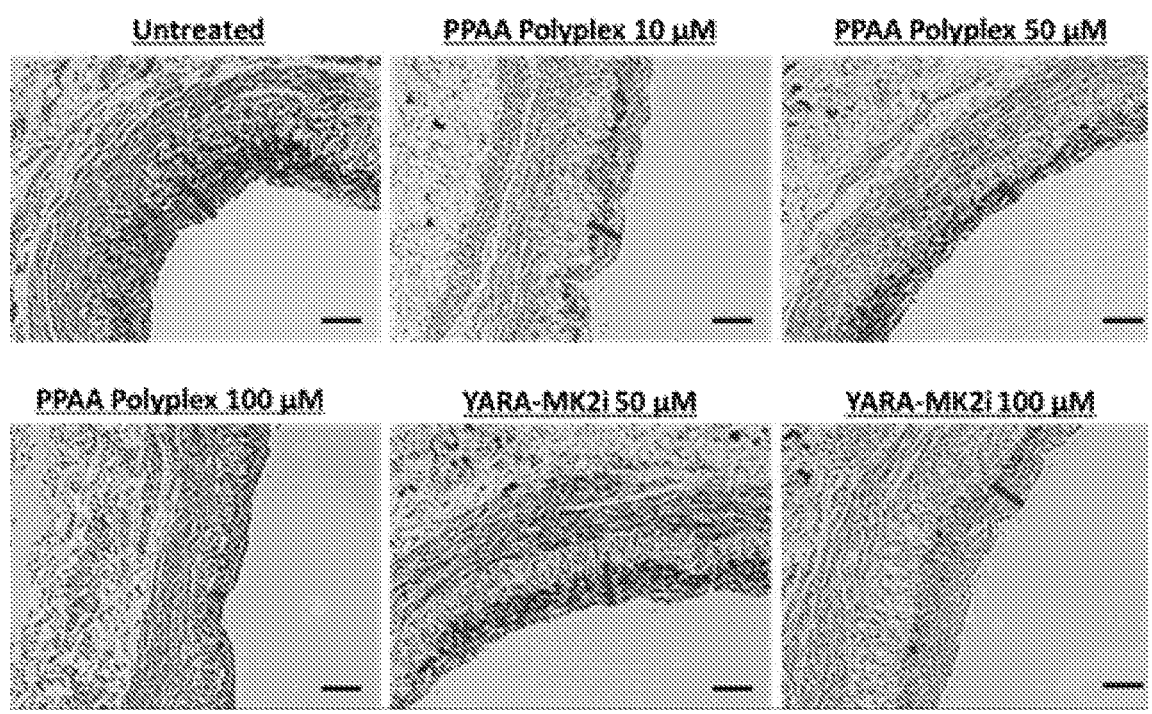
FIG. 5 shows histological sections of HSV samples that were untreated, treated with MK2i alone, or treated with various embodiments of MK2i polyplexes. Dark lines demarcate intimal thickness. Scale bars are 100 μm in length.

FIG. 5 shows how the MK2i polyplexes demonstrate an enhanced ability to prevent intimal hyperplasia compared to MK2i alone, showing decreased intimal thickness. After 14 days of organ culture, the HSV sections that were treated with MK2i polyplexes had an intimal thickness of 63.8±8 nm, whereas HSV sections treated with non-polyplexed MK2i had an intimal thickness of 89.5±13.9 nm at 10 µM (p=0.05). The intimal/medial ratio for MK2i polyplex treated HSV is 0.459±0.058, whereas HSV sections treated with MK2i alone had an intimal/medial ratio of 0.736±0.132 at 10 µM (p=0.03) after 14 days of organ culture.

Example 2

Synthesis and Physicochemical Characterization of MK2i-NPs

Figure 6:
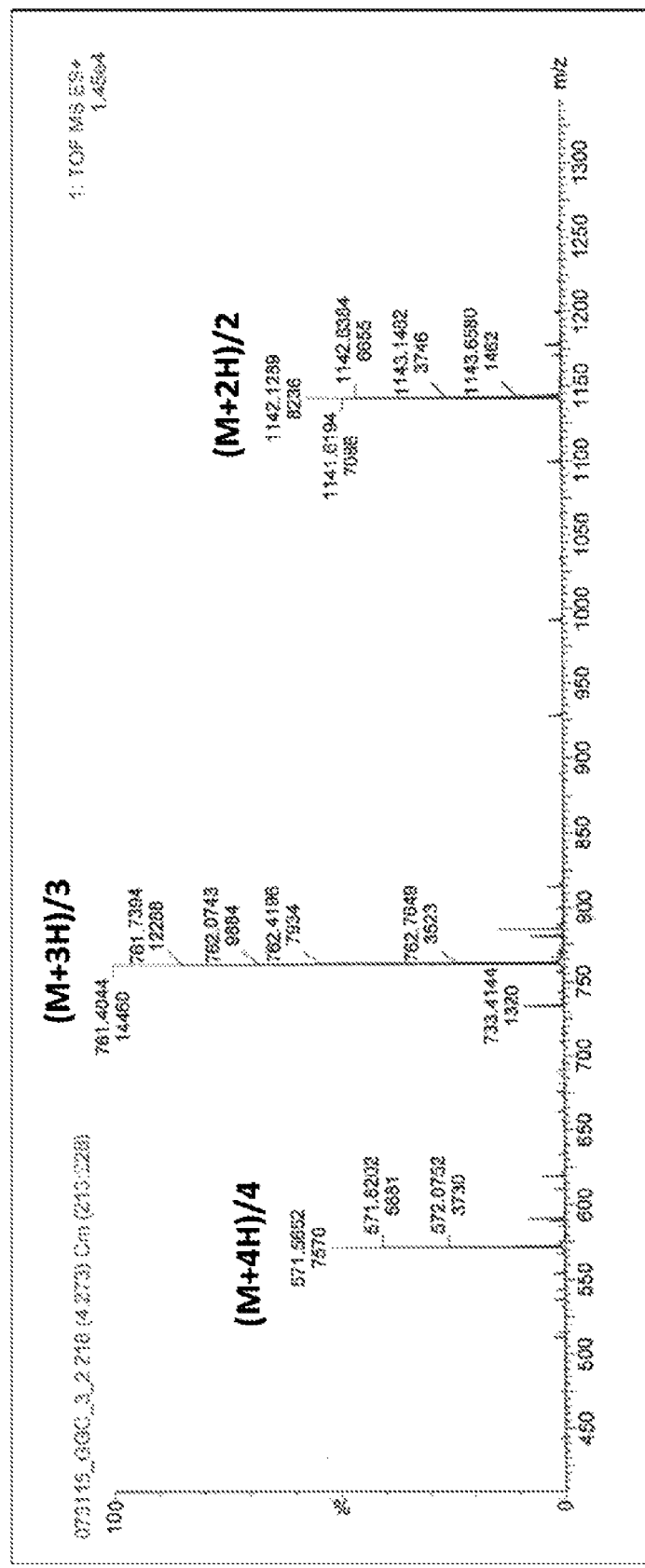
FIG. 6 provides an electrospray-ionization mass spectrometry (ESI-MS) mass spectrum for the HPLC-purified CPP-MK2i fusion peptide (SEQ. ID. NO. 1: YARAAAR-QARA-KALARQLGVAA). The molecular weight is 2283.67 g/mol. This mass spectrum shows three major peaks, each corresponding to the fragmentation of the full peptide sequence.
Figure 7:
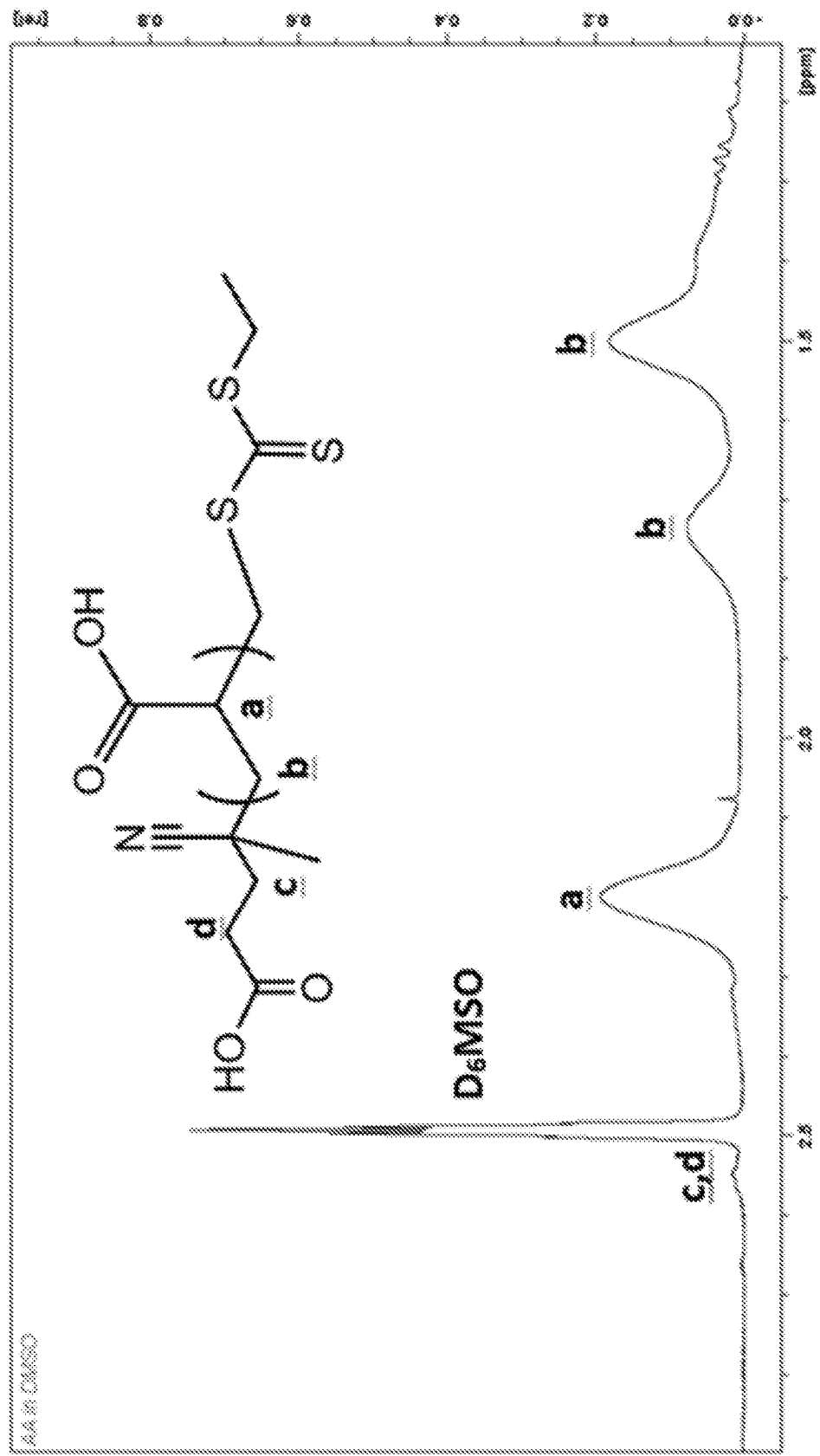
FIG. 7 is a $^1$H NMR spectrum of poly(acrylic acid) (PAA) in $D_6$MSO. Molecular weight was determined by comparing the area of peaks associated with the chain transfer agent (i.e. peaks c,d for PAA and peak b for PPAA) to peaks associated acrylic acid/propylacrylic acid (i.e. peak a for PAA and peak c for PPAA): PAA degree of polymerization=106, PPAA degree of polymerization=190.
Figure 8:
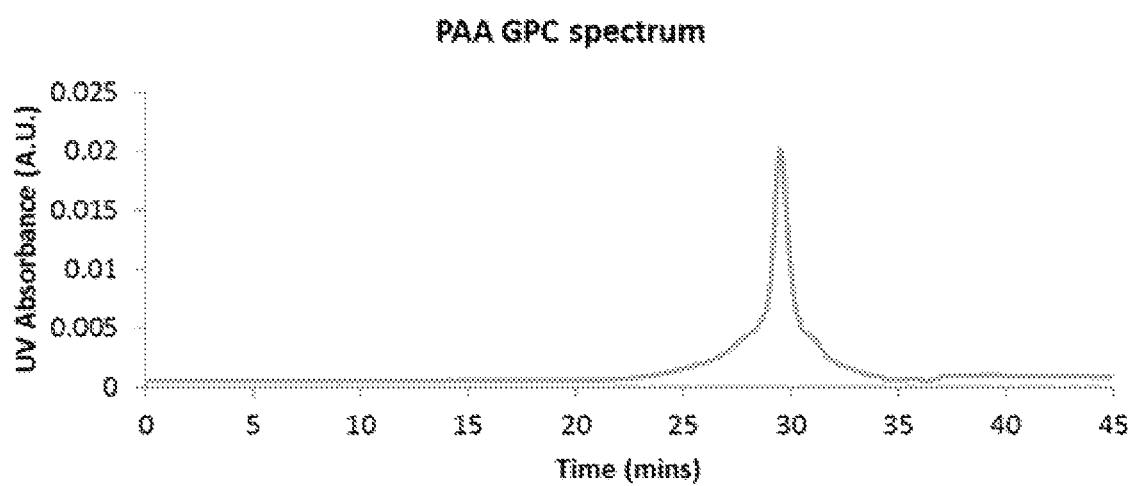
FIG. 8 is a GPC chromatogram of poly(acrylic acid) (PAA): $M_n$=10830 (g/mol), PDI=1.27, dη/dC=0.09 (mL/g). The trace shows UV absorbance at the characteristic absorption peak of the trithiocarbonate moiety (310 nm) present in the 4-cyano-4-(ethylsulfanylthiocarbonyl) sulfanylpentanoic acid (ECT) chain transfer agent utilized in the polymerization.
Figure 9:
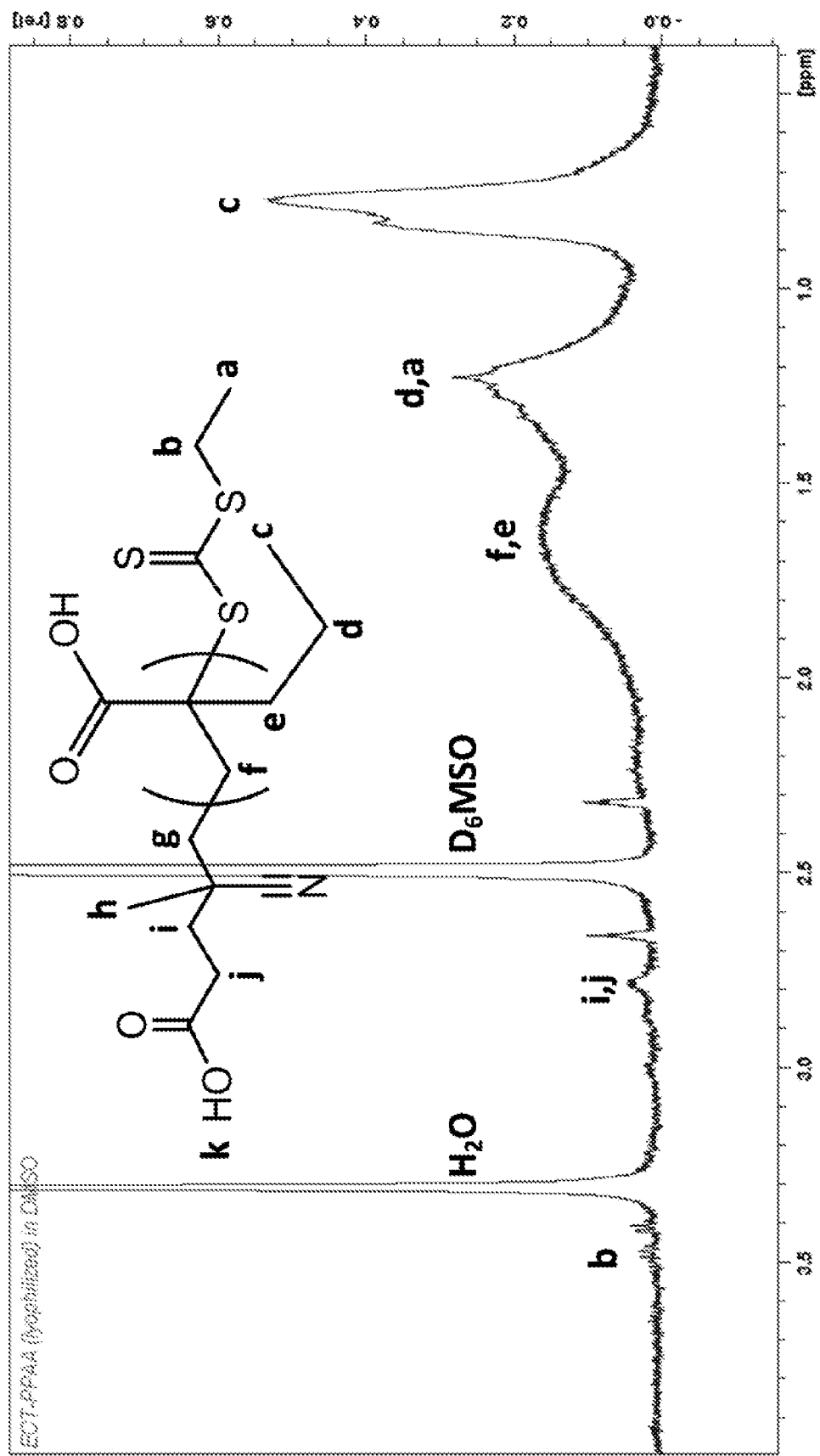
FIG. 9 provides a $^1$H NMR spectrum of poly(propylacrylic acid) (PPAA) homopolymer in $D_6$MSO. Molecular weight was determined by comparing the area of peaks associated with the chain transfer agent (i.e. peaks c,d for PAA and peak b for PPAA) to peaks associated acrylic acid/propylacrylic acid (i.e. peak a for PAA and peak c for PPAA): PAA degree of polymerization=106 PPAA degree of polymerization=190, MW=21,950 g/mol.
Figure 10:
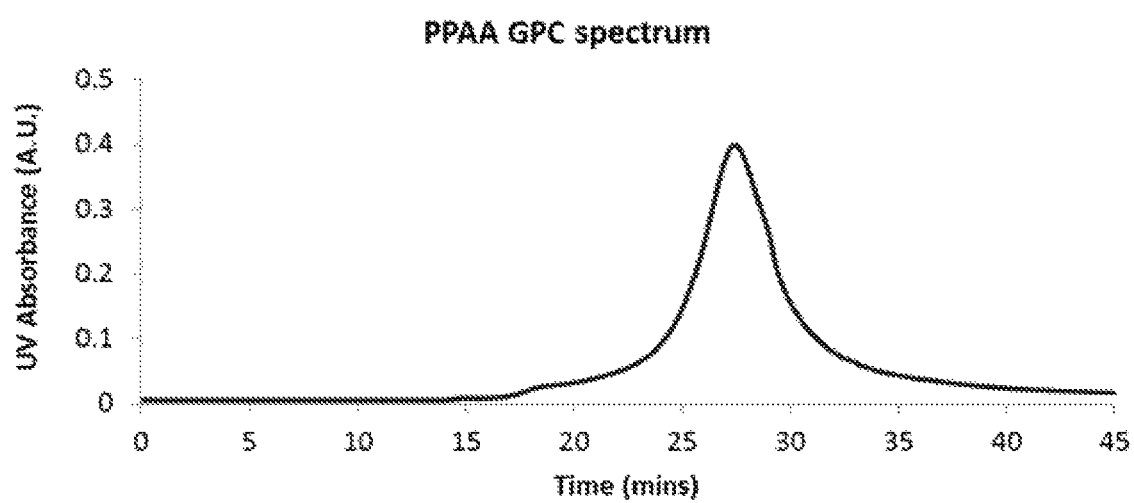
FIG. 10 is a GPC chromatogram of poly(propylacrylic acid) (PPAA): $M_n$=22010 (g/mol), PDI=1.471, dη/dC=0.087 (mL/g) polymers in DMF. The trace shows UV absorbance at the characteristic absorption peak of the trithiocarbonate moiety (310 nm) present in the 4-cyano-4-(ethylsulfanylthiocarbonyl) sulfanylvpentanoic acid (ECT) chain transfer agent utilized in the polymerization.
Figures 11, 12:
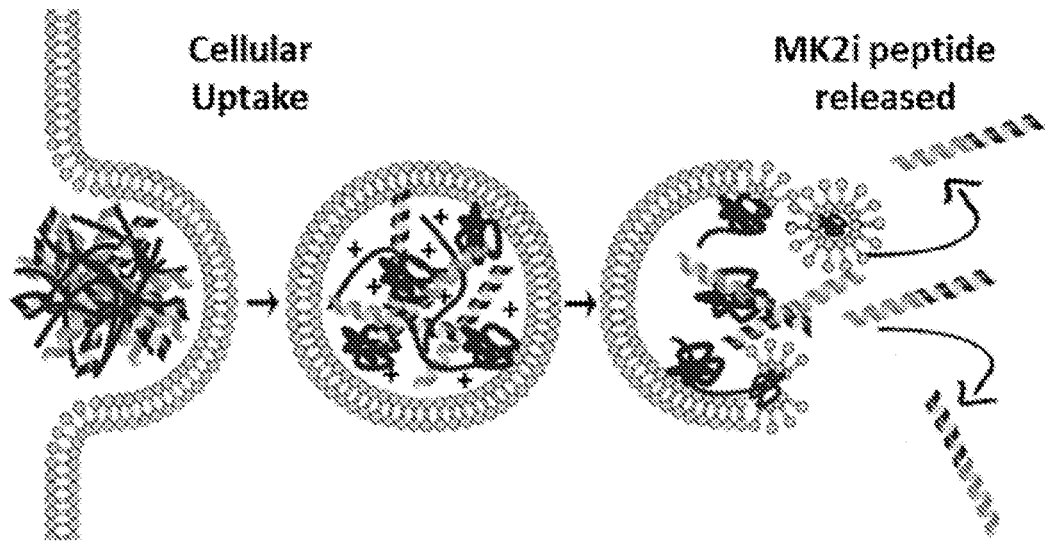
FIG. 11 provides an illustration that relates the design and functional features of MK2 polyplexes, wherein the MK2iNPs are optimized to mediate endosome escape and to release peptide therapeutics intracellularly.
FIG. 12 provides a treatment comparison summary: MK2i-NPs are formulated with an endosomolytic PPAA polymer, whereas NE-MK2i-NPs are formulated with a PAA polymer, which is structurally similar to PPAA but not endosomolytic due to its lower pKa. Both the MK2i-NPs and NE-MK2i-NPs are made with the MK2i peptide with the sequence shown (top row=modified TAT mimetic cell penetrating peptide sequence, bottom row=MK2 inhibitory sequence).

The MK2i peptide (YARAAARQARAKALARQL-GVAA) was synthesized via solid phase synthesis and purity is verified through electrospray-ionization mass spectrometry (FIG. 6). Reversible addition fragmentation chain transfer (RAFT) polymerization was utilized to synthesize poly (acrylic acid) (PAA) [$M_n$=10,830 (GPC), $M_n$=7,640 ($H^1$ NMR), PDI=1.27 (GPC) (FIG. 7 and FIG. 8)] and poly (propylacrylic acid) (PPAA) [$M_n$=22,010 (GPC), $M_n$=21,950 ($H^1$ NMR), PDI=1.47 (GPC) (FIG. 9 and FIG. 10)]. Nano-polyplexes (NPs) were formed by simple mixing of the PAA or PPAA homopolymers with the MK2i peptide in PBS at pH 8.0, which as between the pKa values of the primary amines present on the MK2i peptide and the carboxylic acid moieties in the PPAA polymer. PAA is utilized as a vector control, as it is an anionic polymer with structural similarity to PPAA but lacks pH-responsivity in a physiologically relevant range due to its lower pKa (pKa~4.3).

Figure 13:
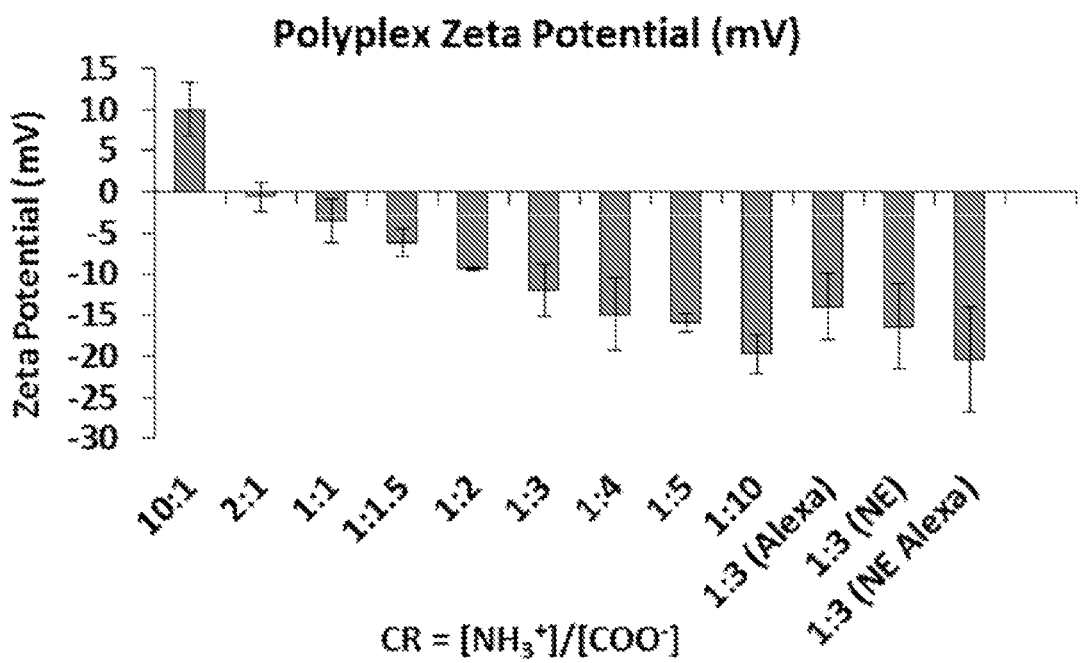
FIG. 13 shows the zeta potential(s) of polyplexes prepared at different charge ratios ($[NH_3^+]/[COO^-]$). For imaging and uptake studies, NPs were formulated from MK2i peptide labeled with an Alexa®-488 fluorophore. NE-NPs are formulated with a non-endosomolytic (NE) PAA polymer. Values shown are an average of at least three independent measurements.

To determine optimal polyplex formulation conditions, a library of MK2i-NPs was prepared at a range of charge ratios [i.e. CR=([$NH_3^+$]$_{MK2i}$:[$COO^-$]$_{PPAA}$)], and the size distribution and particle surface charge were characterized through dynamic light scattering (DLS) and $\zeta$-potential analysis, respectively. MK2i-NP $\zeta$-potential was directly proportional to the CR, with an apparent isoelectric point at CR~2:1 (FIG. 13). The CR also significantly affected MK2i-NP size, with only a narrow range of CRs yielding a unimodal size distribution (i.e. CR=1:2 and 1:3, Table 1).

TABLE 1

Size summary of MK2i-NPs prepared at different charge ratios ([$NH_3^+$]/[$COO^-$]) as determined by DLS analysis.

| NH2:COOH | Z-ave diameter (nm) | PDI |
|---|---|---|
| 10:1 | 10.32 ± 2.63* | 0.314 |
| 2:1 | 52.1 ± 46.86* | 0.297 |

TABLE 1-continued

Size summary of MK2i-NPs prepared at different charge ratios ([NH$_3^+$]/[COO$^-$]) as determined by DLS analysis.

| NH2:COOH | Z-ave diameter (nm) | PDI |
|---|---|---|
| 1:1 | 970.6 ± 662.4 | 0.41 |
| 1:1.5 | 465.1 ± 138.4* | 0.5465 |
| 1:2 | 474.2 ± 32.59 | 0.239 |
| 1:3 | 118.8 ± 26.76 | 0.271 |
| 1:4 | 607.4 ± 285.2* | 0.662 |
| 1:5 | 213.0 ± 67.95* | 0.407 |
| 1:10 | 21.57 ± 9.89* | 0.355 |
| 1:3 (FAM) | 158 ± 56.67 | 0.308 |
| 1:3 (AA) | 113.7 ± 14.47 | 0.577 |
| 1:3 (AA-FAM) | 236.5 ± 69.74 | 0.522 |

Asterisks (*) indicate multimodal size distributions (multiple peaks present).
1:3 (Alexa) polyplexes were formulated with an Alexa488-conjugated MK2i peptide to use in cellular uptake studies. 1:3 (NE) polyplexes were formulated with a non-endosomolytic (NE) poly(acrylic acid) polymer that does not exhibit a pH-dependent membrane disruptive activity in the endosomal pH range as a vehicle control.

Figure 14:
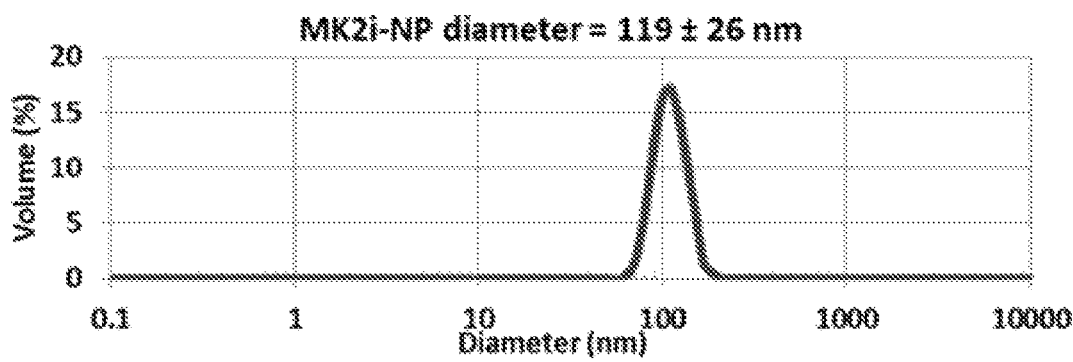
FIG. 14 provides a dynamic light scattering (DLS) analysis of MK2i-NPs with a diameter of 119±26 nm.
Figure 15:
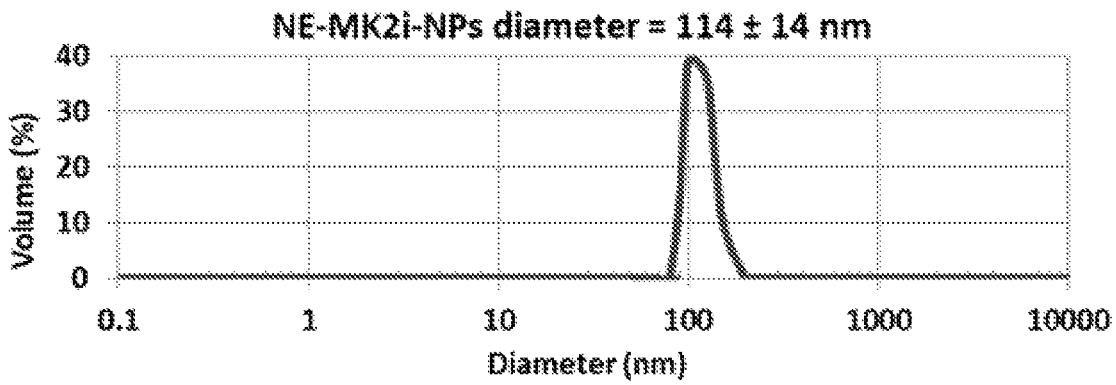
FIG. 15 provides a dynamic light scattering analysis of NE-MK2i-NPs with a diameter of 114±14 nm.
Figure 16:
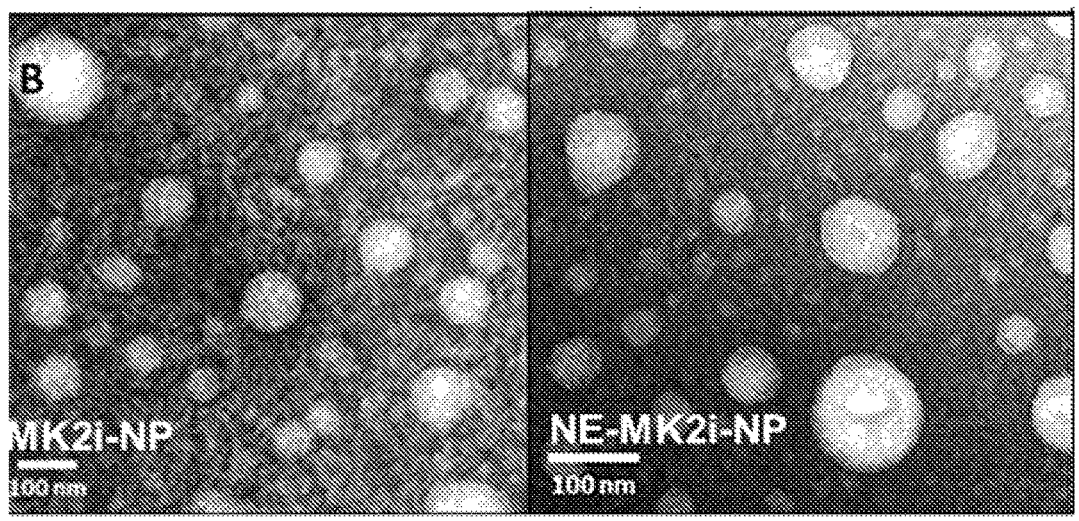
FIG. 16 provides representative transmission electron microscope (TEM) images of uranyl acetate counterstained MK2i-NPs and NE-MK2i-NPs. Scale bars are 100 nm in length.

A CR of 1:3 was chosen in this example as this ratio consistently yields a unimodal size distribution with minimal particle size and polydispersity ($d_h$=119±28 nm, $\zeta$=−11.9±3.2 mV). Non-endosomolytic MK2i nano-polyplexes (NE-MK2i-NPs) were formulated with PAA as a vehicle control for biological studies. NE-MK2i-NPs prepared at CR=1:3 with PAA had size and $\zeta$-potential statistically equivalent to the endosomolytic MK2i-NPs ($d_h$=114±38 nm, $\zeta$=−16.4±5.1 mV). Fluorescent MK2i-NPs and NE-MK2i-NPs were prepared with an Alexa®-488 conjugated MK2i peptide at a CR of 1:3 in order to enable intracellular tracking and yielded similar size and charge to the unlabeled NPs. NPs prepared at a CR=1:3 were further characterized through TEM imaging (FIG. 14, FIG. 15, FIG. 16), which was in agreement with DLS results.

Figure 17:
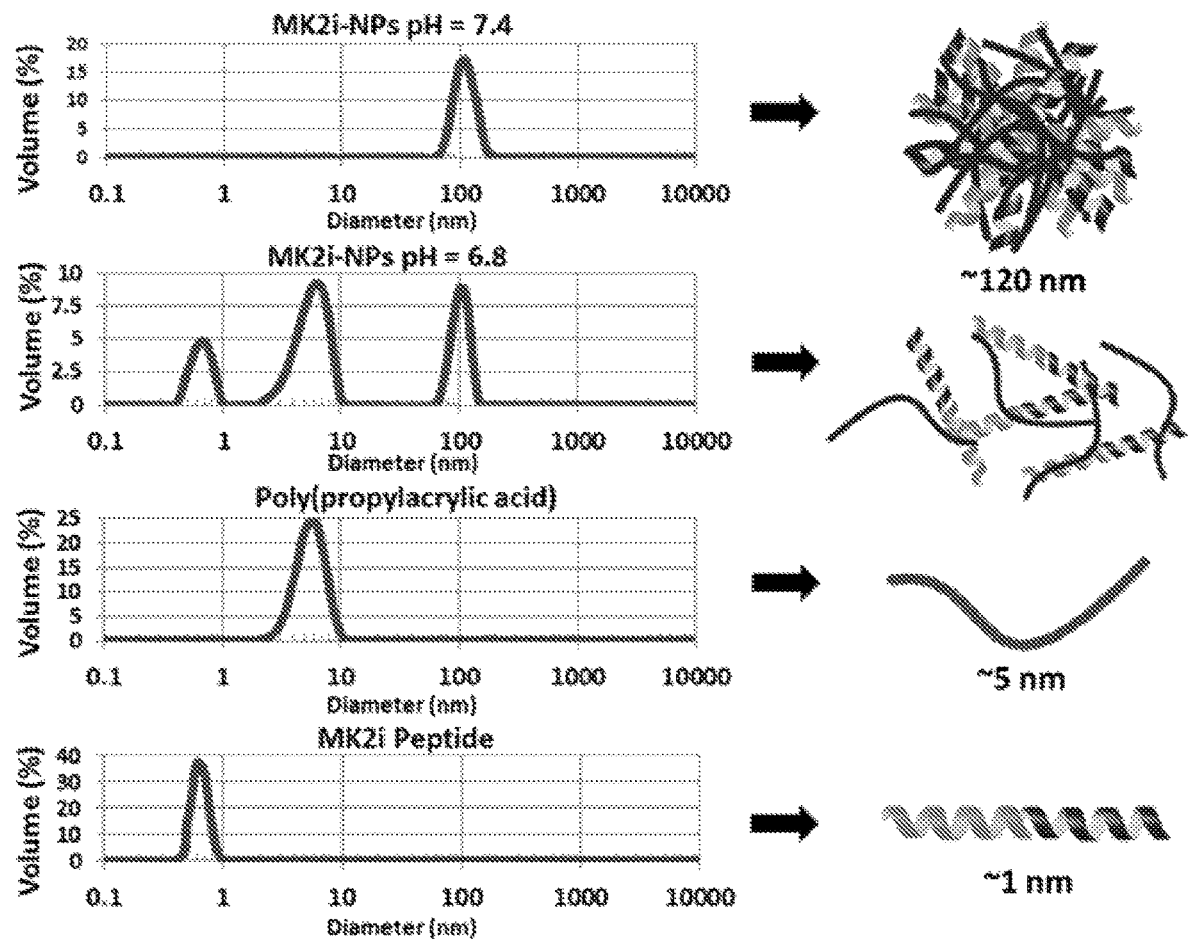
FIG. 17 shows that MK2i-NPs undergo pH-triggered disassembly in the endosomal pH range, as demonstrated by DLS analysis.

MK2i-NP unpackaging under endolysosomal conditions was assessed using DLS at a range of pHs and reveals that the MK2i-NPs dissociates as the pH is lowered from extracellular pH toward the pKa of the carboxylic acids (pH~6.7) on PPAA, which also correlates to early endosomal conditions (FIG. 17). Without being bound by theory, at the lower pH the PPAA polymer becomes protonated/deionized, and the net positive charge on the peptide causes electrostatic repulsion and disassembly of the MK2i-NPs. NP disassembly under early endosome-like conditions reduces the possibility that peptide bioactivity and/or PPAA endosomal membrane disruptive function is sterically hindered by polymer-peptide interactions.

Example 3

MK2i-NP Cell Internalization, Endosome Escape, and Intracellular Retention

Figure 18:
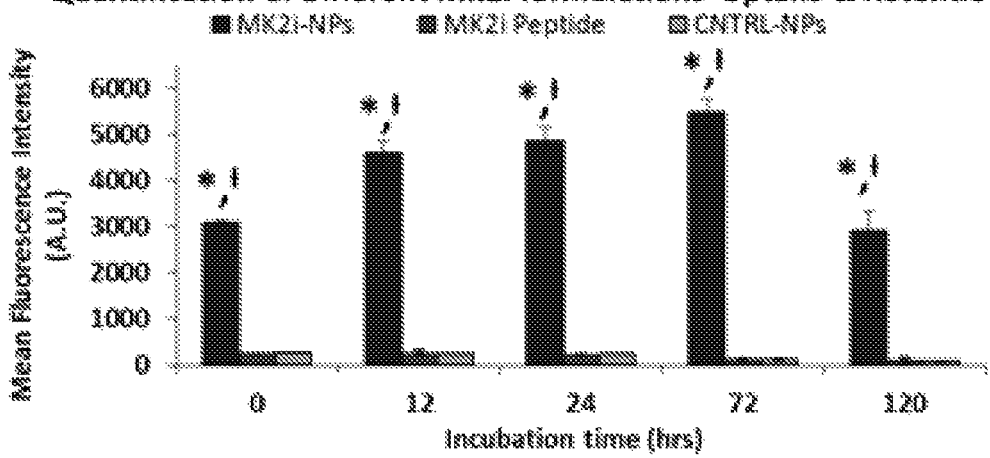
FIG. 18 provides a graph showing quantification of cellular uptake and retention of fluorescently labeled MK2i, MK2i-NPs, and NE-MK2i-NPs. *$p<0.001$ vs MK2i, $^†p<0.001$ vs. NE-MK2i-NPs, n=3. MK2i-NP formulations increase cellular uptake, extend intracellular retention, and reduce endo-lysosomal colocalization of MK2i.
Figure 19:
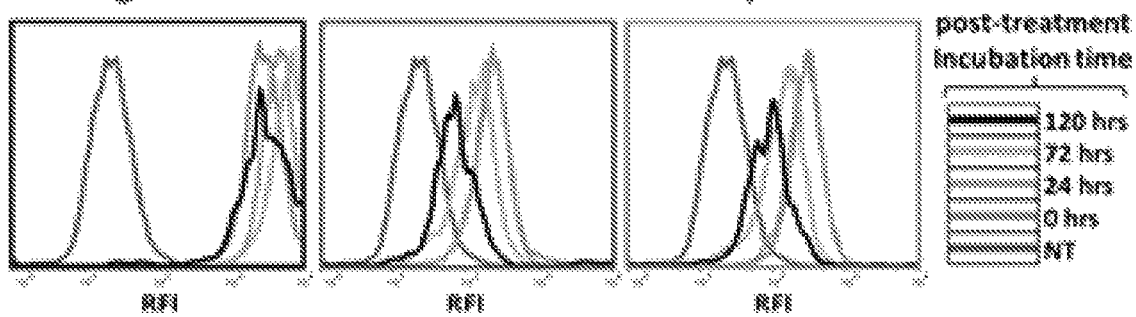
FIG. 19 presents representative flow histograms, which demonstrate increased cellular uptake and longer retention of fluorescently-labeled MK2i peptide delivered via MK2i-NPs.

Quantity of MK2i-NP uptake and intracellular retention over time were assessed through flow cytometry of HCAVSMCs treated for two hours, washed, and maintained in fresh medium for 5 days. Over an order of magnitude increase in peptide uptake is measured in MK2i-NP treated cells compared to NE-MK2i-NPs and MK2i. (FIG. 18) Because NE-MK2i-NPs uptake was equivalent to the free peptide, these data indicate that differences in cell internalization were due to NP composition and independent of particle morphology and charge. Additionally, HCAVSMCs treated with MK2i-NPs demonstrate more stable intracellular retention of the peptide, whereas NE-MK2i-NP and MK2i treated cells more rapidly lost intracellular peptide, likely due to peptide degradation in the endolysosomal pathway or trafficking for exocytosis out of the cell (FIG. 19). MK2i-NPs showed an increase in fluorescence over the first 72 hours of incubation following treatment/washing. This effect is not due to delayed internalization of MK2i-NPs bound to the outer membrane of the cells. It is hypothesized that this increase in fluorescence is due to an Alexa®-488 self-quenching mechanism that diminishes during gradual intracellular unpackaging of MK2i from the NPs.

Figure 20:
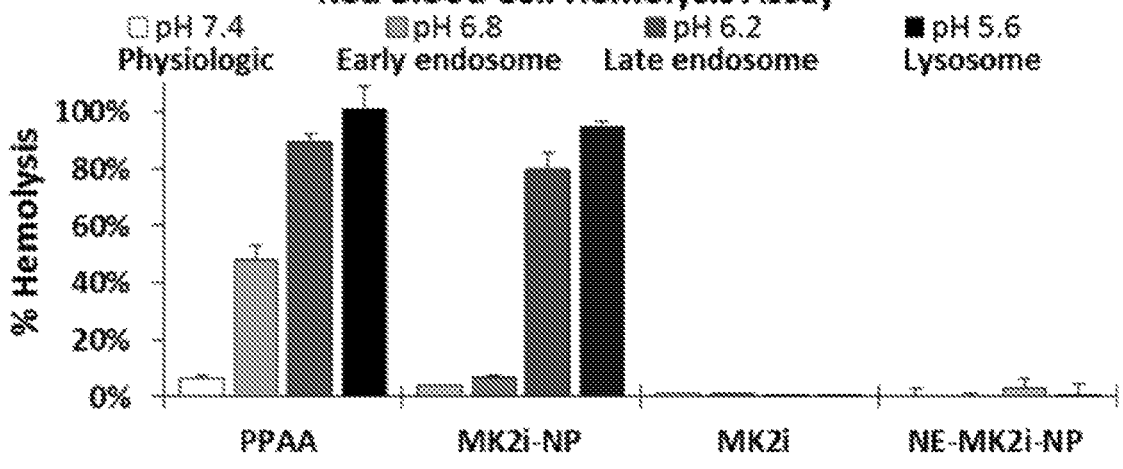
FIG. 20 shows the results of a red blood cell hemolysis assay, wherein MK2i-NPs have similar pH-dependent membrane disruptive activity to the PPAA polymer but NE-MK2i-NPs and the MK2i peptide alone do not.
Figure 21:
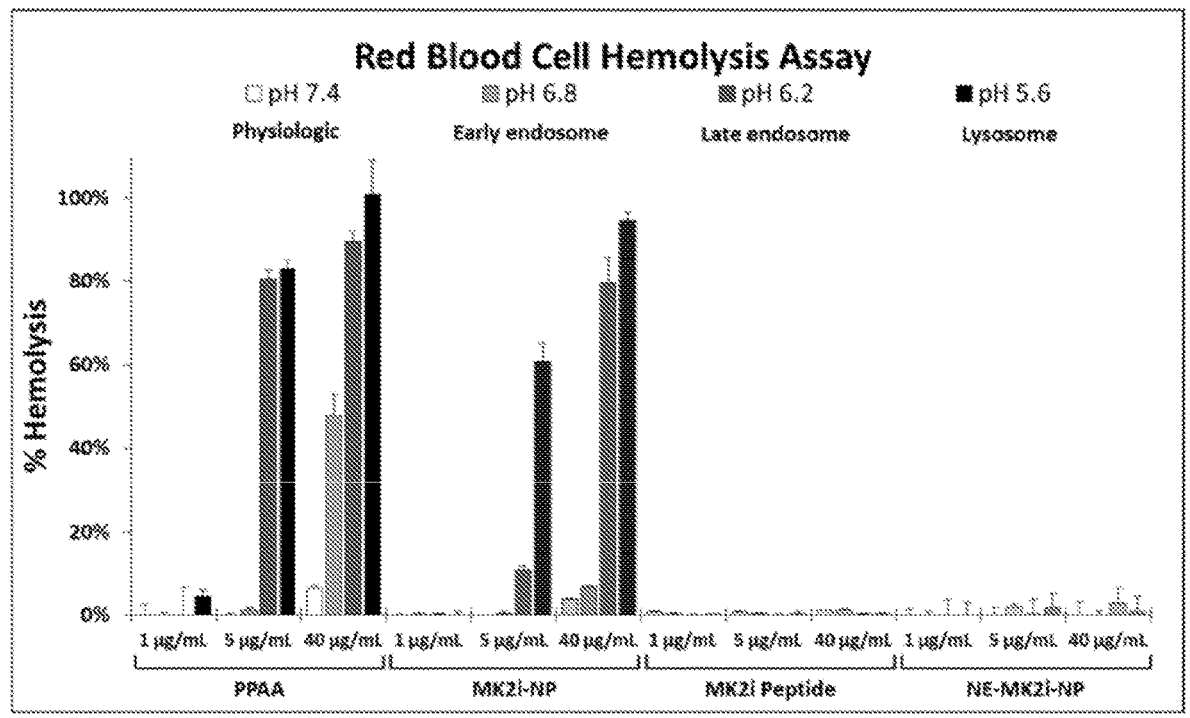
FIG. 21 provides a full red blood cell hemolysis data set. A red blood cell hemolysis assay shows that MK2i-NPs have similar pH-dependent and dose-dependent membrane disruptive activity to the PPAA polymer, but NE-MK2i-NPs and the MK2i peptide alone do not.

A red blood cell hemolysis assay was utilized to assess pH-dependent membrane disruptive activity of MK2i-NPs as an indicator of endosomal escape function. PPAA disrupted erythrocyte membranes at pHs at or below its pKa (~6.7) (FIG. 20). At extracellular (7.4) and early endosomal (6.8) pH, MK2i-NPs showed little membrane disruptive activity. However, at pH representative of late endosomes (6.2) and lysosomes (5.6), a significant increase in hemolysis was observed. The hemolytic behavior of the MK2i-NPs at late endosome/lysosomal pH was directly proportional to polymer concentration (FIG. 21), with >90% erythrocyte lysis occurring at 40 μg/mL MK2i-NPs at pH 5.6. MK2i-NPs retain the inherent membrane disruptive activity of the PPAA polymer, although formulation into NPs slightly masked the membrane disruptive activity relative to free PPAA at pH 6.8. Neither the MK2i peptide alone nor the non-endosomolytic NE-MK2i-NP formulation displayed membrane disruptive activity in the endolysosomal pH range.

Figure 22:
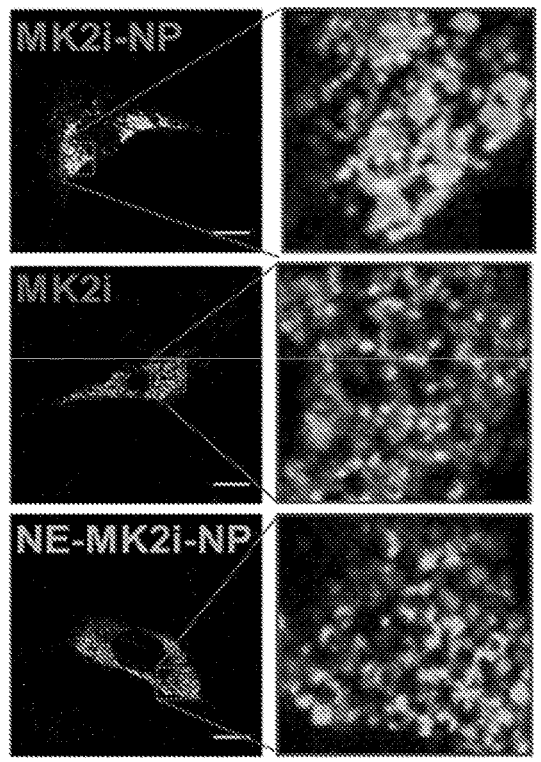
FIG. 22 presents representative confocal microscopy images of Alexa Fluor®-488 labeled MK2i colocalization with LysoTracker® red 24 hours after treatment. The images demonstrate that MK2i-NPs have reduced endo-lysosomal colocalization. Scale bars=20 μm.
Figure 23:
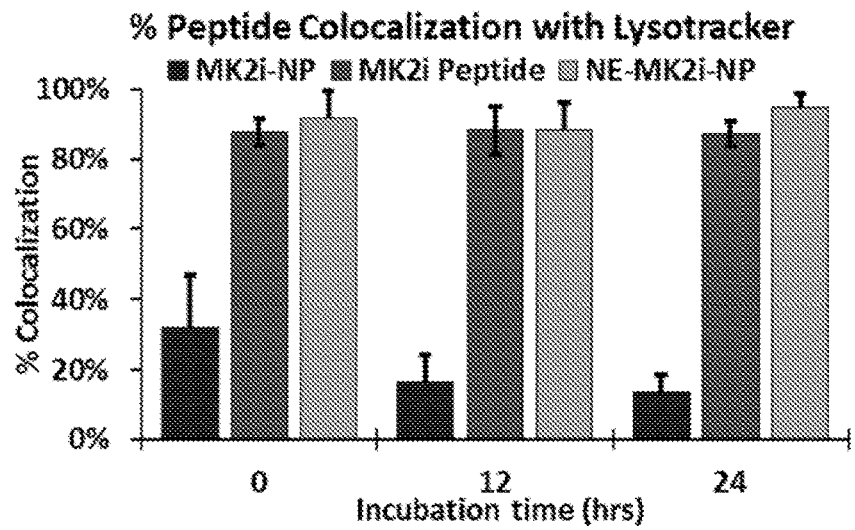
FIG. 23 provides a graph showing quantification of MK2i peptide colocalization with the endo/lysosomal dye LysoTracker® red at 0, 12, and 24 hours after treatment, $*p<0.01$ vs MK2i, $^{†}p<0.01$ vs. NE-MK2i-NPs, n≥3 independent images.
Figure 24:
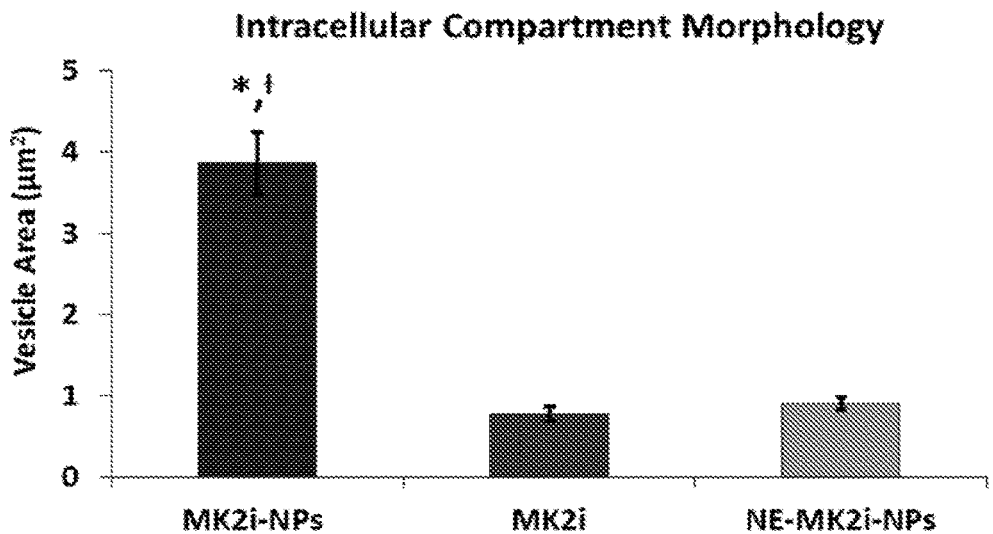
FIG. 24 displays the average size of intracellular compartments containing MK2i 24 hours after treatment with different peptide formulations. The compartment area was quantified with ImageJ software. $*p<0.001$ vs MK2i, $^{†}p<0.001$ vs. NE-MK2i-NPs, n=50 vesicles from at least 3 different images.

MK2i-NP's endosomal escape was imaged and quantified in vitro in human coronary artery vascular smooth muscle cells (HCAVSMCs) (FIG. 22). Nearly all (~90%) MK2i delivered as free peptide or via NE-MK2i-NPs co-localized with the LysoTracker® dye. However, MK2i-NP formulation significantly reduced MK2i endolysosomal colocalization. Longitudinal quantification of MK2i/LysoTracker® colocalization following a two-hour treatment and wash revealed significantly reduced MK2i/LysoTracker® colocalization for the MK2i-NP formulations at all time points, and colocalization of MK2i delivered via the NP formulation with LysoTracker® decreased over time (FIG. 23). Quantification of compartment size revealed that NE-MK2i-NP or MK2i treated cells showed MK2i localization within smaller vesicles representative of endosomes, whereas MK2i delivered via MK2i-NPs was found within larger compartments which may be representative of leaky, swollen endosomes macropinosomes, or cytosolic regions (FIG. 24).

Example 4

Inhibition of Intimal Hyperplasia in Human Saphenous Vein

Figure 25:
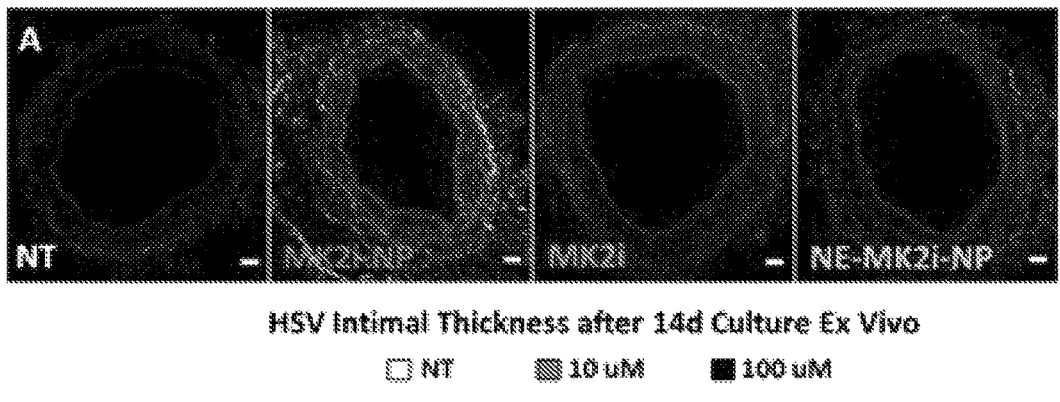
FIG. 25 shows that MK2i-NP formulation increased HSV delivery of Alexa® 568-MK2i.
Figure 26:
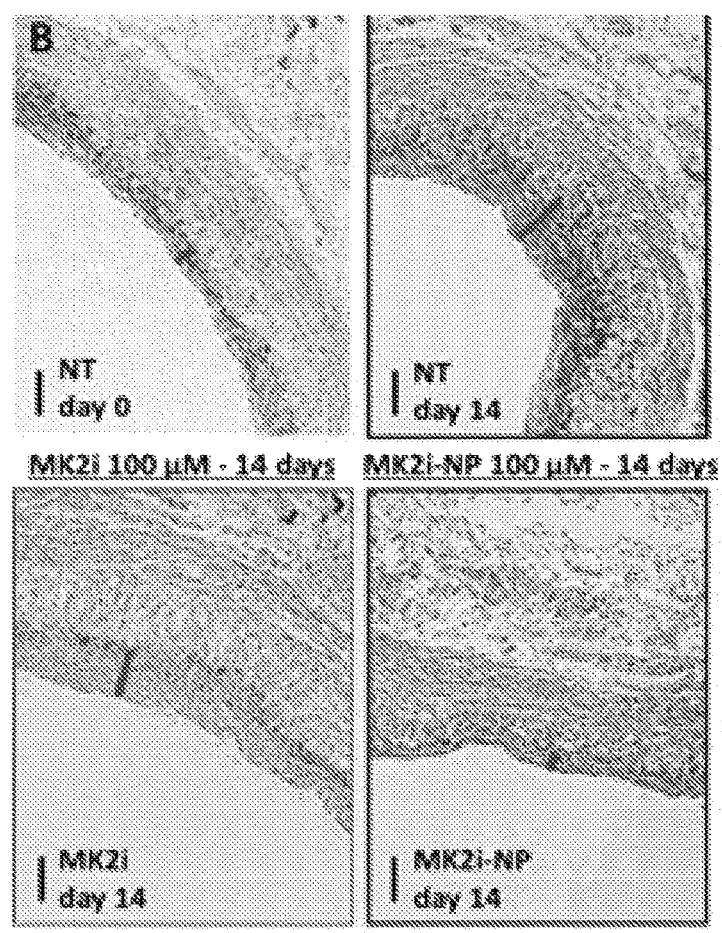
FIG. 26 presents representative microscopy images of Verhoeff Van-Gieson (VVG) stained HSV sections that were treated for two hours and maintained in organ culture for 14 days, showing that MK2i-NPs effectively blocked neointima formation. Red bars demarcate intimal thickness. Scale bars are 100 μm in length.
Figure 27:
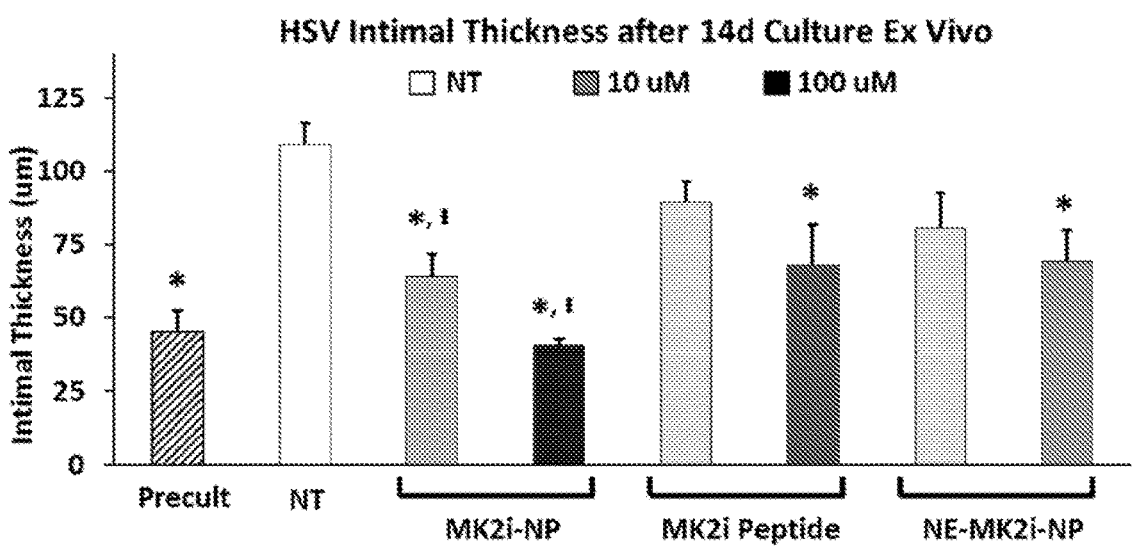
FIG. 27 provides quantification of intimal thickness from VVG stained histological sections; measurements are average of 6-12 radially parallel measurements from at least three vein rings from separate donors. $*p<0.01$ vs. NT, $^{†}p<0.05$ vs. MK2i at the same concentration.
Figure 28:
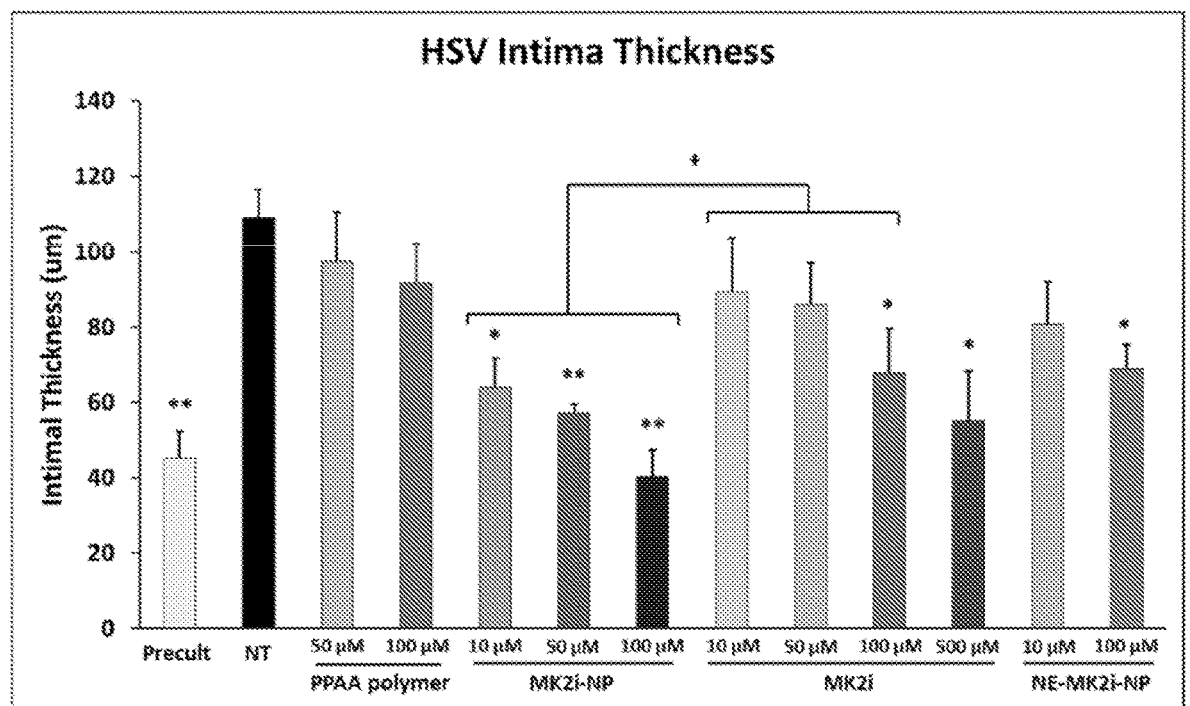
FIG. 28 presents intimal thickness measurements of HSV explants treated for two hours and then maintained in organ culture for 14 days, n≥3 from at least 3 different donors. $*p≤0.01$ compared to no treatment control (NT), $**p≤0.001$ compared to NT, $^{†}p≤0.05$.
Figure 29:
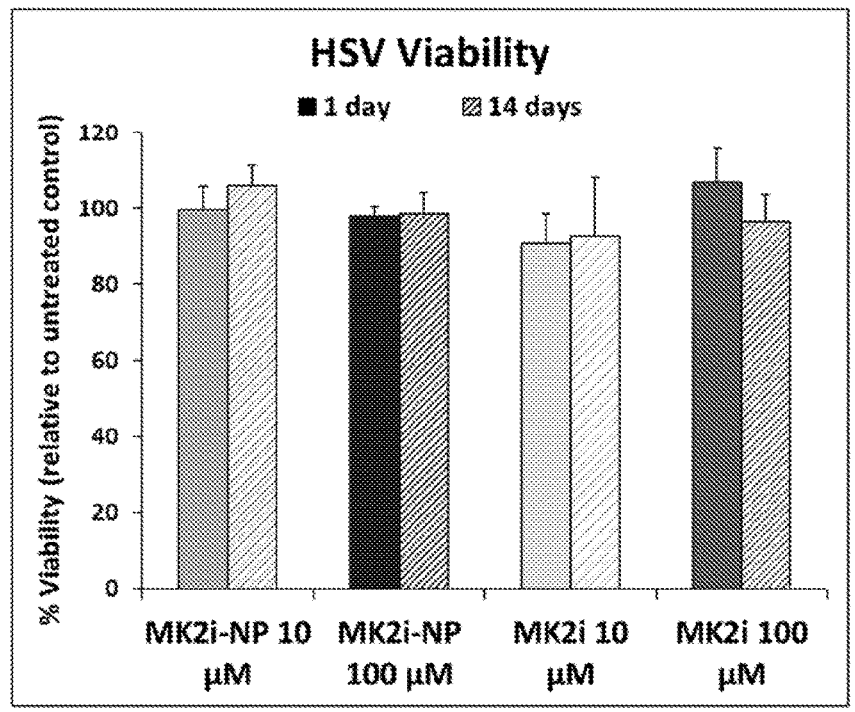
FIG. 29 shows cell viability in HSV rings treated for 2 hours and maintained in organ culture for 1 or 14 days, as assessed through an MTT assay. n≥3 vein rings from at least 3 separate donors.

In an ex vivo organ culture model of vein IH, human saphenous vein (HSV) rings were treated for two hours and subsequently maintained in high serum conditions to accelerate neointima formation. An Alexa*r(−568 conjugated MK2i peptide was used to assess MK2i delivery to the vessel wall, and, similar to the in vitro result, MK2i-NPs consistently demonstrated enhanced uptake relative to free MK2i (FIG. 25). After 14 days in culture, Verhoeff-Van Gieson (VVG) staining of the elastic laminae was performed on tissue sections (FIG. 26). Quantification of intimal thickness from multiple donors revealed that MK2i-NPs significantly inhibited IH in a dose-dependent fashion and at an order of magnitude lower peptide dose than free MK2i (FIG. 27, full data set in FIG. 28). MK2i-NP therapy at 100 μM MK2i was the only treatment that fully abrogated IH, yielding intimal thickness statistically equivalent to control tissues prepared for histology immediately after harvest (p=0.49). MTT assays were performed 1 and 14 days post-treatment and verify that organ culture results were not affected by tissue cytotoxicity (FIG. 29).

Example 5

Mechanistic Elucidation of MK2i-NP Bioactivity

Figure 30:
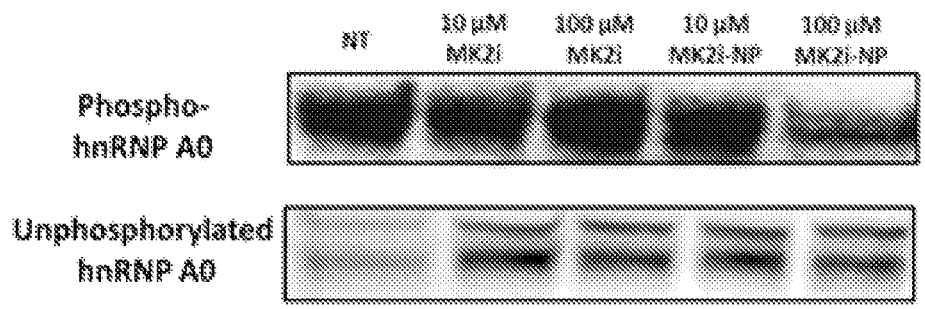
FIG. 30 provides the results of a Western blot analysis, which show that MK2i-NPs reduced HnRNP A0 phosphorylation in human saphenous vein following 2 hours of treatment, $*p<0.05$ vs. NT.
Figure 31:
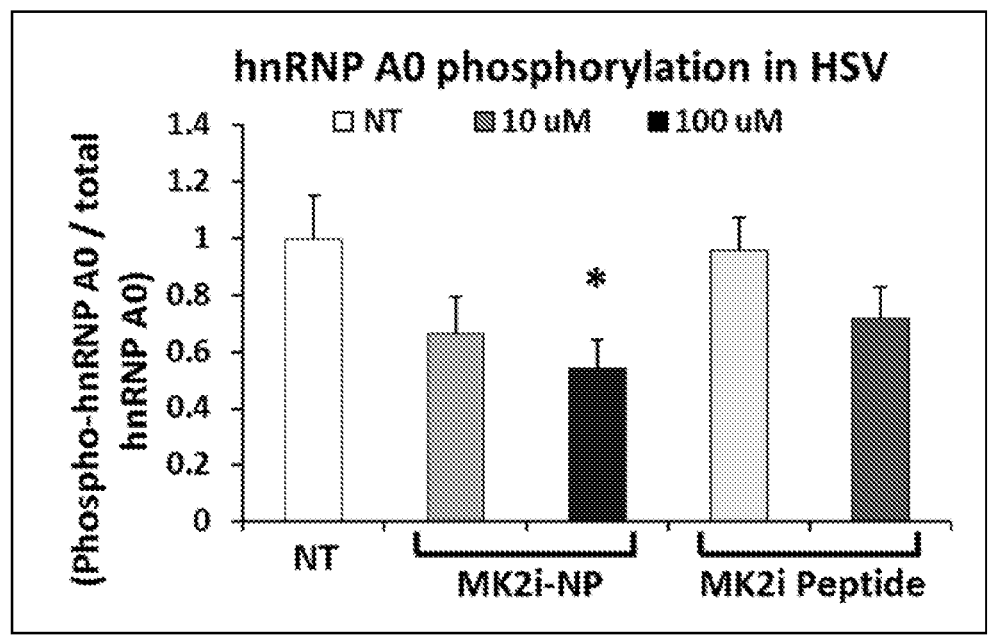
FIG. 31 provides the further results of the Western blot analysis of FIG. 30, wherein the MK2i-NPs reduced HnRNP A0 phosphorylation in human saphenous vein following 2 hours of treatment, $*p<0.05$ vs. NT.
Figure 32:
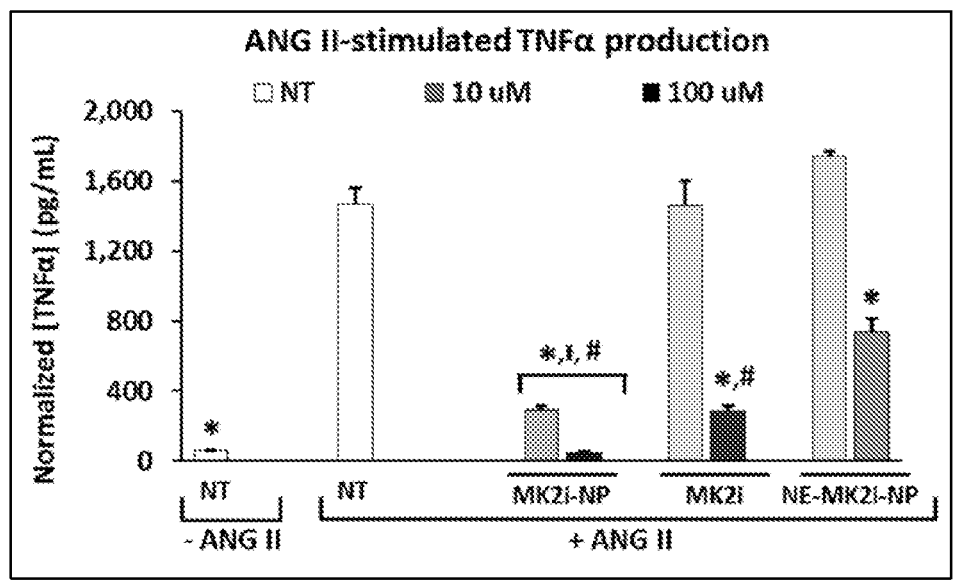
FIG. 32 shows that MK2i-NP treatment blocked TNFα production in HCAVSMCs stimulated with ANG II. All data is normalized to cell number. "NT" means no treatment, $*p<0.05$ vs. NT+TNFα, $^{†}p<0.05$ vs. MK2i at same concentration $^{\#}p<0.05$ vs. NE-MK2i-NPs at same concentration. MK2i-NP formulation enhances MK2i bioactivity in HCAVSMCs.
Figure 33:
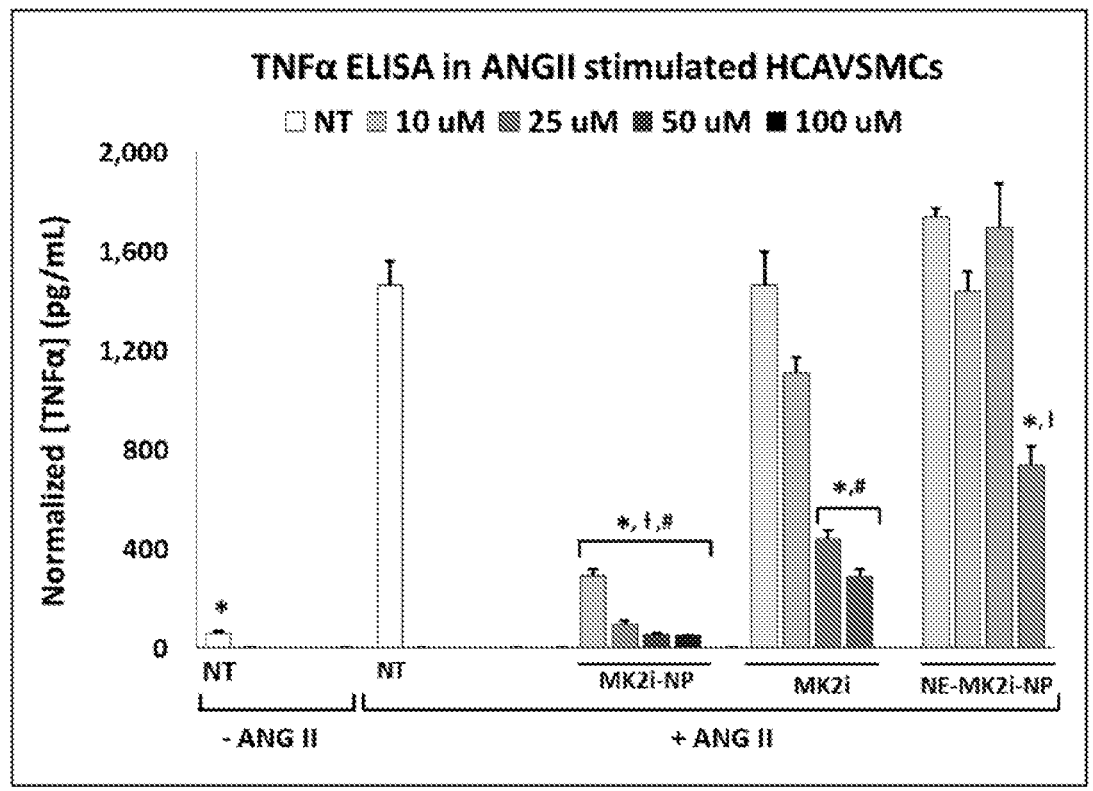
FIG. 33 shows TNFα production in HCAVSMCs stimulated with ANG II for 6 hours, treated for two hours with MK2i-NPs, NE-MK2i-NPs, or the MK2i peptide alone and cultured for 24 hours in fresh media. All data is normalized to cell number. "NT" means no treatment. $*p<0.05$ compared to NT+TNFα group, $^{†}p<0.05$ compared to MK2i at the same concentration, $^{\#}p<0.05$ compared to NE-MK2i-NPs at the same concentration, n=4.
Figure 34:
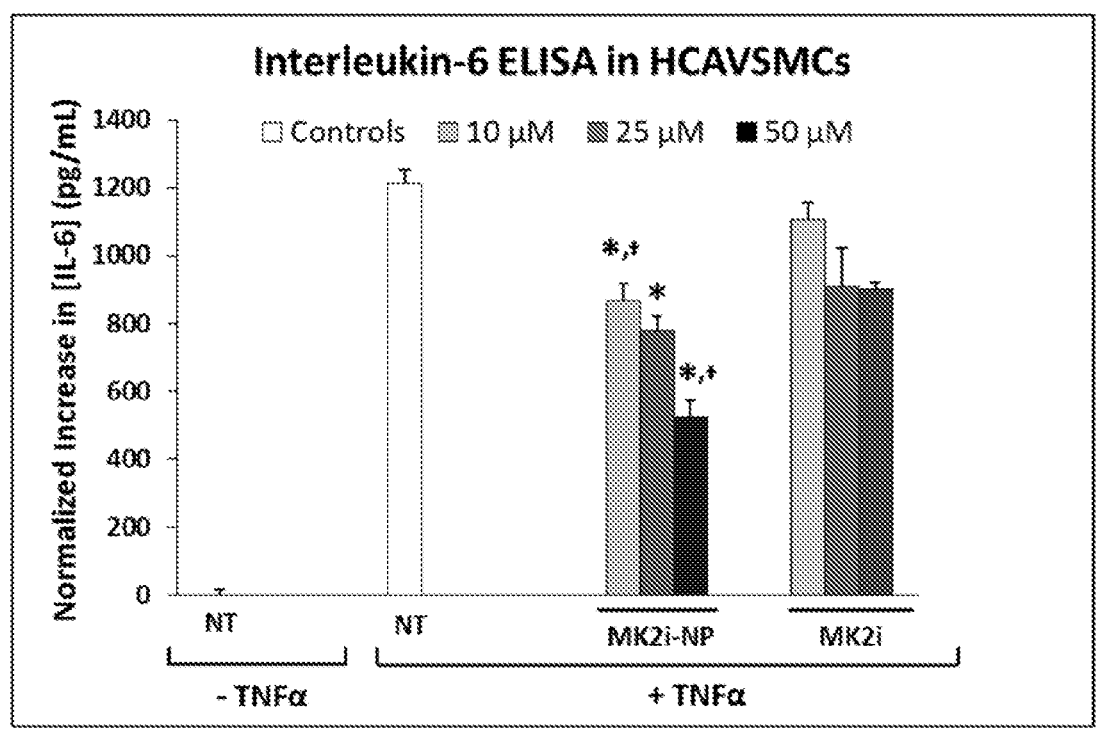
FIG. 34 illustrates that MK2i-NPs partially blocks TNFα-induced increase in IL-6 production in HCAVSMCs. Cells were stimulated with TNFα for 6 hours, treated for two hours with MK2i-NPs or MK2i peptide alone, and cultured for 24 hours in fresh media. All data is normalized to cell number. "NT" means no treatment, $*p<0.05$ vs. NT+TNFα, $^{†}p<0.05$ vs. MK2i at same concentration $^{\#}p<0.05$ vs. NE-MK2i-NPs at same concentration.
Figure 35:
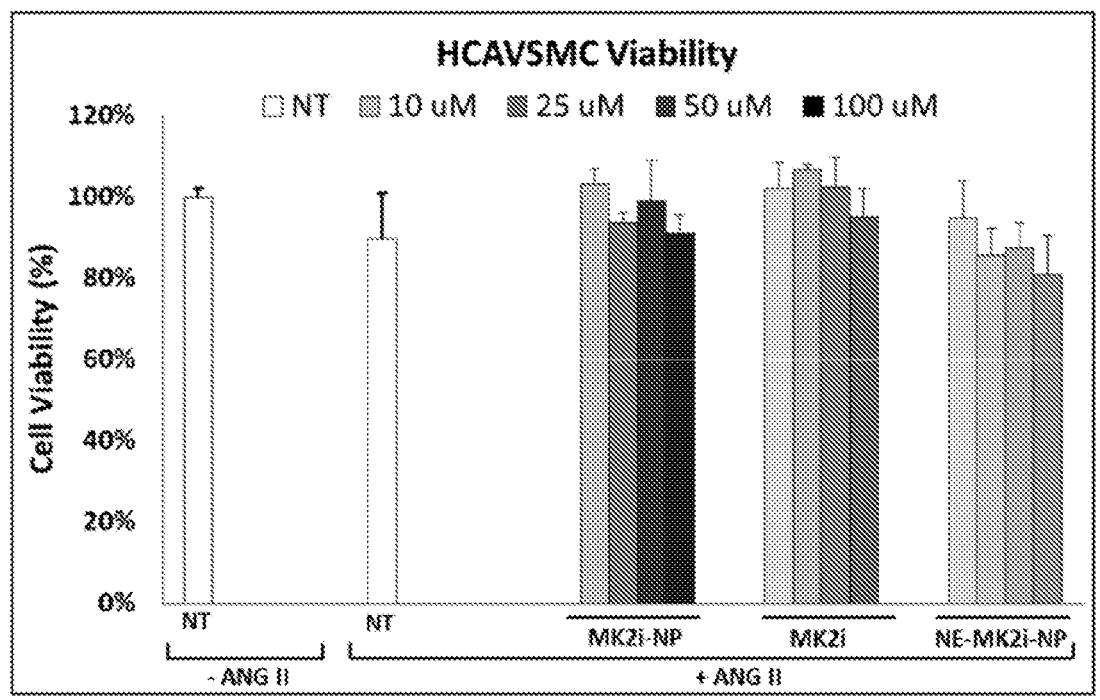
FIG. 35 shows cell viability in HCAVSMCs stimulated with 10 μM ANG II for 6 hours, treated for two hours with MK2i-NPs, NE-MK2i-NPs, or the MK2i peptide alone and cultured for 24 hours in fresh media. "NT" means no treatment, n=4.
Figure 36:
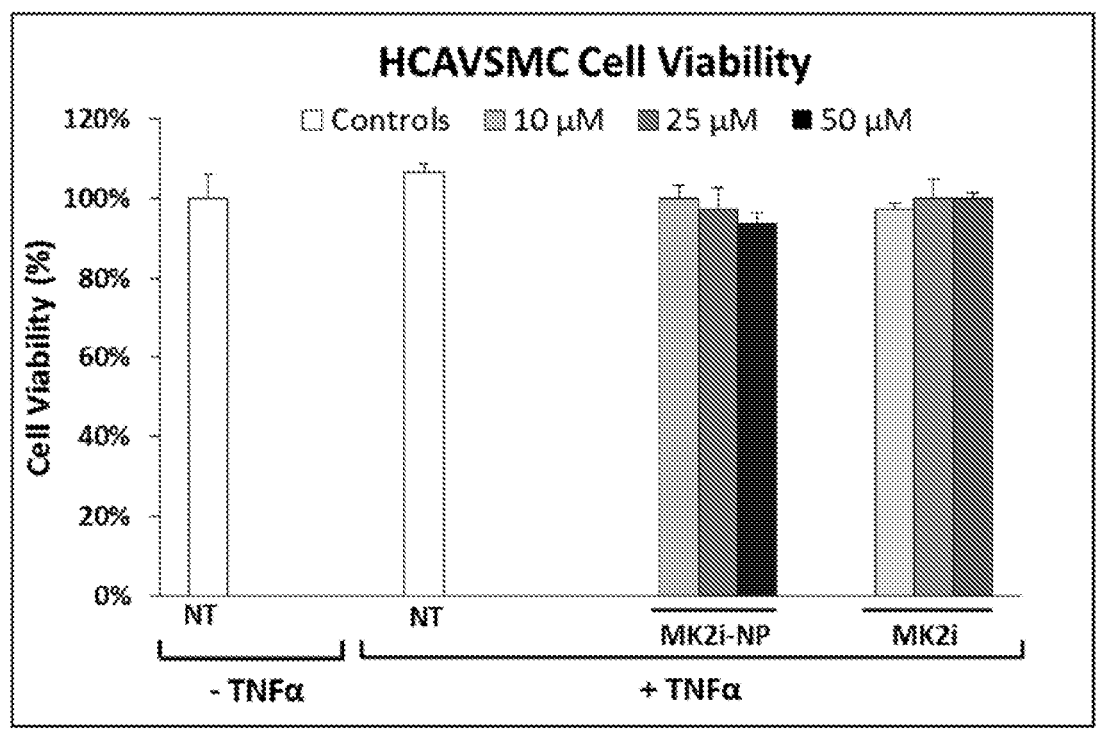
FIG. 36 shows cell viability in HCAVSMCs stimulated with TNFα for 6 hours, treated for two hours with MK2i-NPs or MK2i peptide alone, and cultured for 24 hours in fresh media, and n=4.

The inflammatory action of MK2 acts through downstream effectors, namely the post-transcriptional gene regulators tristetraprolin (TTP) and heterogeneous nuclear ribonucleoprotein A0 (hnRNPA0), which stabilizes and enhances expression of inflammatory cytokine mRNAs. To confirm that MK2i-NPs acts through blocking this mechanism, phosphorylation of HnRNP A0 was assessed. Western blots confirmed that MK2i-NPs significantly inhibited HnRNP A0 phosphorylation in HSV (FIG. 30, FIG. 31). In vitro ELISA analysis of cytokine production in Angiotensin-II stimulated HCAVSMCs confirmed this mechanism, and MK2i-NPs efficiently inhibited secretion of the primary hnRNPA0 target TNFα[21] (FIG. 32, FIG. 33). MK2i-NPs achieved TNFα inhibition equivalent to NE-MK2i-NP and MK2i at an order of magnitude lower dose (i.e. 10 μM MK2i produced an effect equivalent to 100 μM MK2i), and 100 μM MK2i-NPs fully abrogate Angiotensin II-stimulated TNFα production Inhibition of Interleukin-6 production in TNFα-stimulated HCAVSMCs also showed a significant increase in bioactivity for MK2i-NPs compared to the free peptide alone (FIG. 34). None of the treatments caused significant toxicity (FIG. 35, FIG. 36).

Figure 37:
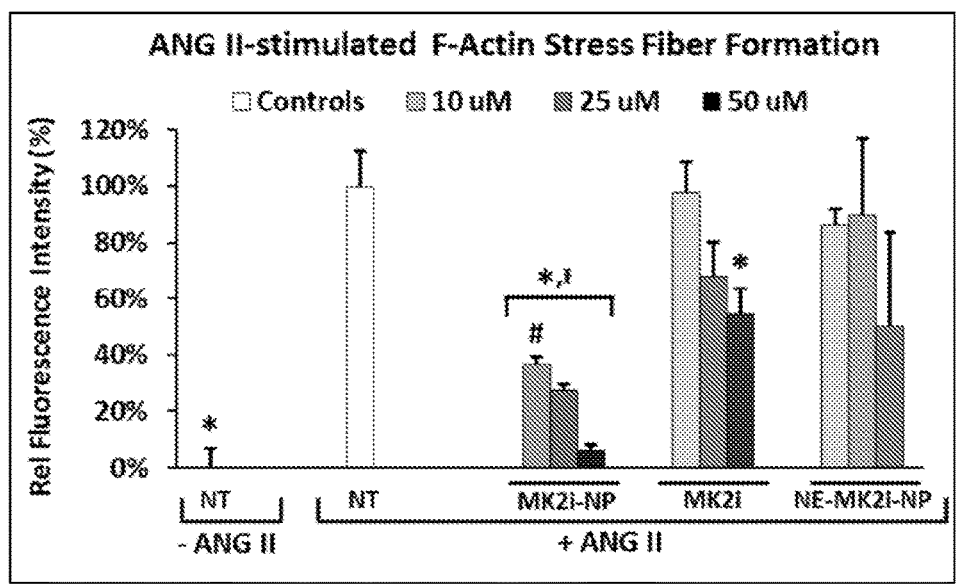
FIG. 37 illustrates that MK2i-NP treatment blocked F-actin stress fiber formation in response to ANG II stimulation. Data represent n≥3 cells from two separate experiments, $*p<0.05$ vs. NT+TNFα, $^{†}p<0.05$ versus MK2i at the same concentration. $^{\#}p<0.05$ vs. NE-MK2i-NPs at the same concentration. All data is normalized to cell number. "NT" means no treatment, $*p<0.05$ vs. NT+TNFα, $^{†}p<0.05$ vs. MK2i at the same concentration. $^{\#}p<0.05$ vs. NE-MK2i-NPs at the same concentration.
Figure 38:
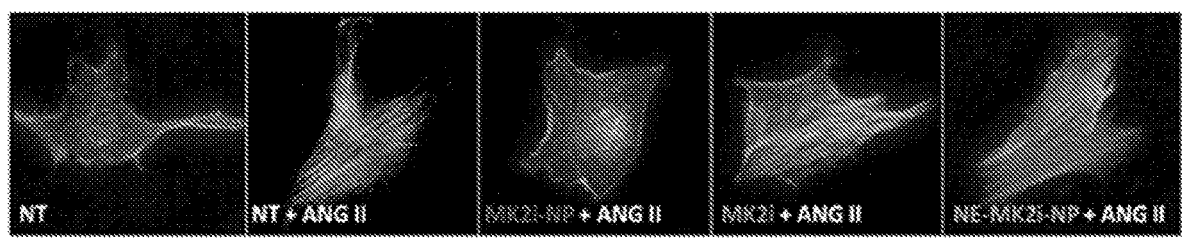
FIG. 38 provides representative fluorescence microscopy images of F-actin stress fiber formation in ANG II-stimulated HCAVSMCs after one hour treatment with MK2i-NPs or controls (25 μM MK2i).
Figure 39:
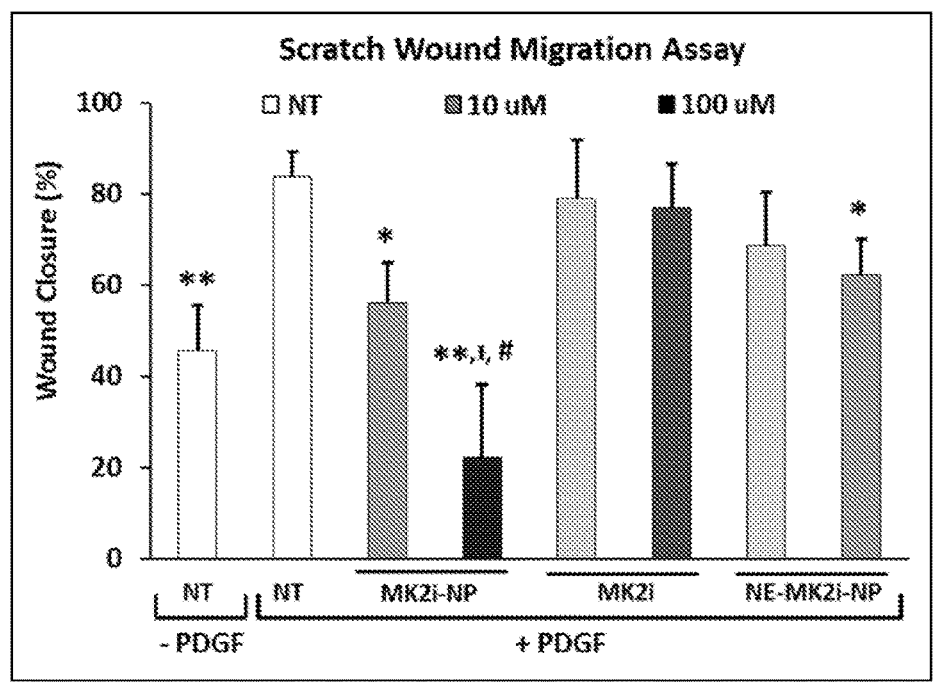
FIG. 39 shows that MK2i-NP treatment blocked migration in HCAVSMCs stimulated with the chemoattractant PDGF-BB (50 ng/mL) 24 hours after formation of a scratch wound, n≥3: $*p<0.05$, $**p<0.01$ vs. NT+PDGF, $^{†}p<0.05$ vs. MK2i at same concentration $^{\#}p<0.05$ vs. NE-MK2i-NPs at same concentration. All data is normalized to cell number. "NT" means no treatment, $*p<0.05$ versus NT+TNFα, $^{†}p<0.05$ vs. MK2i at the same concentration, $^{\#}p<0.05$ versus NE-MK2i-NPs at the same concentration.
Figure 40:
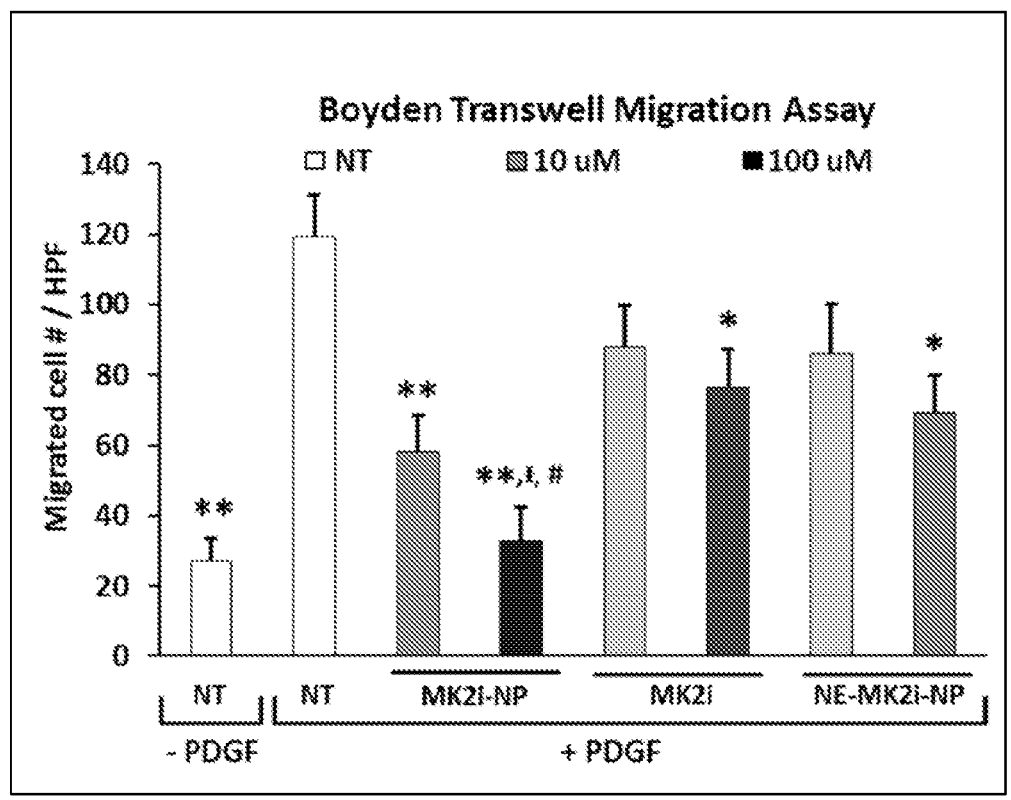
FIG. 40 shows that MK2i-NPs inhibited cell migration towards the chemoattractant PDGF-BB in a Boyden Chamber assay 8 hours after seeding onto the membrane, n=4 images from 7 separate Boyden chamber assays. $*p<0.05$, $**p<0.01$ vs. NT+PDGF, $^{†}p<0.05$ vs. MK2i at same concentration $^{\#}p<0.05$ vs. NE-MK2i-NPs at same concentration. All data is normalized to cell number. "NT" equals no treatment, $*p<0.05$ vs. NT+TNFα, $^{†}p<0.05$ versus MK2i at the same concentration $^{\#}p<0.05$ versus NE-MK2i-NPs at the same concentration.
Figure 41:
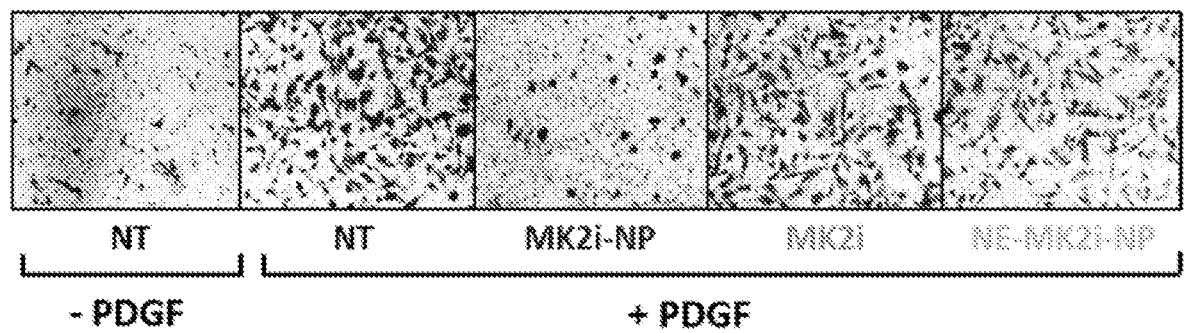
FIG. 41 presents representative microscopy images of cells that have migrated through the transwell insert, images obtained at 10× magnification. Treatment dose is 100 μM MK2i, MK2i-NPs, or NE-MK2i-NPs; PDGF-BB dose is 50 ng/mL.
Figure 42:
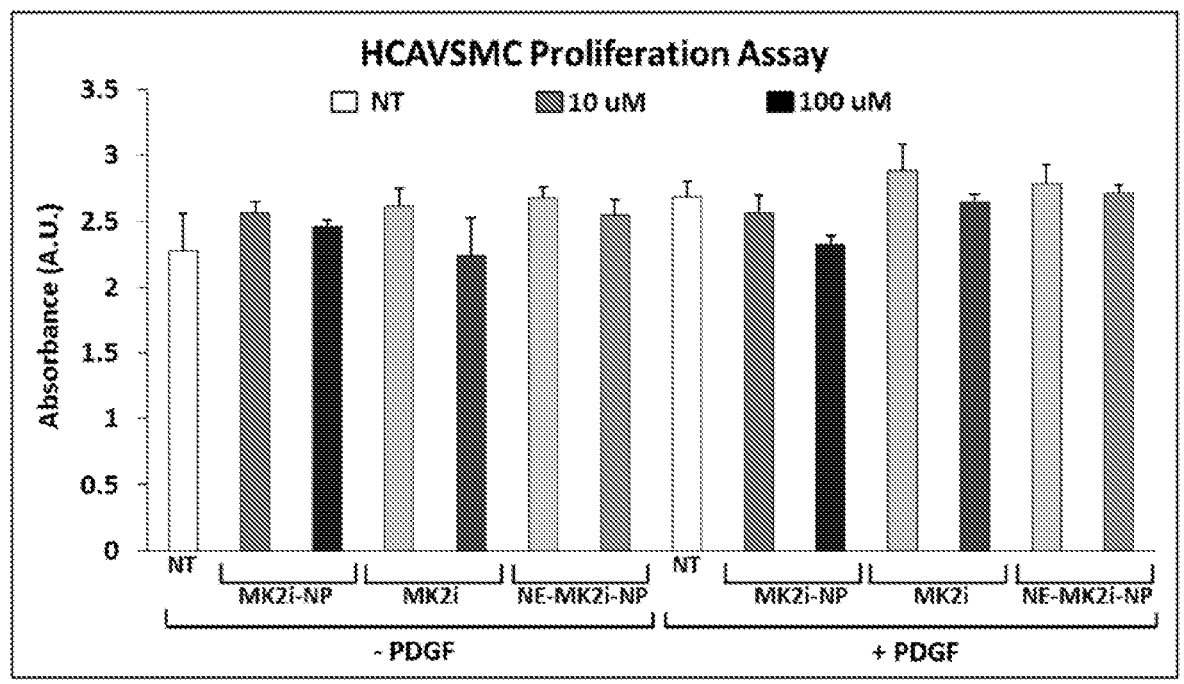
FIG. 42 shows cell proliferation in HCAVSMCs stimulated treated for 30 minutes with MK2i peptide alone, MK2i-NPs, or NE-MK2i-NPs and cultured for 24 hours in fresh media with (+) or without (−) 50 ng/mL PDGF-BB. "NT" means no treatment, and n=4.

MK2 activity also triggered stress fiber formation and cell migration through downstream phosphorylation of Lim Kinase (LIM-K) and heat shock protein 27 (HSP-27). Stress fiber formation is significantly inhibited by MK2i-NPs in Angiotensin-II stimulated HCAVSMCs, demonstrating significantly enhanced bioactivity compared to NE-MK2i-NPs and MK2i (FIG. 37). MK2i-NP treated cells displayed cortical actin staining similar to unstimulated control cells, whereas NE-MK2i-NPs and MK2i treatment did not fully block stress fiber formation (FIG. 38). To verify that MK2i-NPs prevented pathological VSMC migration characteristic of IH, both scratch wound and Boyden chamber migration assays were performed on HCAVSMCs in the presence of PDGF-BB (FIG. 39, FIG. 40, FIG. 41). In both assays, MK2i-NPs inhibited cell migration at an order of magnitude lower dose than free MK2i peptide. A proliferation assay confirmed that these results were not attributable to treatment effects on cell proliferation (FIG. 42).

Example 6

In Vivo Bioactivity in a Rabbit Vein Graft Interposition Model

Figure 43:
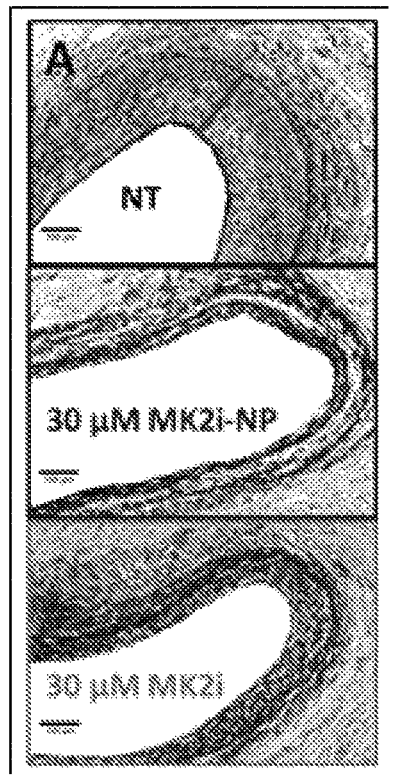
FIG. 43 illustrates that MK2i-NP treatment reduced neointima formation as shown in representative images of VVG stained histological sections of vein grafts. Indeed, intraoperative treatment with MK2i-NPs reduces neointima formation and macrophage persistence in in vivo in transplanted vein grafts.
Figure 44:
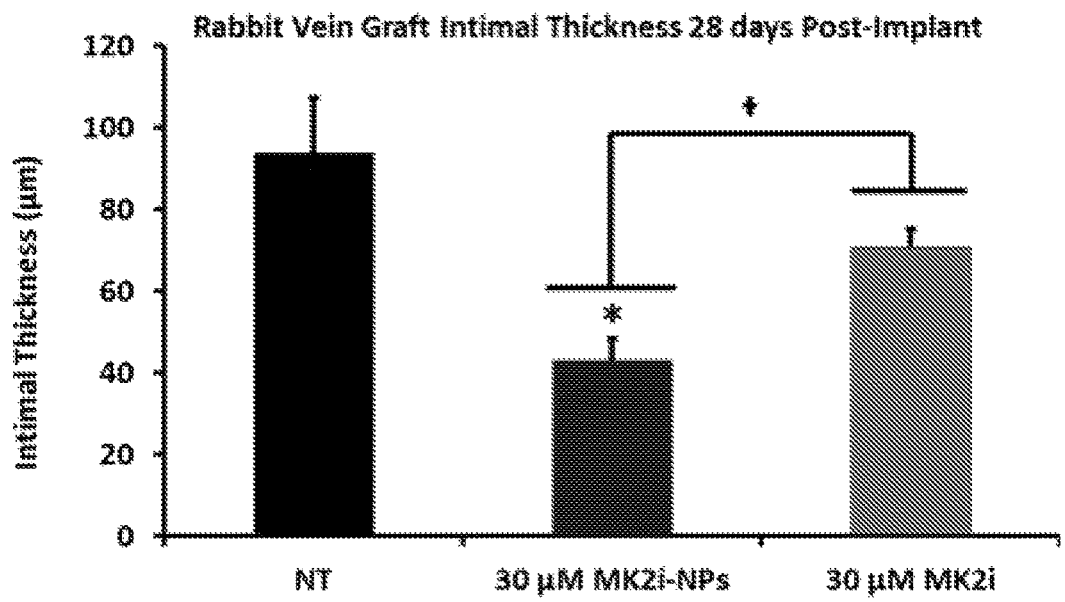
FIG. 44 provides quantification of intimal thickness in perfusion fixed jugular vein interposition grafts 28 days post-op. *p<0.01 vs NT, $^\dagger$p <0.05, n≥7 grafts per treatment group.

The therapeutic benefit of MK2i-NPs in vivo was assessed in a rabbit bilateral jugular vein graft interpositional transplant model that employed a polymeric cuff method to induce turbulent blood flow and accelerate graft IH. In this model, jugular vein grafts were treated for 30 minutes ex vivo, which represents minimal time that grafts are explanted during typical revascularization procedures. For each rabbit, one graft was treated, and the contralateral graft received vehicle control. Grafts were harvested 28 days post-operatively, and VVG stained histological sections were used for intimal thickness quantification (FIG. 43). Treatment with 30 μM MK2i-NPs significantly inhibited neointimal growth compared to both untreated controls and the free MK2i peptide, which did not alone produce any significant change in neointima formation (FIG. 44).

Figure 45:
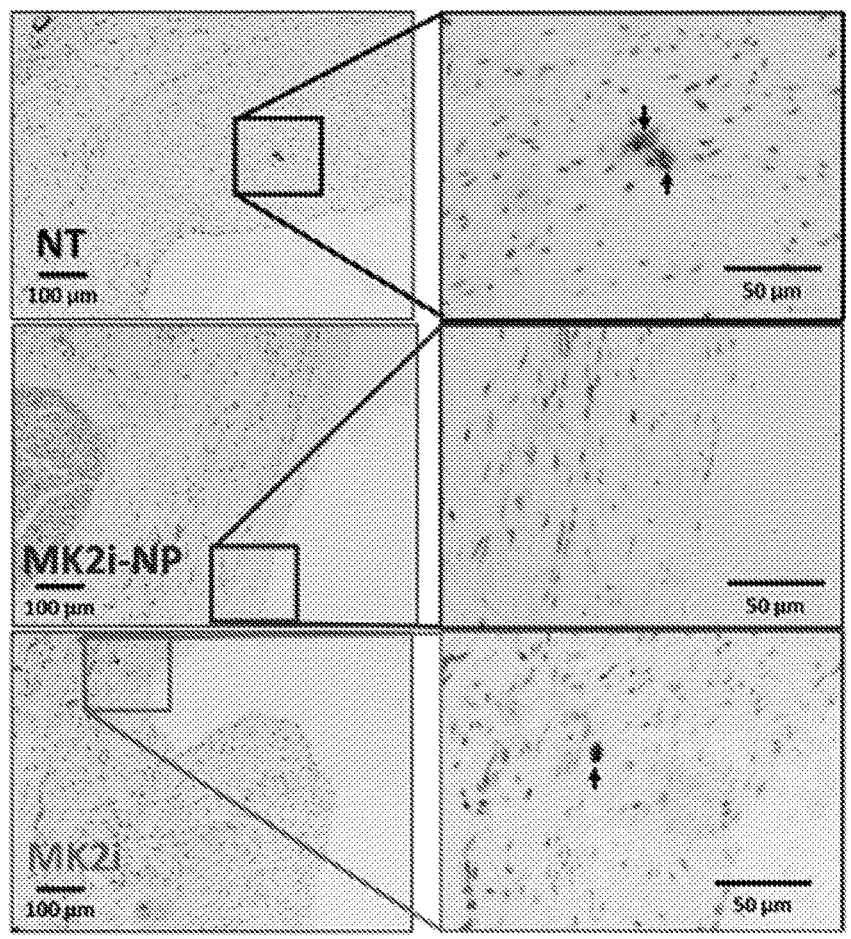
FIG. 45 shows that MK2i-NP treatment also reduced persistence of macrophages in the neointima as shown using RAM-11 immunohistochemistry on vein grafts. Arrows demarcate positively stained cells. Left column scale bar=100 μm, right column zoomed view scale bar=50 μm.
Figure 46:
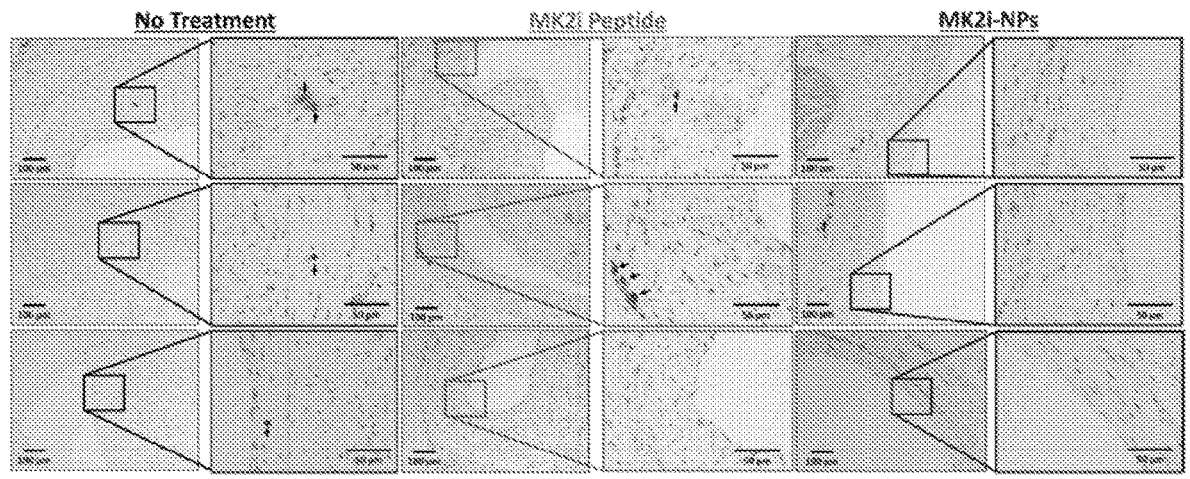
FIG. 46 shows representative RAM-11 staining images of rabbit jugular vein graft explants for each treatment group. Arrows demarcate positively stained cells. Left column scale bar=100 μm, right column zoomed view scale bar=50 μm.
Figure 47:
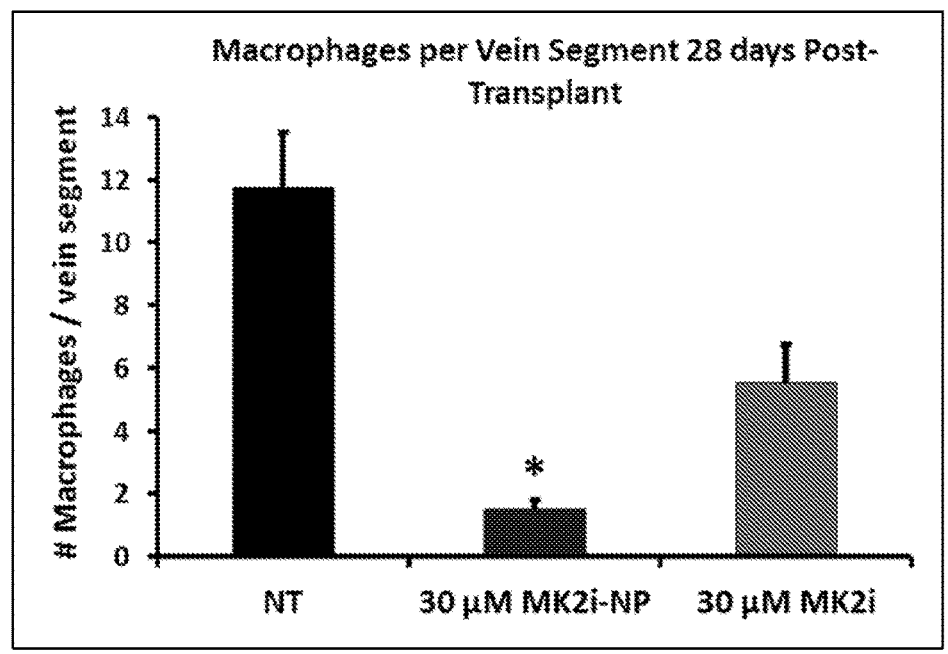
FIG. 47 provides quantification of RAM-11 positive macrophage staining in jugular vein graft sections, n=16 histological images from 4 vein segments, *p<0.05 vs. NT.

To confirm the anti-inflammatory effects of MK2i-NPs in the transplanted vein grafts, tissue sections were stained with a rabbit macrophage specific antibody, RAM-11 (FIG. 45, FIG. 46). MK2 activated the post-transcriptional gene regulator hnRNP A0 that upregulates production of inflammatory cytokines such as TNFα, and TNFα production induces expression of monocyte chemoattractant protein-1 (MCP-1) in smooth muscle cells, endothelial cells, fibroblasts, and leukocytes present in vein grafts. MCP-1 is a potent chemoattractant for circulating inflammatory cells and MCP-1 mRNA levels have been shown to be elevated even at 8 weeks post-grafting in vein grafts, resulting in recruitment of monocytes and tissue macrophages to the vein wall and leading to the pathogenesis of IH. To this end, macrophage analysis performed 4 weeks post-transplant demonstrates a significant reduction in persistence of intimal macrophages in MK2i-NP treated grafts, suggesting therapeutic inhibition of TNFα-induced macrophage recruitment through MCP-1 (FIG. 47).

Discussion

The cellular uptake and bioactivity of MK2i peptide was enhanced by an order of magnitude without altering the native structure of the therapeutic peptide, circumventing potential deleterious effects on target binding and bioactivity. These results also highlight the role that the p38 MAPK/MK2 pathway plays in the transition of VSMCs to an activated, pathological phenotype that leads to IH and graft failure.

Furthermore, CPPs can be conjugated to therapeutic peptides to increase cellular uptake, however, CPP identity has been shown to significantly influence target specificity and most CPPs are not capable of escaping the endolysosomal trafficking pathway. Contrary to the paradigm of using positively charged CPP sequences or polymeric transfection agents for delivery of nucleic acids, it was found that formulation of positively charged, CPP-based MK2i peptide into a net negatively charged polyplex formulation significantly enhanced uptake in VSMCs.

VSMCs express a variety of scavenger receptors that uptake negatively charged particles (e.g. LDL), and vascular stress upregulates the expression of these receptors. The in vitro results suggest that the high levels of MK2i cell internalization and escape from the endo-lysosomal trafficking pathway achieved with MK2i-NPs were dependent on the specific composition of PPAA, rather than purely dictated by polyplex morphology and charge. This can be deduced from the observation that NE-MK2i-NPs of similar size and charge to MK2i-NPs were not found to increase cellular uptake of the MK2i peptide.

While not wishing to be bound by theory, the accelerated cell internalization of MK2i-NPs may be due to a change in cell surface interactions and/or uptake mechanism. While not wishing to be bound by theory, it is suggested that MK2i-NPs enter smooth muscle cells through multiple endocytotic routes and that macropinocytosis may be operative in internalization of MK2i-NPs but not NE-MK2i-NPs or MK2i. It is suggested herein that PPAA-based polyplexes may biomimic the reported adenoviral internalization mechanism that triggers a combination of macropinocytosis and endosomal leakage, leading to enhanced cytosolic access.

Macropinosomes are trafficked to acidified compartments and can be leakier than other endosomal vesicles. This internalization route, combined with the pH-dependent membrane disruptive activity of PPAA, may account for the significant increase of MK2i intracellular half-life when delivered via MK2i-NPs.

Intracellular half-life ($T_{1/2}$) of MK2i was increased 14-fold by incorporation into MK2i-NPs (MK2i-NP $T_{1/2}$=57.8 days vs. MK2i $T_{1/2}$=4.1 days; calculated based on intracellular peptide fluorescence at 0 and 5 days following treatment). This increase in $T_{1/2}$ is applicable to vein grafting applications or the like because it potentially enables application of a single treatment at the time of grafting that will have a prolonged therapeutic effect throughout the full duration of both the acute inflammatory and healing phases.

Because the MK2i-NPs produced an estimated intracellular half-life of approximately 8 weeks, a single treatment prior to implantation may be sufficient to inhibit IH for the duration of vein graft adaptation, yielding significantly improved long-term performance. Ex vivo, intraoperative treatment of grafts is a useful therapeutic strategy to enhance delivery to the target tissue and avoid potential for off-target effects or systemic toxicity.

The subject matter of the present disclosure establishes that polyplex formulation using PPAA significantly enhances the intracellular delivery and bioactivity of MK2i peptide and that this system has significant clinical potential as a prophylactic therapy applied during vascular graft transplantation to inhibit IH.

Materials and Methods

Synthesis of Cell Penetrant MK2 Inhibitory Peptide

An MK2 inhibitory peptide (MK2i) with the sequence YARAAARQARA-KALARQLGVAA was synthesized on a PS3 peptide synthesizer (Protein Technologies, Inc. Tucson, Ariz.) utilizing standard FMOC Chemistry. N-methylpyrrolidone (NMP, Fischer Scientific) was utilized as a solvent in peptide syntheses. HCTU was used as an activator (Chempep, Wellington, Fla.) in the presence of N-methylmorpholine. All amino acids were double coupled in order to maximize yield and purity. Peptides were cleaved/deprotected in TFA/Phenol/$H_2O$/triisopropylsilane (88/5/5/2). The peptide as then further purified by reverse phase HPLC on a Waters 1525 binary HPLC pump outfitted with an extended flow kit, a Waters 2489 UV/Visible detector, and a phenomenex Luna C18(2) AXIA packed column (100A, 250×21.2 mm, 5 micron). HPLC grade water with 0.05% formic acid and HPLC grade acetonitrile were used as the mobile phase, and the peptide was purified utilizing a 90% A to 90% B gradient over 25 minutes (16 mL/min). Acetonitrile as removed from purified fractions with a rotary evaporator, and the purified fractions were then lyophilized. Peptide purity was verified through electrospray ionization mass spectrometry (ESI-MS) on a Waters Synapt ESI-MS.

Monomer and Polymer Synthesis

All reagents were purchased from Sigma and were of analytical grade unless otherwise stated. 2-propylacrylic acid was synthesized according to the procedure outlined by Ferrito et al. utilizing diethyl propylmalonate (Alfa Aesar) as a precursor. The 4-cyano-4-(ethylsulfanylthiocarbonyl) sulfanylvpentanoic acid (ECT) chain transfer agent (CTA) was synthesized as previously described. RAFT polymerization of the PPAA homopolymer was carried out in bulk under a nitrogen atmosphere at 70° C. for 48 hours using 2,2'-azobis-isobutyrylnitrile (AIBN) as the free radical initiator.

The reaction mix was put through three freeze-vacuum-thaw cycles and purged with nitrogen for thirty minutes prior to polymerization. The molar ratio of CTA to AIBN is 1 to 1, and the monomer to CTA ratio was set so that a molecular weight of 25,000 g/mol was achieved at 100% conversion. Following polymerization, the resultant polymer was dissolved in DMF and precipitated into ether 5 times before drying overnight in vacuo. RAFT polymerization of the PAA homopolymer was carried out in distilled dioxane under a nitrogen atmosphere at 70° C. for 18 hours using AIBN as the free radical initiator. The reaction mix was purged with nitrogen for thirty minutes prior to polymerization. The molar ratio of CTA to AIBN is 5 to 1, and the monomer to CTA ratio was set so that a molecular weight of 8,000 g/mol is achieved at 100% conversion. Following polymerization, the resultant polymer was dissolved in dioxane and precipitated into ether 5 times before drying overnight in vacuo. Gel permeation chromatography (GPC, Agilent) was used to determine molecular weight and polydispersity ($M_w/M_n$, PDI) of the PPAA and PAA homopolymers using HPLC-grade DMF containing 0.1% LiBr at 60° C. as the mobile phase. Molecular weight calculations were performed with ASTRA V software (Wyatt Technology) and were based on experimentally-determined dn/dc values determined through offline injections of the polymer through a refractive index detector (calculated PPAA dn/dc=0.087 mL/g, calculated PAA dn/dc=0.09 mL/g).

MK2i Nano-Polyplex (MK2i-NP) Synthesis and Characterization

PPAA was dissolved in 1 M NaOH and diluted into a phosphate buffer (pH 8) to obtain a stock solution. Purified MK2i peptide was dissolved in phosphate buffer (pH 8). The MK2i peptide and PPAA polymer were mixed at a range of CRs from [$NH_3^+$]:[$COO^-$]=10:1 to 1:10 to form MK2i-NPs. The resulting polyplexes were syringe filtered through 0.45 μm PTFE filter, and the hydrodynamic diameter and ζ-potential were characterized on a Malvern Zetasizer Nano-ZS with a reusable dip cell kit (Malvern Instruments Ltd., Worcestershire, U.K.).

A CR of 1:3 was then chosen and used in subsequent in vitro, ex vivo, and in vivo studies. Nano-polyplexes formulated at the same CR with the non-endosomolytic polymer PAA (i.e., NE-MK2i-NPs) were analyzed by DLS and used as a vehicle control. In order to verify the sizes indicated by DLS analysis, MK2i-NPs and NE-MK2i-NPs at a charge ratio of 1:3 were visualized through transmission electron microscopy (TEM) imaging. TEM samples were prepared by inverting carbon film-backed copper grids (Ted Pella) onto a 20 μL droplet of aqueous polyplex suspensions (1 mg/mL) and blotted dry. All samples were then inverted onto a 20 μL droplet of 3% Uranyl Acetate and stained for 2 min. After blotting the sample dry, samples were desiccated in vacuo for two hours prior to imaging on a Philips CM20 system operating at 200 kV. Images were collected using a CCD camera with AMT Image capture Engine software (Advanced Microscopy Techniques, Danvers, Mass.). The pH-dependent size changes of polyplexes at a CR of 1:3 were then quantified by DLS analysis at various pH values in PBS −/− (i.e. pH 7.4, 6.8, 6.2, and 5.6).

pH-Dependent Membrane Disruption Hemolysis Assay

To assess the endosomal disruptive potential of MK2i-NPs, a red blood cell hemolysis assay was utilized to measure MK2i-NP pH-dependent disruption of lipid bilayers. Whole human blood was drawn from an anonymous donor, and plasma was removed through centrifugation and saline washes. The remaining erythrocytes were washed three times with 150 mM NaCl and resuspended into phosphate buffers corresponding to physiologic (pH 7.4), early endosome (pH 6.8), early/late endosome (pH 6.2), and late endosome/lysosomal (pH 5.8) environments. MK2i-NPs, NE-MK2i-NPs, MK2i peptide alone (1-40 μg/mL), PBS (negative control), or 1% Triton X-100 (positive control) were added to the erythrocyte suspensions and incubated at 37° C. for 1 hour. Intact erythrocytes were pelleted via centrifugation, and supernatant was transferred to a new 96-well plate. The hemoglobin content within the supernatant was then measured via absorbance at 541 nm. Percent hemolysis was determined relative to Triton X-100 and PBS controls.

Cell Culture

Primary HCAVSMCs were obtained from Lonza; HCAVSMCs were cultured in complete growth medium vascular cell basal medium (ATCC) supplemented with 5% FBS, human basic fibroblast growth factor (bFGF, 5 ng/mL), human insulin (5 µg/mL), ascorbic acid (50 µg/mL), L-glutamine (10 mM), human epidermal growth factor (EGF, 5 ng/mL), and 1% penicillin-streptomycin].

All cultures were maintained in 75 cm$^2$ polystyrene tissue culture flasks in a 37° C. and 5% $CO_2$ environment with cell culture media refreshed every other day. Cells were grown to 80-90% confluence prior to being harvested and passaged. All cells were seeded at a density of 20,000-30,000 cells/cm$^2$, as required for each specific experiment. Only cells from early passages (numbers 3-8) were used in experiments.

Inflammatory Cytokine Analysis

200 µl of cell suspension (at 10,000 cells/well) was seeded onto 96-well plates to yield an approximate 70% confluence per well. Cells were allowed to adhere to the plate overnight.

Tumor Necrosis Factor-α ELISA

Cells were treated in low serum media (DMEM, 1% FBS, and 1% P/S, to achieve cellular quiescence) with 10 µM ANG-II for four hours followed by treatment with MK2i-NPs, MK2i, or NE-MK2i-NPs for two hours. Following treatment, each well was aspirated and supplemented with fresh medium. After 24 hours, 100 µL of supernatant was collected and frozen at −80° C. until cytokine analysis was performed. A Human TNF-α (cat #900-K25) ELISA development kit (Peprotech; Rocky Hill, N.J.) was used to measure cytokine levels in supernatant collected from treated cells according to the manufacturer's protocol. All data were then normalized to cell viability determined by a CytoTox-ONE Homogenous Membrane Integrity assay (Promega) according to the manufacturer's protocol.

Interleukin-6 ELISA

Cells were treated in low serum media with 20 ng/mL TNF-α for four hours followed by treatment with MK2i-NPs, MK2i, or NE-MK2i-NPs for two hours. Following treatment, each well was aspirated and supplemented with fresh medium. After 24 hours, 100 µL of supernatant was collected and frozen at −80° C. until cytokine analysis could be performed. A Human TNF-α (cat #900-K16) ELISA development kit (Peprotech; Rocky Hill, N.J.) was used to measure cytokine levels in supernatant collected from treated cells according to the manufacturer's protocol. All data were then normalized to cell viability determined by a CytoTox-ONE Homogenous Membrane Integrity assay (Promega) according to the manufacturer's protocol.

F-Actin Stress Fiber Assay

HCAVSMCs were seeded in Lab-Tek II 8-well chambered coverglass (Thermo Scientific Nunc) at 15,000 cells/well and allowed to adhere overnight. Cells were then treated in low serum media with MK2i-NPs, NE-MK2i-NPs, or MK2i peptide alone at concentrations of 10, 25, and 50 µM for 1 hour. Following treatment, cells were washed 2× with PBS −/− and subsequently treated with 1 µM Angiotensin II (Sigma Aldrich) or PBS −/− (negative control) for 2 hours. After ANG-II stimulation, cells were washed 2× with PBS, fixed in 4% paraformaldehyde for 5 minutes, permeabilized with 0.4% Triton-X 100 for 10 minutes, and blocked with 1% BSA in PBS −/− for 15 minutes. Cells were then stained with Hoechst solution (1/5000 dilution in PBS −/−) for 10 minutes followed by staining with Alexa-488-Phallodin for 30 minutes. Stained coverslips were then inverted onto glass cover slides with ProLong Gold antifade mounting medium (Invitrogen). Slides were dried for 24 hours prior to sealing and imaging. Treated cells were imaged using a Nikon Eclipse Ti inverted fluorescence microscope (Nikon Instruments Inc, Melville, N.Y.) with NIS Elements imaging software. Gain settings and exposure times were kept constant for all images taken. Stress fiber formation was quantified using imageJ software to free hand select individual cells and to calculate the relative fluorescence intensity of n≥5 cells from 2 independent experiments for each treatment group.

Chemotaxis Migration Assays: Scratch Wound Assay

HCAVSMCs were seeded in Lab-TEK II 8-well chambered coverglass at a density of 20,000 cells/well in 250 µl low serum growth media and were allowed to adhere overnight to achieve a nearly confluent (90-95%) monolayer. Cells were treated with MK2i-NPs, NE-MK2i-NPs, MK2i peptide or PBS −/− for 30 minutes. Following treatment, scratch wounds were made with a 10 uL pipette tip through the middle of each cell monolayer. The media was then replaced with low serum growth media containing a CellTracker™ Green BODIPY® dye (Invitrogen) according to the manufacturer's protocol for thirty minutes to stain the cytoplasm for visualization of migrating cells. Following treatment with the dye, media was replaced with low serum growth media containing 50 ng/ml PDGF-BB (or with PBS −/− for the negative control). Scratch wound areas were then imaged at 0,3,6,12, and 24 hours using a Nikon Eclipse Ti inverted fluorescence microscope (Nikon Instruments Inc, Melville, N.Y.) with NIS Elements imaging software. Wound closure was calculated with imageJ software by quantifying the scratch wound area around the periphery of migrating cells normalized to the original scratch wound area. Scratch wound assays for each treatment group were performed in 3 independent experiments.

Chemotaxis Migration Assays: Boyden Chamber Assay

HCAVSMCs were seeded in a 24 well plate at a density of 30,000 cells/well in low serum media and allowed to adhere overnight. Cells were treated for 30 minutes with MK2i-NPs, NE-MK2i-NPs, MK2i peptide or PBS −/−. Following treatment, each well was washed 2× with PBS −/−, trypsinized, resuspended in 100 µl low serum growth media, and plated onto 6.5 mm, 8 µm pore polycarbonate inserts (Corning) in a 24 well plate with 600 µl low serum growth media containing 50 ng/ml PDGF-BB (or PBS −/− for the negative control) in the lower chamber. Cells were allowed to migrate for eight hours, and then cells on the upper side of each insert were gently removed with a cotton swab. Cells on the lower side of each insert were then fixed and stained using a Modified Giemsa Differential Quik Stain Kit (Polysciences). Briefly, inserts were fixed in solution A for at least 10 seconds, dipped 5 times in solution B, and then dipped 5 times in solution C. 4 images were taken from the four quadrants of each insert and the number of cells/high power field were quantified in imageJ by thresholding each image and manually counting the cells. Each treatment was performed in triplicate and average cell number/HPF is calculated.

Cell Proliferation Assay

HCAVSMCs were seeded in a 96 well plate at 10,000 cells/well in low serum media and allowed to adhere overnight. Cells were treated for 30 minutes with MK2i-NPs, NE-MK2i-NPs, MK2i peptide or PBS −/− (for positive and negative controls). Each treatment was then aspirated and replaced with 100 µl low serum growth media±50 ng/mL PDGF-BB. After 24 hours of incubation, a CellTiter 96® Aqueous Non-Radioactive Cell Proliferation Assay (Promega) was performed according to the manufacturer's protocol. Briefly, 100 µl phenazine methosulfate (PMS) solution was added to 2.0 ml MTS solution and mixed. 20 µl of PMS/MTS solution was then added to each well of the 96 well plate containing 100 µl medium, and the plate was incubated for 4 hours at 37° C. in a humidified, 5% $CO_2$ atmosphere. Following incubation, the absorbance of each well was recorded at 490 nm with a TECAN Infinite M1000 Pro plate reader to determine relative proliferation rates between treatment groups.

Microscopic Analysis of Cellular Uptake and Intracellular Trafficking

An amine-reactive Alexa-488 succinimidyl ester was dissolved in DMSO and mixed at a 1 to 3 molar ratio with the MK2i peptide in 100 mM sodium bicarbonate buffer (pH=8.3). Unreacted fluorophore and organic solvent were removed using a PD-10 miditrap G-10 desalting column, and the fluorescently labeled peptide was lyophilized. PPAA and PAA polymers were mixed with fluorescently labeled MK2i peptide at a CR of $[NH_3^+]/[COO^-]=1:3$ and syringe filtered through a 0.45 µm PTFE filter to form fluorescent MK2i-NPs and control NE-MK2i-NPs, respectively. Fluorescent MK2i-NP and NE-MK2i-NP hydrodynamic diameter and surface charge were measured by DLS and Zeta potential analysis, respectively. Fluorescent MK2i-NPs, NE-MK2i-NPs, or MK2i peptide alone were applied to HCAVSMCs grown on Lab-Tek II 8-well chambered coverglass (Thermo Scientific Nunc) at a concentration of 10 µM MK2i peptide in DMEM media supplemented with 1% FBS and 1% P/S. Cells were treated for 2 hours, washed 2× with PBS −/−, and media is replaced. Cells were then incubated for an additional 0, 2, 4, 10, or 22 hours in fresh media. For the final two hours of incubation, 50 nM LysoTracker® Red DND-99 (Invitrogen) was added to each well in order to visualize acidic endo/lysosomal vesicles within cells. After incubation, cells were washed with 0.1% trypan blue for 1 minute to quench extracellular fluorescence followed by 2 additional washes with PBS −/−. Cells were then imaged using a LSM 710 META fluorescence microscope with ZEN imaging software (Carl Zeiss Thornwood, N.Y.). Gain settings were kept constant for all images acquired for every treatment group.

All images were processed using imageJ software, and colocalization is analyzed using Just Another Colocalization Plugin (JACoP). Mander's overlap coefficients (the fraction of pixels with positive pixel values in both fluorescent channels) were then calculated for n≥3 separate images for each treatment group to quantify colocalization. To determine treatment effects on the size of the compartments where the peptide was found, the free hand selection tool in ImageJ was used to outline ≥50 individual intracellular compartments for each treatment group, and the area of each was quantified and averaged.

Flow Cytometric Quantification of Intracellular Uptake and Retention

HCAVSMCs were grown to 80-90% confluence, harvested, and seeded at 20,000 cells per well in a 24-well plate and were allowed to adhere overnight in low serum media. Fluorescent MK2i peptide, MK2i-NPs, and NE-MK2i-NPs were synthesized as noted above for microscopy analysis, and HCAVSMCs were treated at a concentration of 10 µM MK2i for two hours. Following treatment, cells were washed with PBS −/−, washed with CellScrub buffer (Genlantis) for 10 minutes at room temperature to remove extracellular polyplexes and/or peptide, washed 2× in PBS −/−, and the media was refreshed with complete growth media. Cells were then incubated for an additional 0, 12, 24, 72, or 120 hours. Cells were then washed with PBS −/−, trypsinized, and resuspended in 0.1% Trypan blue in PBS (−/−) for analysis on a FACSCalibur flow cytometer (Becton Dickinson) with BD CellQuest™ Pro software (V 5.2). Data was exported and analyzed with FlowJo software (V 7.6.4). All samples are run in triplicate.

Human Saphenous Vein

De-identified, discarded segments of HSV were collected from consenting patients undergoing coronary or peripheral vascular bypass surgeries. Following surgical resection, HSV segments were stored in saline solution until the end of the surgical procedure, at which time they were placed in cold transplant harvest buffer (100 mM potassium lactobionate, 25 mM $KH_2PO_4$, 5 mM $MgSO_4$, 30 mM raffinose, 5 mM adenosine, 3 mM glutathione, 1 mM allopurinol, 50 g/L hydroxyethyl starch, pH 7.4). All HSV segments were used within 24 hours of harvest. Utilizing sterile technique in a sterile culture hood, HSV segments were transferred to a 60 mm Petri dish. The end of each segment (0.5 mm) was removed with a blade, and excess adventitial and adipose tissue was removed with minimal manipulation. HSV segments were cut into consecutive rings with an approximate width of 1.0 mm to be utilized in organ culture or muscle bath experiments. Two rings from each segment were immediately fixed in 10% formalin at 37° C. for 30 min to obtain pre-culture intimal thickness measurements.

HSV Organ Culture and Assay for Ex Vivo IH

In preparation for testing vein segment functional viability, HSV rings were weighed, and their lengths were recorded. HSV rings were then suspended in a muscle bath containing a bicarbonate buffer (120 mM NaCl, 4.7 mM KCl, 1.0 mM $MgSO_4$, 1.0 mM $NaH_2PO_4$, 10 mM glucose, 1.5 mM $CaCl_2$, and 25 mM $Na_2HCO_3$, pH 7.4) equilibrated with 95% O2 and 5% CO2 at 37° C. The rings were stretched, and the length progressively adjusted until maximal tension was obtained. Normalized reactivity as obtained by determining the passive length-tension relationship for each vessel segment. Rings were maintained at a resting tension of 1 g, which produced maximal responses to contractile agonists, and equilibrated for 2 h in buffer. Force measurements were obtained using a Radnoti Glass Technology (Monrovia, Calif.) force transducer (159901A) interfaced with a Powerlab data acquisition system and Chart software (AD Instruments, Colorado Springs, Colo.).

HSV rings were initially contracted with 110 mM KCl (with equimolar replacement of NaCl in bicarbonate buffer), and the force generated was measured. 110 mM KCl causes membrane depolarization, leading to contraction of vessels containing functionally viable smooth muscle. After vessel viability was verified with multiple KCl challenges, additional rings were cut and placed in a 24 well plate and maintained in RPMI 1640 medium supplemented with 30% FBS, 1% L-glutamine and 1% penicillin/streptomycin for 14 days at 37° C. in an atmosphere of 5% CO2 in air. The rings were untreated, treated with MK2i-NPs, NE-MK2i-NPs, MK2i peptide, or buffer alone for 2 hours, washed, and given fresh media. The culture medium without treatments was replaced every 2 days for 14 days.

HSV Viability

An MTT assay is performed on HSV rings at 1 and 14 days after treatment. HSV rings were prepared and treated as noted above, and following 1 or 14 days of organ culture, HSV rings were weighed and then placed in 250 µL of 0.01% methyl tetrazolium dissolved in DPBS. The rings were placed in a 37° C. incubator for 1 hour. The reaction was stopped by placing the rings into distilled water. The rings were then placed into 1 mL of CelloSolve and incubated at 37° C. overnight. Following incubation, rings were mixed in solution, and the CelloSolve was extracted and placed into a cuvette where the optical density at 570 nm is determined. Relative viability calculations were based on the optical density normalized to the wet weight of the ring.

Vessel Morphometry

After 14 days of organ culture, vein segments were fixed in 0.5 ml of 10% formalin at 37° C. for 30 min and embedded in paraffin for sectioning. Beginning at the mid-portion of each ring, 5 transverse sections, spaced 5 μm apart, were cut from each specimen. Sections were then stained with Verhoeff-van Gieson stain. Histology sections were imaged using a Nikon Eclipse Ti inverted fluorescence microscope (Nikon Instruments Inc, Melville, N.Y.), and six radially parallel measurements of intimal and medial thickness were randomly taken from each section using NIS Elements imaging software (total of 6-12 measurements per ring, n≥3 rings per treatment group from separate donors). Intima was defined as tissue on the luminal side of the internal elastic lamina or the chaotic organization of the cells contained within it, whereas the medial layer was contained between the intimal layer and the external elastic lamina. Intimal and medial thickening was measured for each section at 10× magnification with the microscope's computerized image analysis software.

MK2i Vessel Penetration

After verifying viability, HSV rings were treated with Alexa-568 labeled MK2i peptide, MK2i-NPs, or NE-MK2i-NPs for 30 minutes, washed 2× in PBS −/−, and immediately embedded in OCT compound and frozen over dry ice. 5 μm cryosections were cut from the middle of each treated vessel and mounted on microscope slides for analysis of peptide delivery into the vessel wall. Vessel penetration was quantified in imageJ by calculating the mean intimal fluorescence from each section and normalizing to intimal area (n=3 separate donors for each treatment group).

Western Blot Analysis

Following two hours of treatment and 24 hours of organ culture in fresh media, a portion of the treated HSV rings were snap-frozen with liquid nitrogen, pulverized, and homogenized using urea-DTT-CHAPS buffer. Lysates were centrifuged (6000 g, 20 minutes), and the supernatant was collected for evaluation of HnRNP A0 phosphorylation. Equal amounts of protein (20 μg per lane) were loaded on 15, 10, or 4-20% SDS-PAGE gels; proteins were electrophoretically separated and then transferred to Immobilon membranes (Millipore, Billerica, Mass.). Membranes were probed overnight at 4° C. with primary antibodies for phospho-hnRNP A0 (Millipore) and unphosphorylated hnRNP A0 (Santa Cruz). After washing, the membranes were incubated with appropriate secondary antibodies (Li-Cor) for one hour at room temperature. The secondary antibody was imaged using the Odyssey direct infrared fluorescence imaging system (Li-Cor) and densitometrically quantified with LiCor Odyssey software v2.1 at 800 and 680 nm wavelengths.

Rabbit Bilateral Jugular Vein Graft Interposition Model

Male New Zealand White rabbits (3.0-3.5 kg; n=24) were anesthetized through an intramuscular injection with ketamine hydrochloride (1.4 mg/kg) and xylazine (0.2 mg/kg). Anesthesia was maintained with endotracheal intubation and inhaled isoflurane (2.0-5.0%). A high-dose IV heparin bolus (250 U/kg) was administered immediately prior to carotid cross clamp. The operative procedure was performed with aseptic technique under optical magnification (magnification×2.5).

Vein bypass grafts were constructed with an anastomotic cuff technique as previously described. Briefly, polymer cuffs consisting of a 2.0-mm body loop were fashioned from a 4-Fr introducer sheath (Terumo Medical, Elkton, Md.). Following ligation of smaller tributary vessels, the external jugular veins were harvested (3.0-4.0 cm in length) for creation of an interposition graft into the common carotid artery. Jugular vein ends were passed through a cuff, everted, and fixed with 6-0 silk. Vein grafts were subsequently treated for 30 minutes in 2 mL of Heparin Plasma-Lyte solution containing either 30 μM MK2i-NP, 30 μM MK2i peptide, or PBS (no treatment). Following treatment, the carotid artery lumen was exposed with a 2.0-cm arteriotomy, and the cuffed, reversed vein ends were inserted. A 3-0 silk was used to secure the artery around the cuff Finally, 1.0 cm of carotid artery back wall was cut away between the cuffs to permit vein graft extension.

Rabbits were euthanized at 28 days post-operatively, and vein grafts were perfusion fixed in situ with 10% neutral buffered formalin under ~50 mm Hg pressure with a roller pump. Vein grafts were subsequently excised and sectioned into four segments avoiding the tissue overlying the cuff in order to allow for evaluation of morphological variation along the length of the graft. Histological sections were prepared, and intimal and medial thicknesses were quantified by taking three measurements from each quadrant of each vessel section (12 measurements/segment=48 measurements/graft). Separate sections were stained with the rabbit macrophage antibody RAM-11 (Dako) to evaluate treatment effect on the infiltration of immune cells into the intima of each graft. Macrophage positive staining in the intima was quantified by manually counting the number of positively stained cells in the intima of stained graft sections. Histological images from different graft sections were analyzed for each treatment group.

Statistics

Statistical analysis was performed with one-way ANOVA followed by Tukey's post-hoc test to compare experimental groups. Analyses were done with OriginPro 8 software (Originlab, Northampton, Mass.) or Minitab 16 software (State College, Pa.). Statistical significance was accepted within a 95% confidence limit. Results were presented as arithmetic mean±SEM graphically and p-values are included within figures or in the figure legends.

Additional Supporting Data

Figure 48:
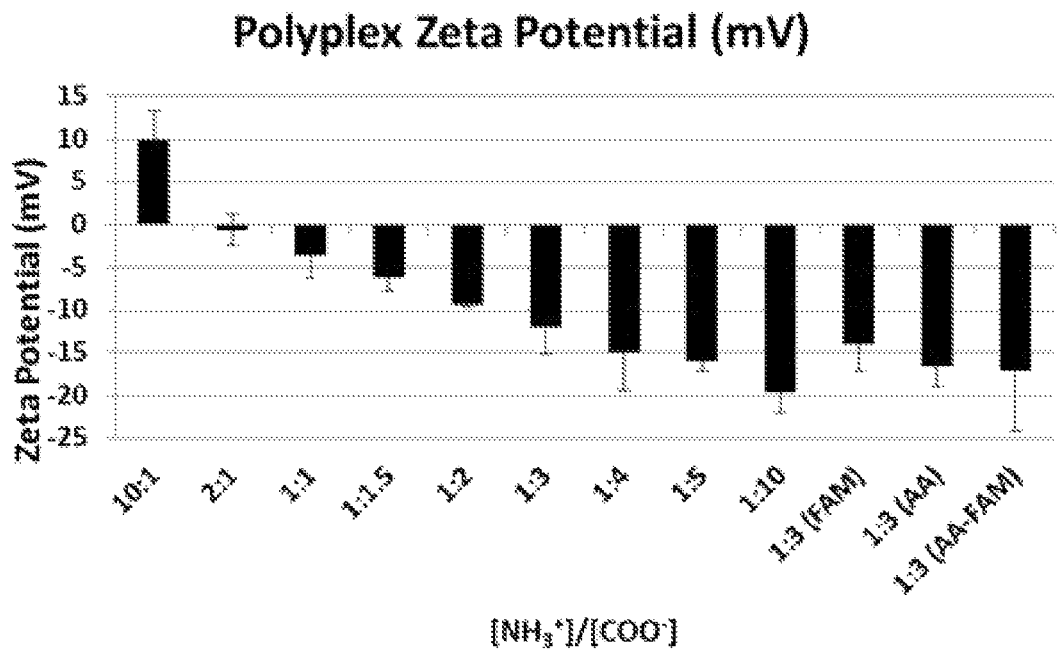
FIG. 48 shows ζ-potential of polyplexes prepared at different charge ratios ([NH$_3^+$]/[COO$^-$]) determined on a Zetasizer Nano ZS. Values shown are an average of at least three independent measurements.

FIG. 48 shows ζ-potential of polyplexes prepared at different charge ratios ([$NH_3^+$]/[$COO^-$]) determined on a Zetasizer Nano ZS. Values shown are an average of at least three independent measurements.

Figure 49:
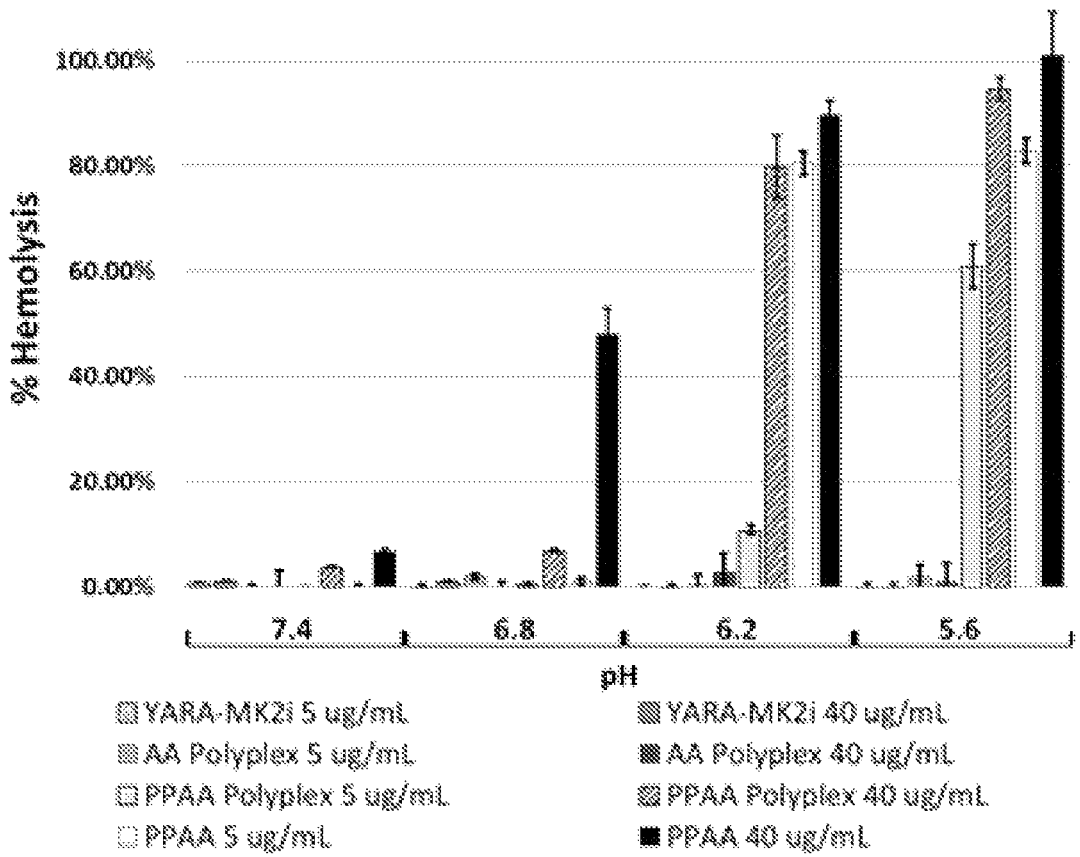
FIG. 49 illustrates pH-dependent hemolysis of polyplexes prepared at a charge ratio of [NH$_3^+$]/[COO$^-$]=1:3. Significant hemolysis was demonstrated at pH values representative of early to late endosomal vesicles (i.e. pH<6.8), whereas no significant hemolysis was seen at a physiologic pH of 7.4. Neither the YARA-MK2i peptide alone or AA polyplexes showed any significant hemolysis at any pH value tested PH-dependent size changes of polyplexes prepared at a charge ratio of [NH$_3^+$]/[COO$^-$]=1:3 were analyzed through DLS analysis.

Polyplex pH-dependent membrane disruptive behavior was tuned for endosomal escape to promote cytoplasmic peptide delivery and retention. FIG. 49 illustrates pH-dependent hemolysis of polyplexes prepared at a charge ratio of [$NH_3^+$]/[$COO^-$]=1:3. Significant hemolysis was demonstrated at pH values representative of early to late endosomal vesicles (i.e. pH<6.8), whereas no significant hemolysis was seen at a physiologic pH of 7.4. Neither the YARA-MK2i peptide alone or AA polyplexes showed any significant hemolysis at any pH value tested PH-dependent size changes of polyplexes prepared at a charge ratio of [$NH_3^+$]/[$COO^-$]=1:3 were analyzed through DLS analysis.

Figure 50:
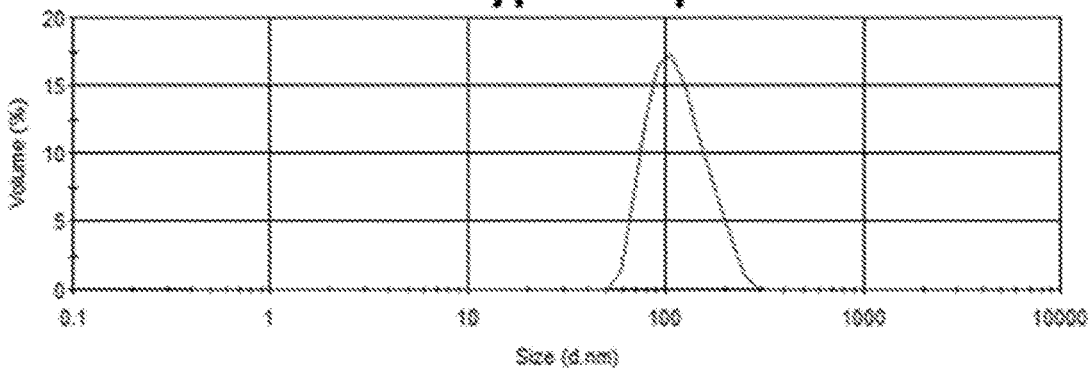
FIG. 50 illustrates that polyplexes at pH 7.4 show a unimodal size distribution. Upon decreasing pH, the polyplexes begin to dissociate into individual YARA-MK2i peptide and PPAA polymer unimers, as shown.
Figure 50:
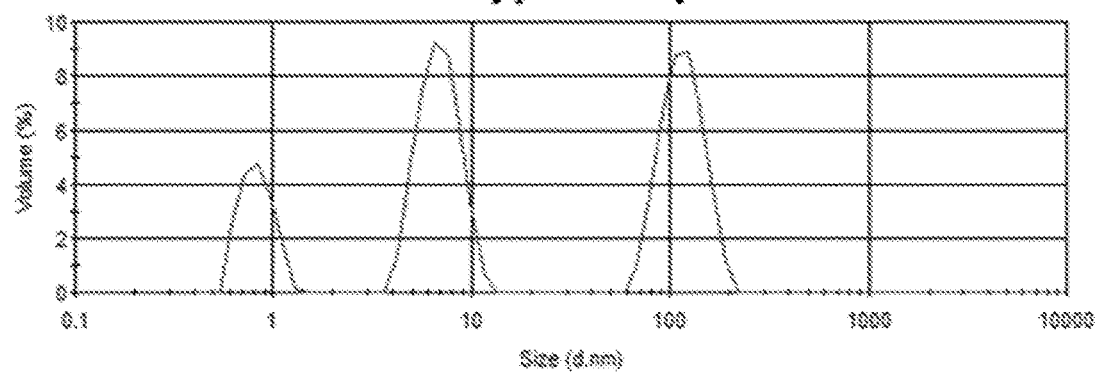
Figure 50:
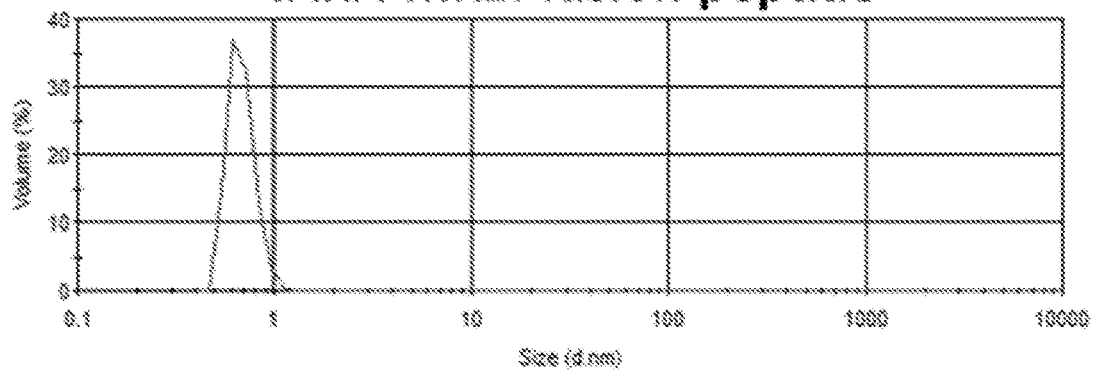
Figure 50:
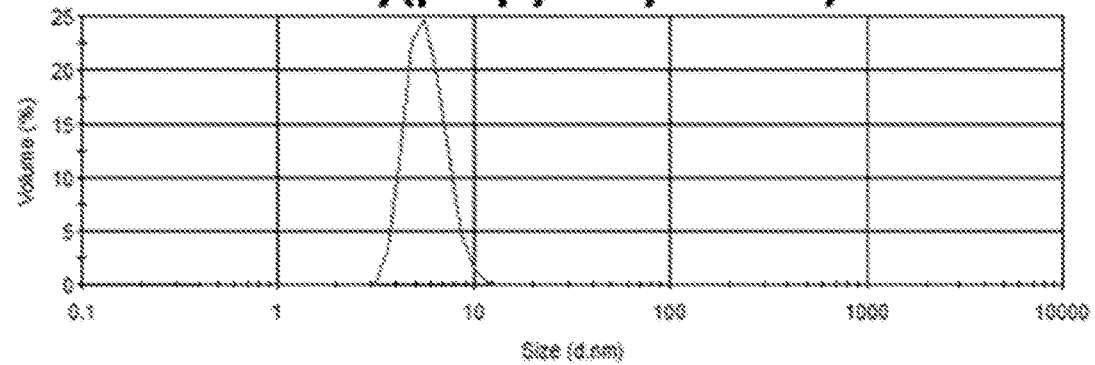

FIG. 50 illustrates that polyplexes at pH 7.4 show a unimodal size distribution. Upon decreasing pH, the polyplexes began to dissociate into individual YARA-MK2i peptide and PPAA polymer unimers.

Figure 51:
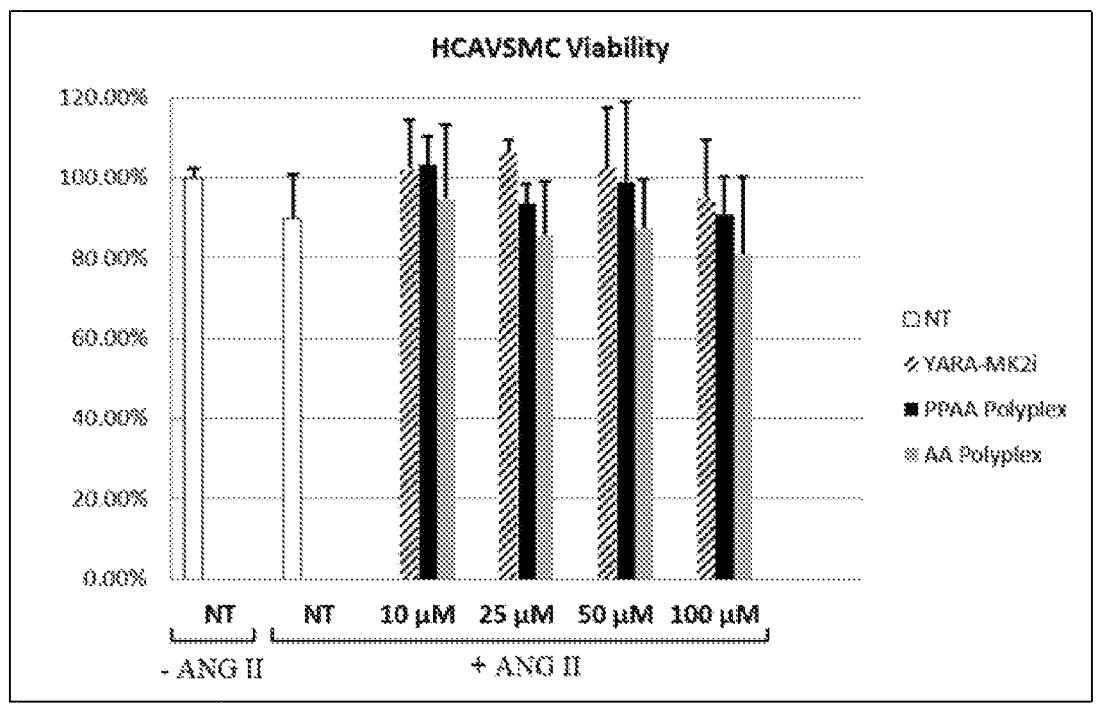
FIG. 51 shows viability of HCAVSMCs that were stimulated with 10 μM ANG II for 6 hours, treated for two hours with PPAA polyplexes, AA polyplexes, or YARA-MK2i peptide alone and cultured for 24 hours in fresh media. "NT" means no treatment, n=4.

Polyplex treatments did not have a significant effect on cell viability in human coronary artery vascular smooth muscle cells (HCAVSMCs). FIG. 51 shows viability of HCAVSMCs that were stimulated with 10 µM ANG II for six hours, treated for two hours with PPAA polyplexes, AA polyplexes, or YARA-MK2i peptide alone and cultured for 24 hours in fresh media. NT=no treatment, n=4.

Figure 52:
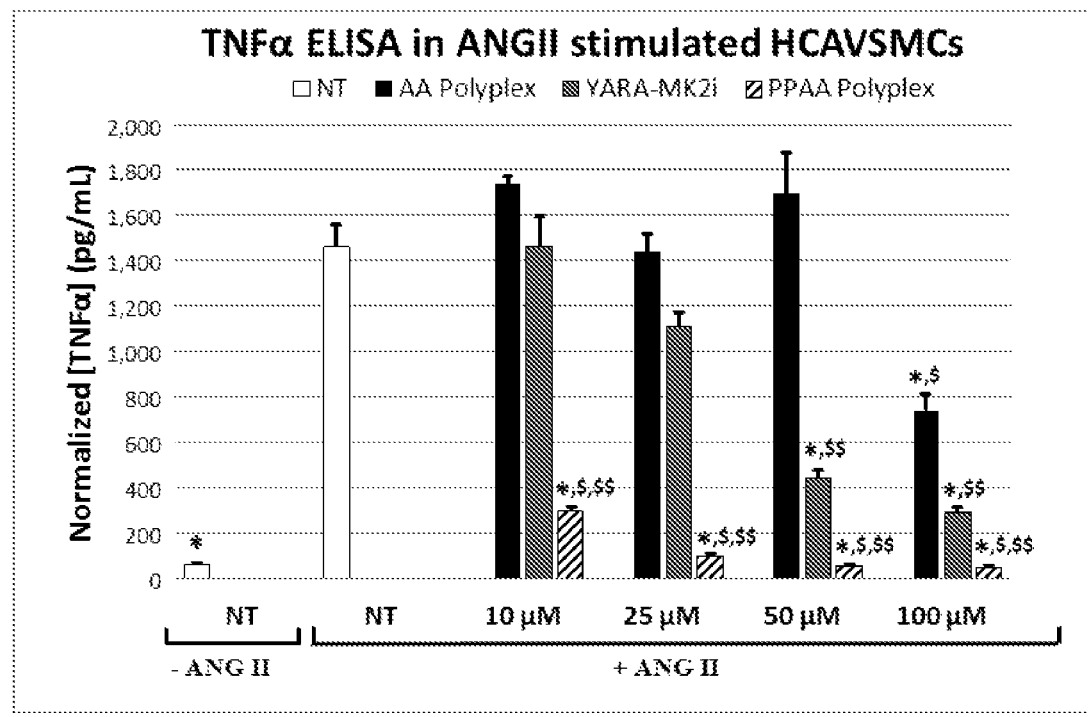
FIG. 52 shows TNF-α production in HCAVSMCs that were stimulated with ANG II for 6 hours, treated for two hours with PPAA polyplexes, AA polyplexes, or the fusion MK2i peptide alone and cultures for 24 hours in fresh media. Treatments were normalized to peptide concentrations of 10, 25, 50, or 100 μM. All data is normalized to cell number as determined by an LDH assay. NT=no treatment. *p<0.05 compared to NT+TNFα group, *p<0.05 compared to MK2i at the same concentration, **p<0.05 compared to AA polyplexes at the same concentration.

FIG. 52 shows TNF-α production in HCAVSMCs that were stimulated with ANG II for 6 hours, treated for two hours with PPAA polyplexes, AA polyplexes, or the fusion MK2i peptide alone and cultures for 24 hours in fresh media. Treatments were normalized to peptide concentrations of 10, 25, 50, or 100 µM. All data was normalized to cell number as determined by an LDH assay. NT=no treatment. $*p<0.05$ compared to NT+TNFα group, $*p<0.05$ compared to MK2i at the same concentration, $**p<0.05$ compared to AA polyplexes at the same concentration.

Figure 53:
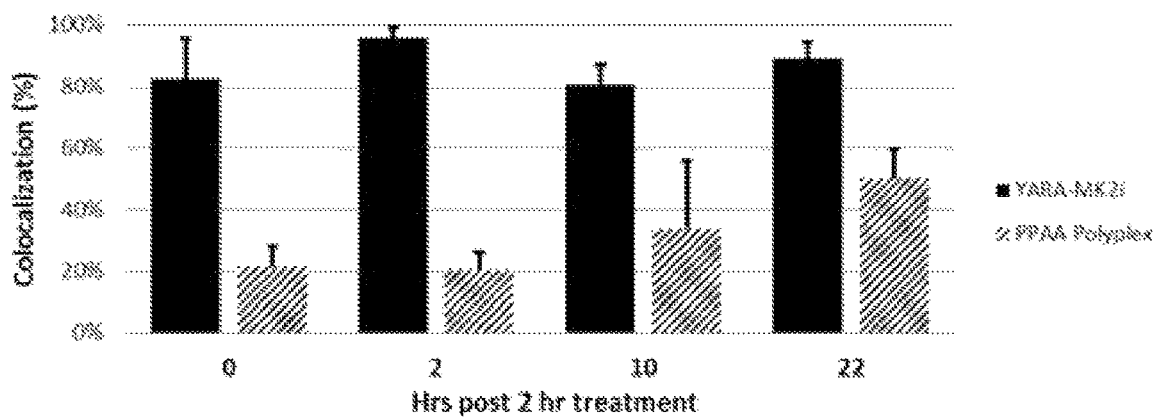
FIG. 53 shows percentage(s) of colocalization of green fluorophore with red fluorophore, determined through the calculation of Mander's coefficient, M1 (essentially the % of green fluorescence in the image that overlaps red fluorescence, i.e. the % of peptide contained within endosomal vesicles). The YARA-MK2i dose is 25 μM for all samples. Values shown are the average n=3 separate images±SEM. *p<0.05 compared to YARA-MK2i at the same time point, **p<0.01 compared to YARA-MK2i at the same time point. This graph is the result of microscopic analysis of HCAVSMC polyplex uptake, and it shows that the polyplexes enhance uptake and endosomal escape of the MK2i peptide.
Figure 54:
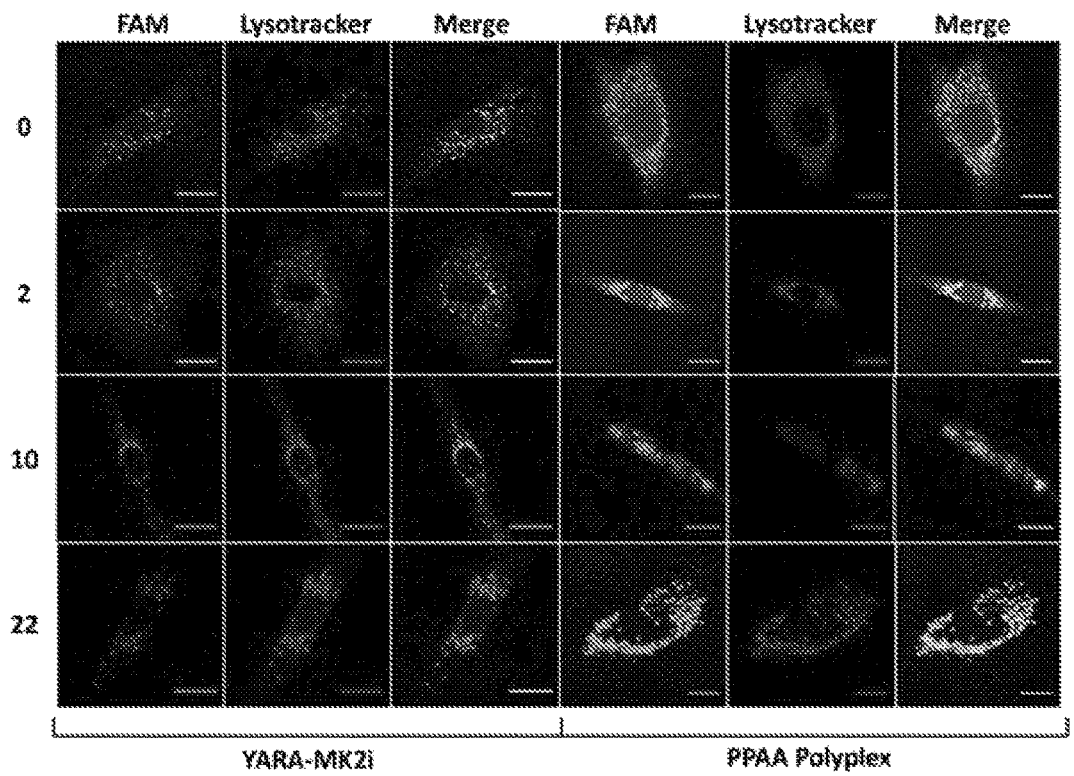
FIG. 54 relates to the data in FIG. 53 and provides representative fluorescence images used to quantify colocalization. The numbers on the left represent the amount of time the cells were incubated in fresh media following two hours of treatment, the gain for both the red and green channels was kept constant for all images obtained.

Microscopic analysis of HCAVSMCs polyplex uptake shows that the polyplexes enhanced uptake and endosomal escape of the MK2i peptide. The peptide was labeled with a green fluorophore for tracking purposes. Prior to cell imaging, the cells were treated with a red LysoTracker® dye that marked intracellular vesicles in the endo-lysosomal pathway. This analysis was done to assess the ability of the polyplexes to enhance escape from the endo-lysosomal trafficking pathways relative to cells treated with the free peptide. FIG. 53 shows percentage of colocalization of green fluorophore with red fluorophore determined through the calculation of Mander's coefficient, M1 (essentially the % of green fluorescence in the image that overlaps red fluorescence, i.e. the % of peptide contained within endosomal vesicles) YARA-MK2i dose=25 µM for all samples. Values shown are the average n=3 separate images±SEM. $*p<0.05$ compared to YARA-MK2i at the same time point, $**p<0.01$ compared to YARA-MK2i at the same time point. This graph is the result of microscopic analysis of HCAVSMC polyplex uptake, and it shows that the polyplexes enhance uptake and endosomal escape of the MK2i peptide.

Figure 55:
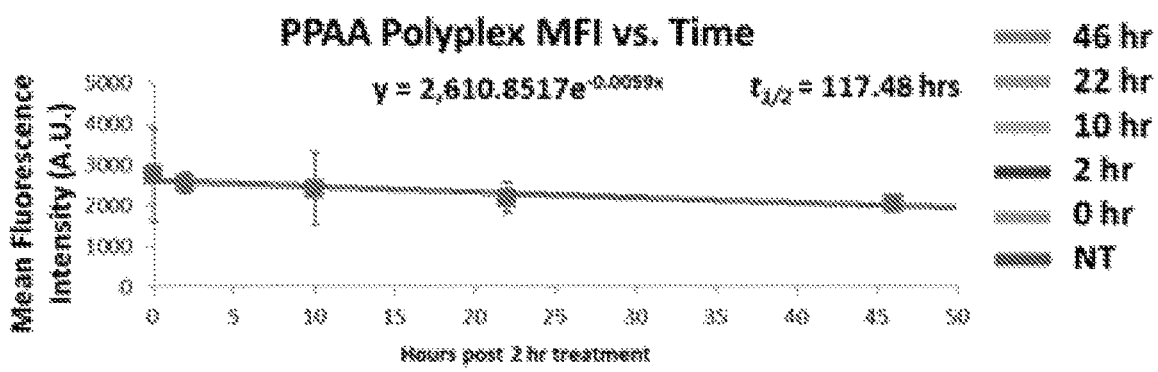
FIG. 55 shows a plot of mean fluorescence intensity over time for PPAA polyplexes.
Figure 56:
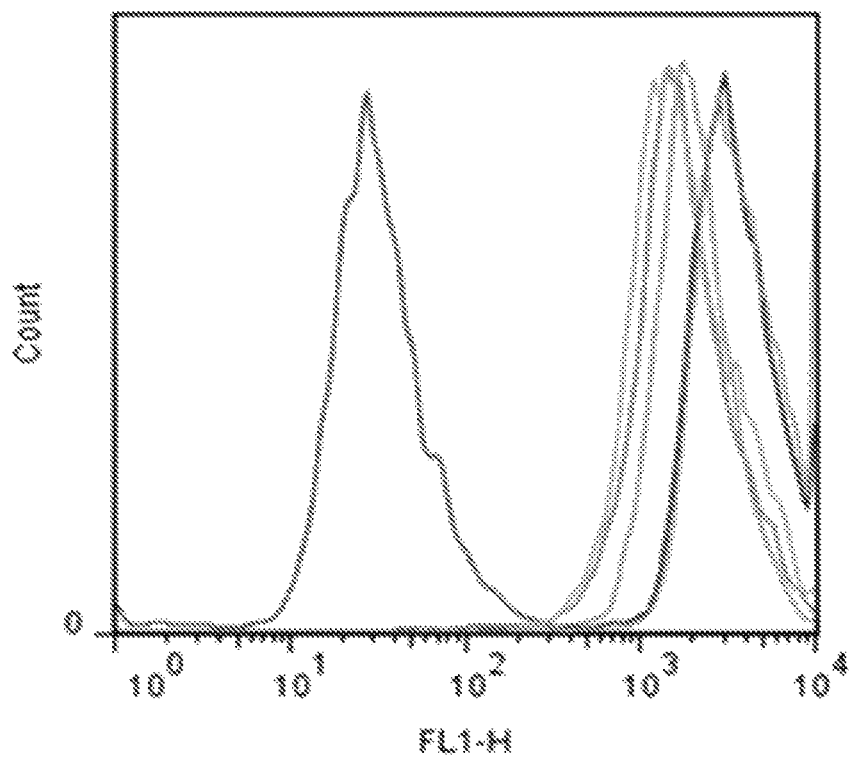
FIG. 56 provides a histogram of fluorescence intensity over time for PPAA polyplexes.
Figure 57:
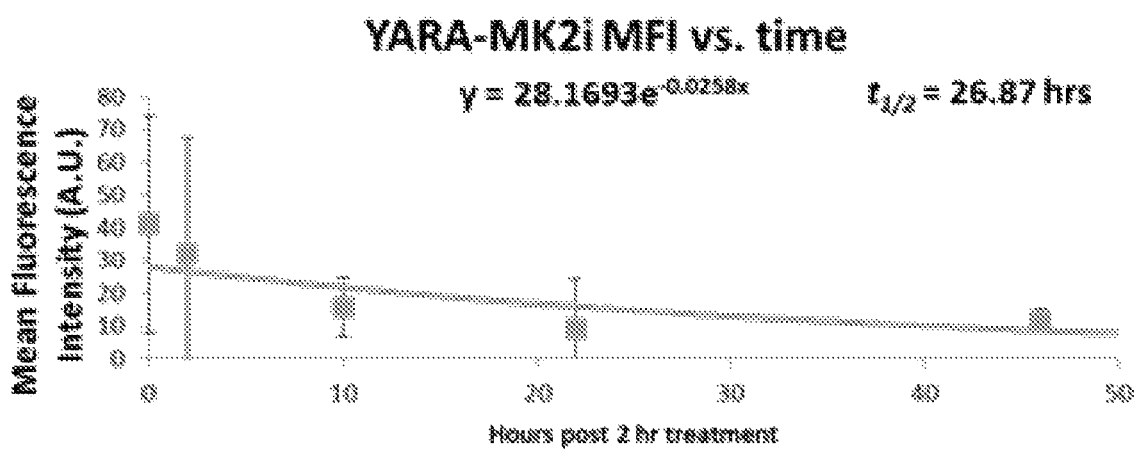
FIG. 57 presents a plot of mean fluorescence intensity over time for the YARA-MK2i peptide alone.
Figure 58:
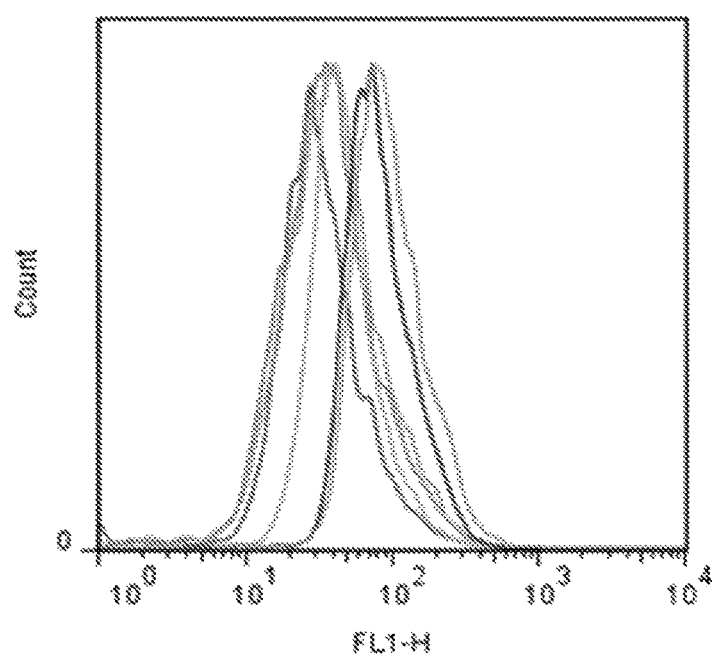
FIG. 58 is a histogram of fluorescence intensity over time for the YARA-MK2i peptide alone.
Figure 59:
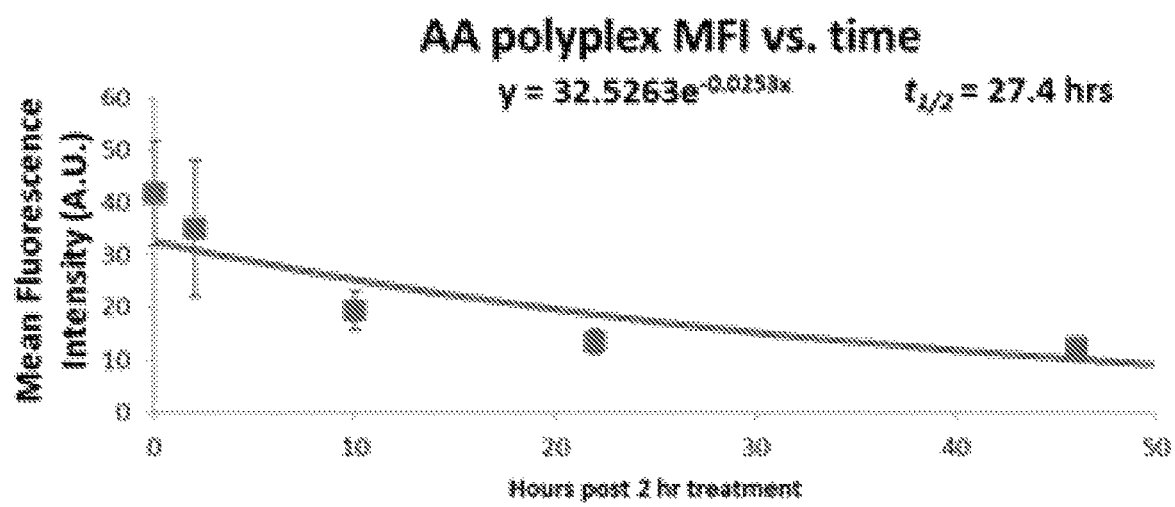
FIG. 59 is a plot of mean fluorescence intensity over time for AA polyplexes.
Figure 60:
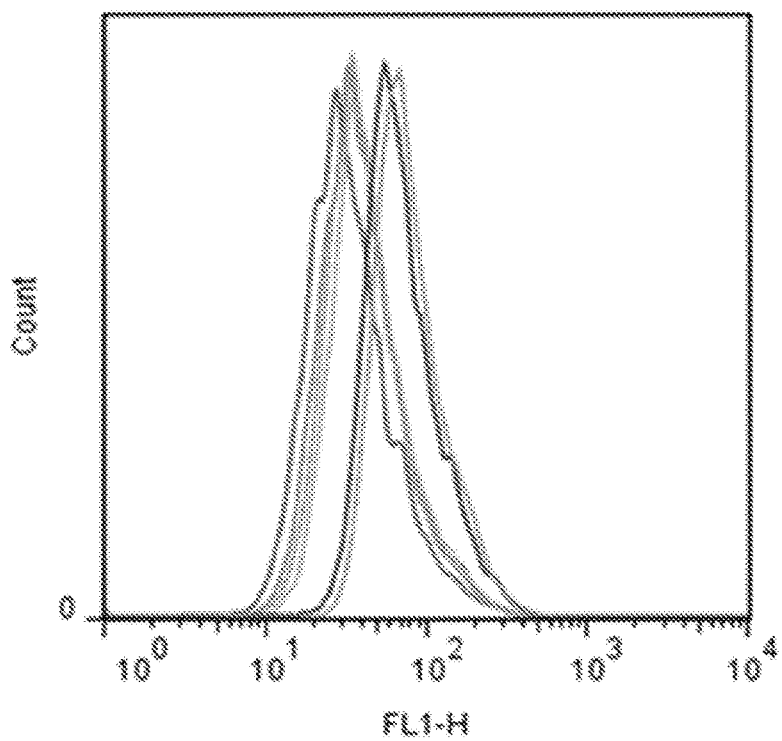
FIG. 60 provides a histogram of fluorescence intensity over time for AA polyplexes.

Peptide uptake and intracellular half-life was significantly enhanced in HCAVSMCs when delivered via the novel polyplex formulation. Studies were done using a fluorescently labeled peptide and flow cytometry. Plots of mean fluorescence intensity over time and histograms of fluorescence intensity over time for PPAA polyplexes (FIG. 55, FIG. 56), the YARA-MK2i peptide alone (FIG. 57, FIG. 58), and AA polyplexes (FIG. 59, FIG. 60) were prepared. Exponential lines were fit to each data set in order to determine a fluorescence half-life for each treatment group. Mean Fluorescence Intensity values were reported as increase in MFI compared to untreated controls, n=3.

Figure 61:
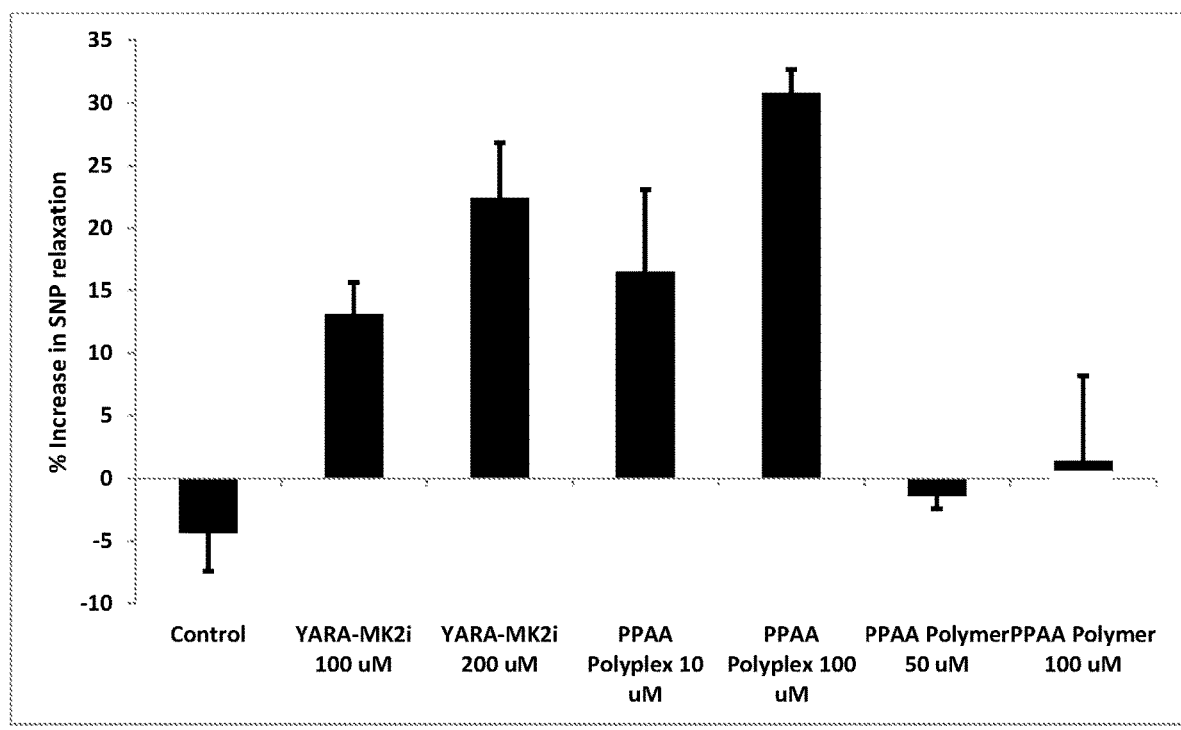
FIG. 61 provides a bar graph showing percentage increase in sodium nitroprusside (SNP) relaxation after HSV rings were contracted with phenylephrine (PE, 10$^{-6}$ M) and subsequently relaxed with SNP ($10^{-8}$-$10^{-6}$ M). HSV rings were then treated for two hours and contracted again with PE and relaxed with SNP to determine post-treatment increase in relaxation. Following post-treatment contraction, all rings were contracted with KCl to verify smooth muscle viability. *p<0.05 compared to control, **p<0.05 compared to 100 μM MK2i, n=3.

Polyplexes more potently enhance HSV vasorelaxation compared to treatment with the free peptide. Polyplexes significantly enhanced sodium nitroprusside (SNP) induced relaxation of human saphenous vein explants. HSV rings were contracted with phenylephrine (PE, $10^{-6}$ M) and subsequently relaxed with SNP ($10^{-8}$-$10^{-6}$ M). HSV rings were then treated for two hours and contracted again with PE and relaxed with SNP to determine post-treatment increase in relaxation. Following post-treatment contraction, all rings were contracted with KCl to verify smooth muscle viability. $*p<0.05$ compared to control, $**p<0.05$ compared to 100 uM MK2i, n=3, as shown in FIG. 61.

Figure 62:
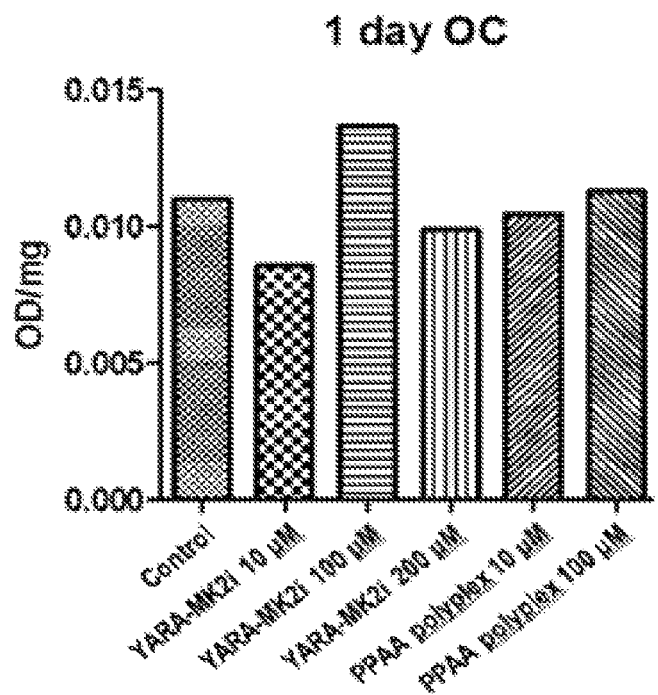
FIG. 62 shows cell viability in HSV rings treated for 2 hours and maintained in organ culture for 24 hours assessed through an MTT assay. n=1.
Figure 63:
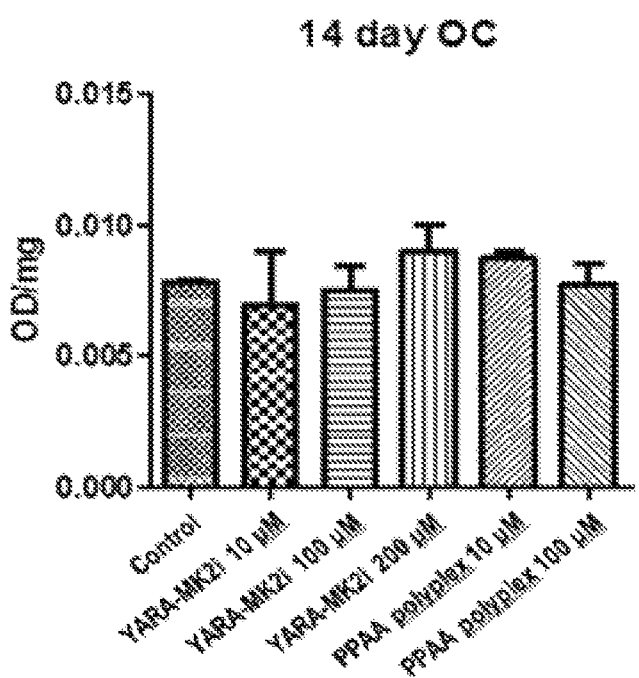
FIG. 63 shows cell viability in HSV rings treated for 2 hours and maintained in organ culture for 14 days as assessed through an MTT assay. n=1.

FIG. 62 shows cell viability in HSV rings treated for two hours and maintained in organ culture for 24 hours assessed through an MTT assay. n=1. FIG. 63 shows cell viability in HSV rings treated for two hours and maintained in organ culture for 14 days as assessed through an MTT assay. n=1.

Figure 64:
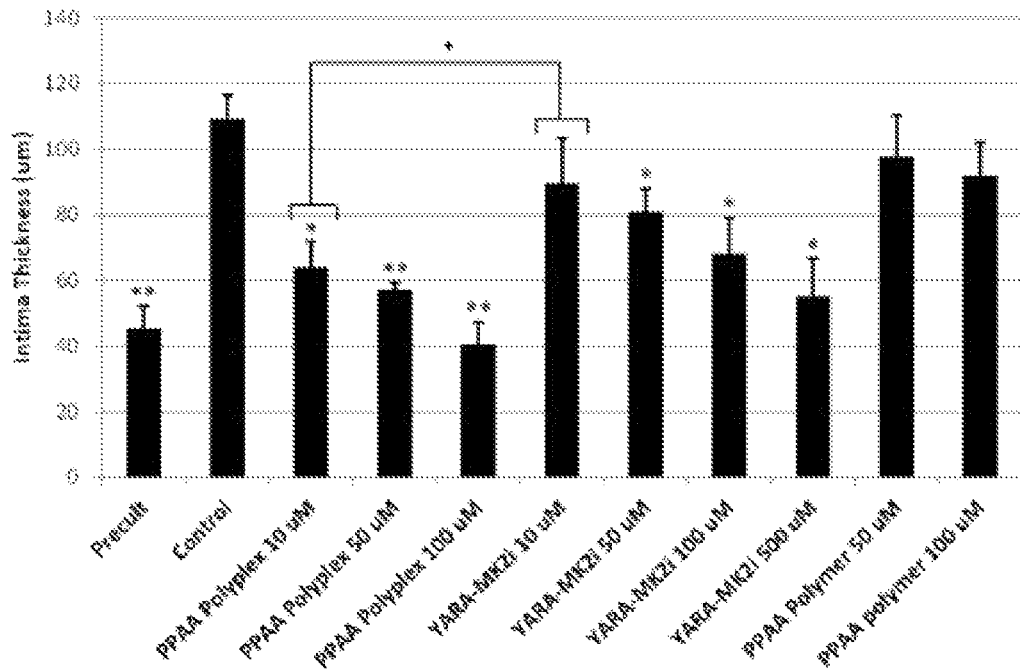
FIG. 64 displays intimal thickness of HSV explants treated for 2 hours and then maintained in organ culture for 14 days, n=3. *p≤0.01 compared to control (untreated), **p≤0.001 compared to control, $^\dagger$p ≤0.05.

FIG. 64 displays intimal thickness of HSV explants treated for two hours and then maintained in organ culture for 14 days, n=3. $*p\leq0.01$ compared to control (untreated), $**p\leq0.001$ compared to control, $^{\dagger}p\leq0.05$.

Figure 65:
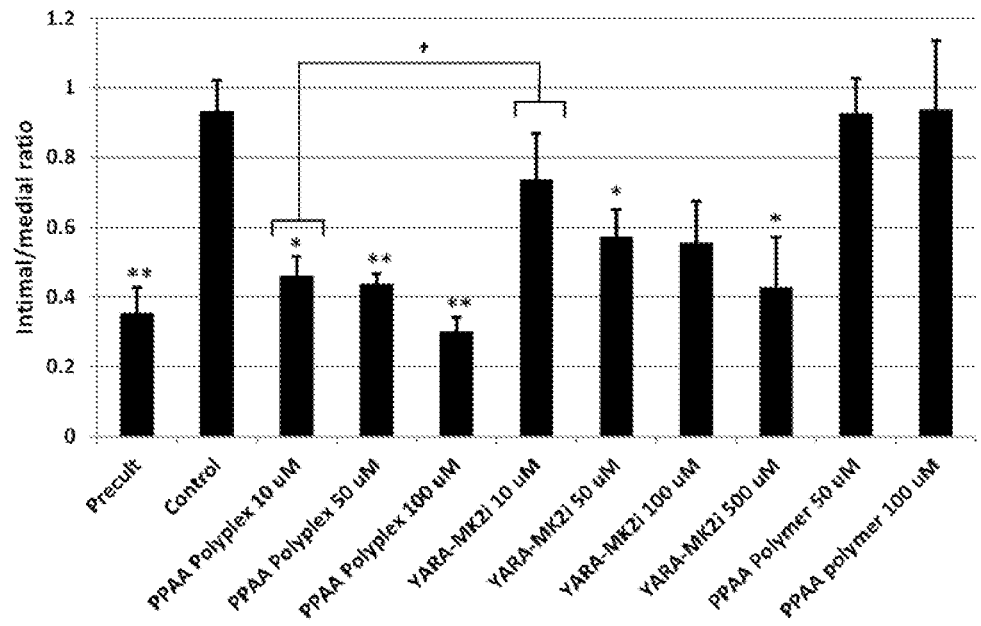
FIG. 65 provides a plot of the Intimal/Medial (I/M) ratio of HSV explants treated for two hours and then maintained in organ culture for 14 days, n=3. *p≤0.01 compared to control (untreated), **p≤0.001 compared to control, $^\dagger$p ≤0.05.

FIG. 65 provides a plot of the Intimal/Medial (I/M) ratio of HSV explants treated for two hours and then maintained in organ culture for 14 days, n=3. $*p\leq0.01$ compared to control (untreated), $**p\leq0.001$ Example 7

AZX-100 Polyplex Characterization Summary

Figure 66:
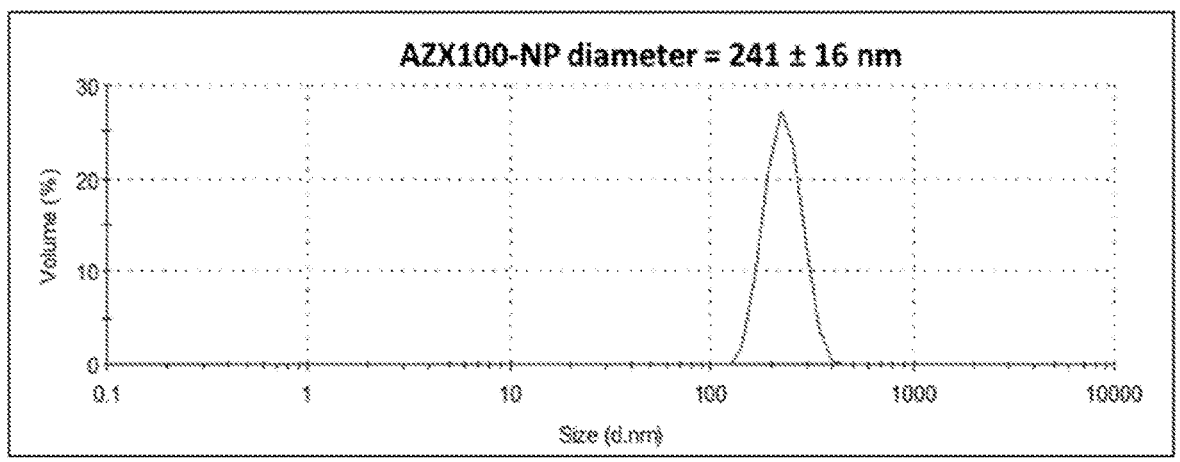
FIG. 66 shows a DLS size distribution of AZX-100 polyplexes prepared at a 3:1 charge ratio.
Figure 67:
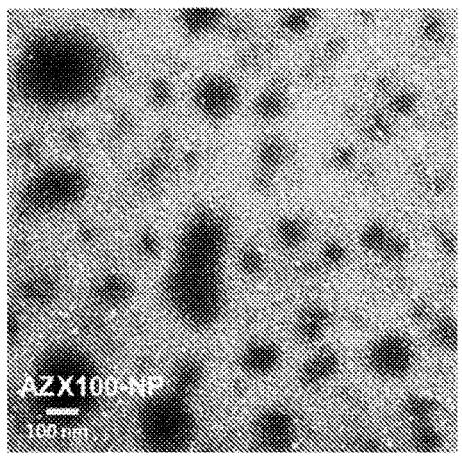
FIG. 67 provides a representative TEM image of uranyl acetate stained AZX-100 polyplexes showing a size distribution in agreement with DLS results.
Figure 68:
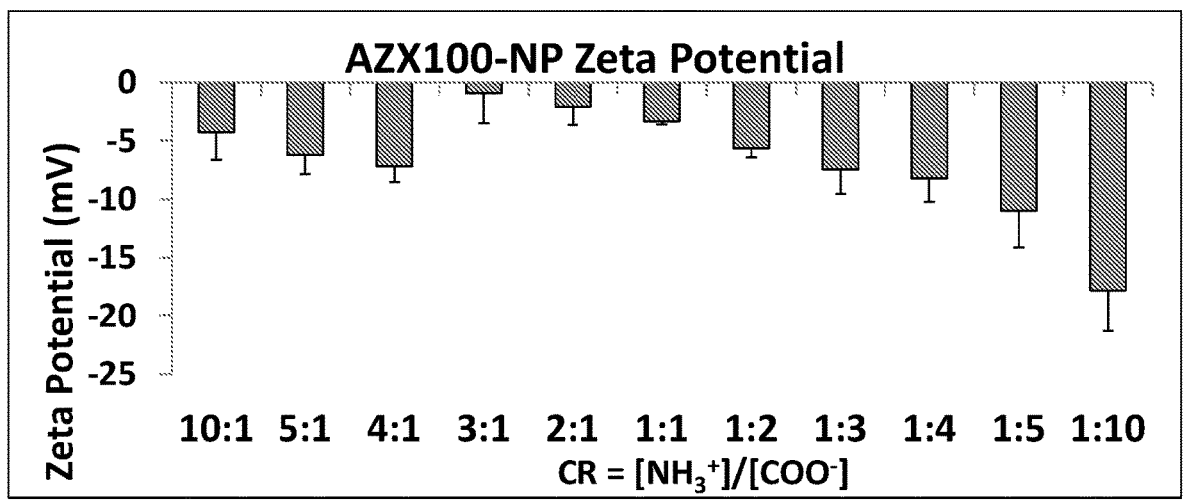
FIG. 68 provides a summary of zeta potential for AZX-100 polyplexes prepared at various charge ratios. Zeta potential was found to be directly proportional to charge ratio at charge ratios higher than 3:1. An unexpected shift in zeta potential was seen at a charge ratio of 3:1, possibly due to macromolecular rearrangement.

FIG. 66 provides a DLS size distribution of AZX-100 polyplexes prepared at a 3:1 charge ratio. FIG. 67 is a representative TEM image of uranyl acetate stained AZX-100 polyplexes showing a size distribution in agreement with DLS results. FIG. 68 is a zeta potential summary of AZX-100 polyplexes prepared at various charge ratios. Zeta potential was found to be directly proportional to charge ratio at charge ratios higher than 3:1. An unexpected shift in zeta potential is seen at a charge ratio of 3:1, possibly due to macromolecular rearrangement.

Figure 69:
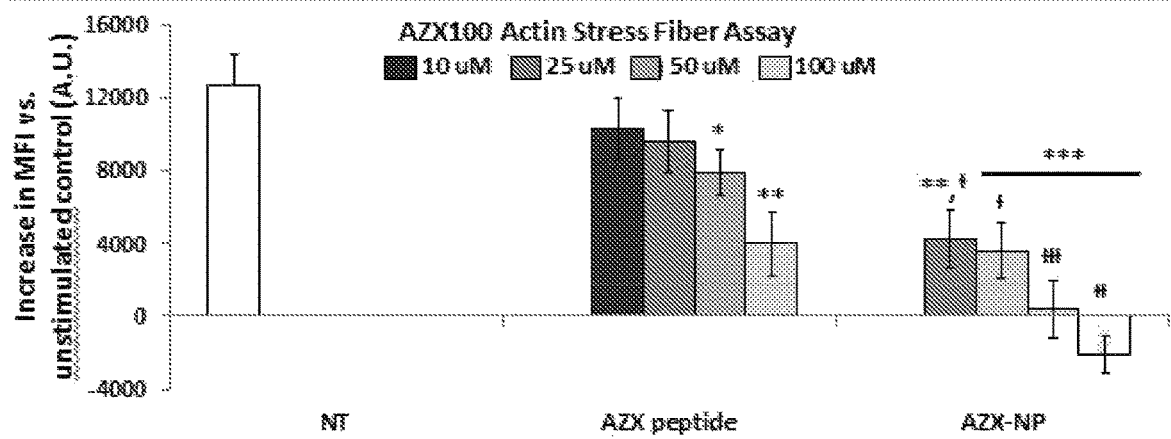
FIG. 69 and FIG. 70 show that AZX-100 polyplexes enhance AZX-100 mediated inhibition of stress fiber formation in angiotensin II stimulated human coronary artery vascular smooth muscle cells. Cells were treated for one hour and then subsequently stimulated with angiotensin II for 2 hours. Actin stress fibers were visualized in phalloidin stained, fixed samples and relative fluorescent intensity of individual cells from each treatment group was utilized to quantify actin stress fiber formation.
Figure 70:
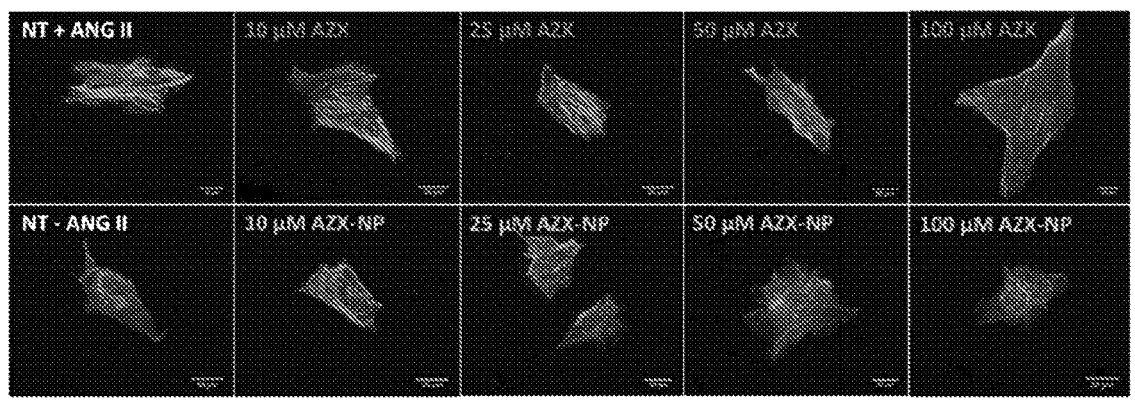

AZX-100 polyplexes enhanced AZX-100 mediated inhibition of stress fiber formation in angiotensin II stimulated human coronary artery vascular smooth muscle cells. Cells were treated for one hour and then subsequently stimulated with angiotensin II for two hours. Actin stress fibers were visualized in phalloidin stained, fixed samples and relative fluorescent intensity of individual cells from each treatment group was utilized to quantify actin stress fiber formation. FIG. 69 and FIG. 70 show that AZX-100 polyplexes enhanced AZX-100 mediated inhibition of stress fiber formation in angiotensin II stimulated human coronary artery vascular smooth muscle cells.

Figure 71:
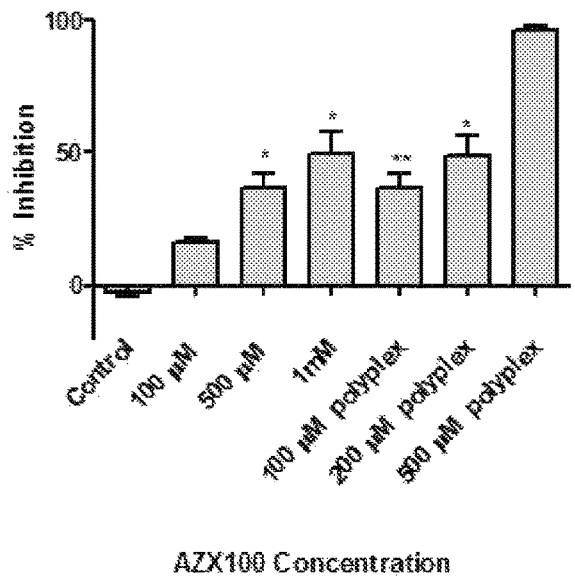
FIG. 71 presents the percent of inhibition that occurred in rat aortic smooth muscle that was treated with control, AZ100 peptide or AZX polyplexes.
Figure 72:
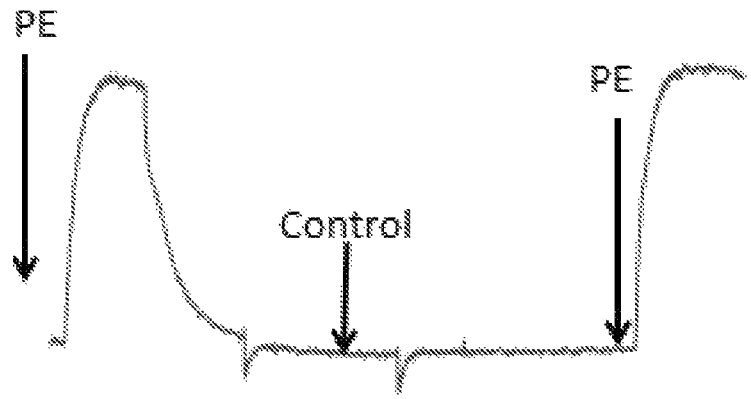
FIG. 72 shows the contraction of rat aortic smooth muscle.
Figure 73:
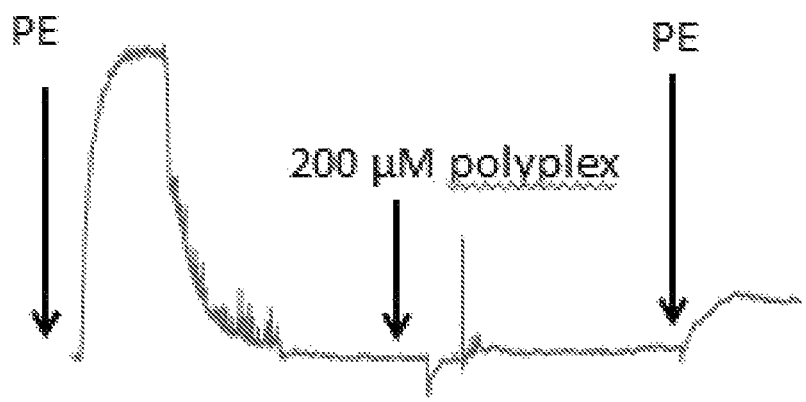
FIG. 73 shows the dose-dependent inhibition of contraction in rat aortic smooth muscle that was treated with an AZX polyplex.

FIGS. 71-73 show the results of an example wherein rat aortic smooth muscle was suspended on a muscle bath apparatus. Tissue was equilibrated in bicarbonate buffer and challenged with KCl (110 mM) to confirm viability of the tissue. After returning the tissue to basal tension, the smooth muscle was challenged with $5*10^{-8}$ M phenylephrine ($5*10^{-8}$ M) and then washed with bicarbonate buffer. The tissue was then returned to basal tension through subsequent washes of bicarbonate buffer and then either treated with control, AZX 100 peptide, or AZX polyplexes. After 30 minutes of incubation, the tissue was challenged with phenylephrine, and the contractile force was compared with the initial contraction to determine the percent inhibition that occurs. The AZX 100 peptide showed a dose dependent inhibition of contraction when added to rat aortic smooth muscle. The AZX polyplex also had a dose dependent inhibition of contraction but had a greater inhibition (approximate 5-fold increase) of contraction for comparable doses. (n=6)

Figure 74:
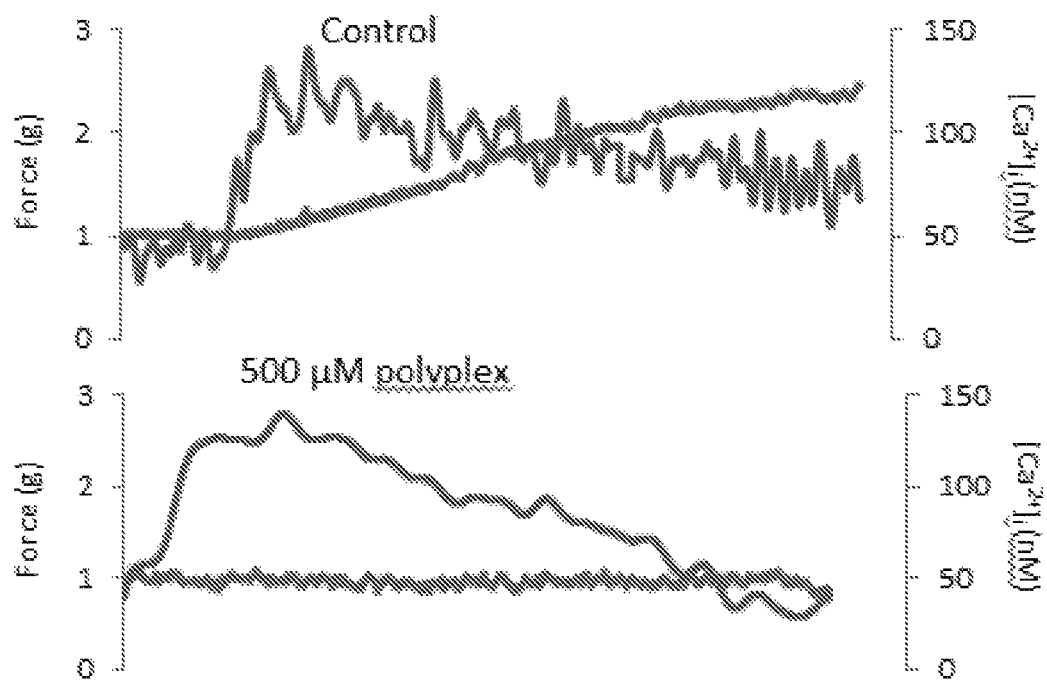
FIG. 74 displays a representative tracing of force and calcium fluorescence tracings in rat aortic smooth muscle.
Figure 75:
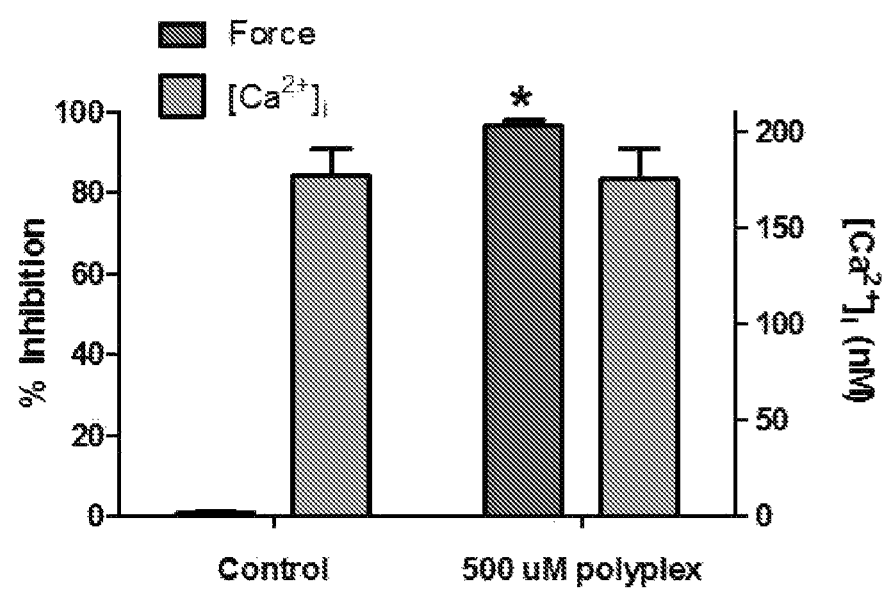
FIG. 75 provides cumulative data measuring the magnitude of change in intracellular calcium and the inhibition of force that occurred in rat aortic smooth muscle.

FIG. 74 and FIG. 75 show the results of an example wherein aortic smooth muscle was suspended on a Fluoroplex. Tissue was equilibrated in bicarbonate buffer and loaded with 5 µM Fura 2-AM for 4 hours at room temperature. Preincubation with AZX polyplex does not inhibit a rise in intracellular calcium when challenged with phenylephrine. FIG. 74 displays a representative tracing of force and calcium fluorescence tracings. FIG. 75 provides cumulative data measuring the magnitude of change in intracellular calcium and the inhibition of force that occurred.

Figure 76:
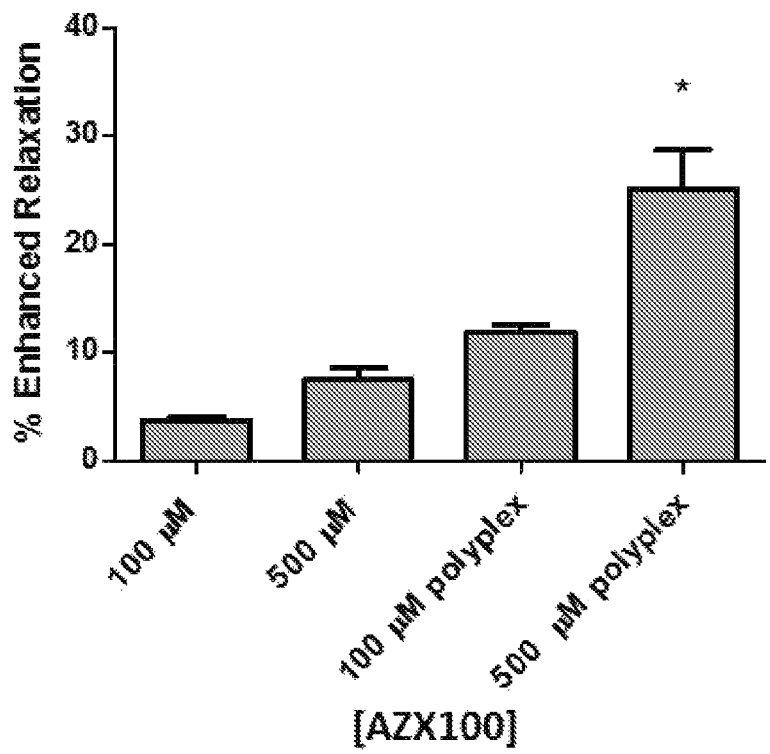
FIG. 76 shows the % enhanced relaxation in HSV after treatment with AZX-100 peptide or AZX polyplexes at different concentrations.

FIG. 76 provides the results of an example wherein human saphenous vein was suspended on a muscle bath apparatus. Tissue is equilibrated in bicarbonate buffer and challenged with KCl (110 mM) to confirm viability of the tissue. After returning the tissue to basal tension the smooth muscle was challenged with $10^{-6}$ M phenylephrine and then relaxed with sodium nitroprusside ($10^{-7}$ M). The tissue was then returned to basal tension through subsequent washes of bicarbonate buffer and then either treated with control, AZX 100 peptide, or AZX polyplexes. After 30 minutes of incubation the tissue was challenged with phenylephrine and then relaxed with sodium nitroprusside. The percent relaxation was compared with the initial relaxation to determine the percent enhanced relaxation. The AZX 100 peptide showed a dose dependent enhancement of relaxation compared to control. The AZX polyplex also had a dose dependent enhancement of relaxation, but demonstrated greater relaxation (approximate 5-fold increase) compared to the peptide alone. (n=3).

Figure 77:
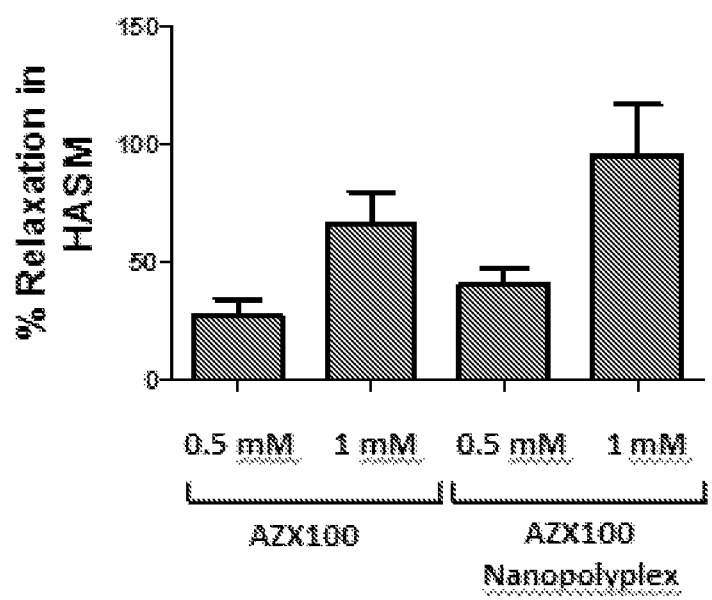
FIG. 77 illustrates that AZX-100 NPs enhance AZX-100 mediated relaxation of human bronchiolar airway smooth muscle.
Figure 78:
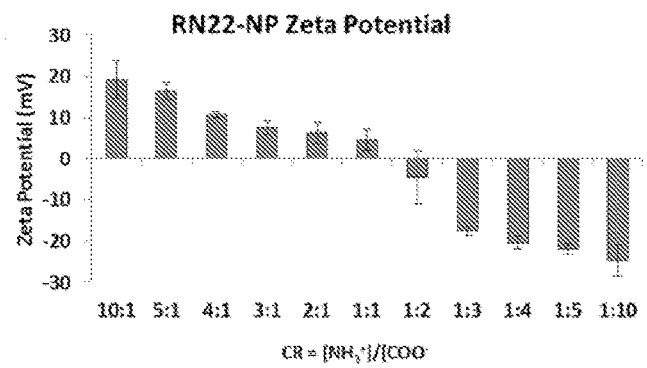
FIG. 78 provides a table and chart showing the effects of different charge ratios on the diameter, polydispersity index (PDI), and zeta potential of RN22-containing polyplexes.
Figure 79:
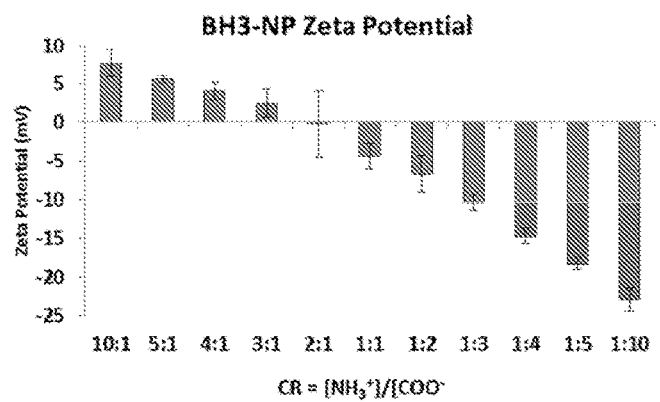
FIG. 79 provides a table and chart showing the effects of different charge ratios on the diameter, polydispersity index (PDI), and zeta potential for Penetratin-BAK-BH3-containing polyplexes.

Finally, FIG. 77 and Table 2, taken together, illustrate that AZX-100 NPs enhance AZX-100 mediated relaxation of human bronchiolar airway smooth muscle (HASM).

TABLE 2

Relaxation of HASM.

| | HASM 11 | HASM 17 | HASM 18 | HASM 20 | HASM 22 |
|---|---|---|---|---|---|
| p20 .5 mM | 24 | 10 | | 36 | 40 |
| p20 1 mM | | 25 | 80 | 76 | 84 |
| p-P20 .5 mM-polyplex | 37 | 31 | 59 | | 38 |
| p-P20 1 mM-polyplex | | | | 74 | 117 |

While the following terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a composition" includes a plurality of such compositions, and so forth.

Unless otherwise indicated, all numbers expressing quantities, properties, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

REFERENCES

Throughout this document, various references are mentioned. All such references, including those listed below, are incorporated herein by reference.

1. Go, A. S. et al. Heart disease and stroke statistics—2013 update: a report from the American Heart Association. *Circulation* 127, e6-e245 (2013).
2. Alexander, J. H. et al. Efficacy and safety of edifoligide, an E2F transcription factor decoy, for prevention of vein graft failure following coronary artery bypass graft surgery: PREVENT IV: a randomized controlled trial. *JAMA* 294, 2446-2454 (2005).
3. Saunders, P. C. et al. Vein graft arterialization causes differential activation of mitogen-activated protein kinases. *J Thorac Cardiovasc Surg* 127, 1276-1284 (2004).
4. Raingeaud, J. et al. Pro-inflammatory cytokines and environmental stress cause p38 mitogen-activated protein kinase activation by dual phosphorylation on tyrosine and threonine. *J Biol Chem* 270, 7420-7426 (1995).
5. Zarubin, T. & Han, J. Activation and signaling of the p38 MAP kinase pathway. *Cell Res* 15, 11-18 (2005).
6. Engel, K., Kotlyarov, A. & Gaestel, M. Leptomycin B-sensitive nuclear export of MAPKAP kinase 2 is regulated by phosphorylation. *EMBO J* 17, 3363-3371 (1998).
7. Xu, J. J., Hendriks, B. S., Zhao, J. & de Graaf, D. Multiple effects of acetaminophen and p38 inhibitors: towards pathway toxicology. *FEBS Lett* 582, 1276-1282 (2008).
8. Dambach, D. M. Potential adverse effects associated with inhibition of p38alpha/beta MAP kinases. *Curr Top Med Chem* 5, 929-939 (2005).
9. Ward, B., Seal, B. L., Brophy, C. M. & Panitch, A. Design of a bioactive cell-penetrating peptide: when a transduction domain does more than transduce. *Journal of Peptide Science* 15, 668-674 (2009).
10. Hayess, K. & Benndorf, R. Effect of protein kinase inhibitors on activity of mammalian small heat-shock protein (HSP25) kinase. *Biochem Pharmacol* 53, 1239-1247 (1997).
11. Lopes, L. B. et al. A novel cell permeant peptide inhibitor of MAPKAP kinase II inhibits intimal hyperplasia in a human saphenous vein organ culture model. *J Vasc Surg* 52, 1596-1607 (2010).
12. Flynn, C. R. et al. Internalization and intracellular trafficking of a PTD-conjugated anti-fibrotic peptide, AZX100, in human dermal keloid fibroblasts. *J Pharm Sci* 99, 3100-3121 (2010).
13. Jones, R. A. et al. Poly(2-alkylacrylic acid) polymers deliver molecules to the cytosol by pH-sensitive disruption of endosomal vesicles. *Biochem J* 372, 65-75 (2003).
14. Lackey, C. A., Press, O. W., Hoffman, A. S. & Stayton, P. S. A biomimetic pH-responsive polymer directs endosomal release and intracellular delivery of an endocytosed antibody complex. *Bioconjugate Chemistry* 13, 996-1001 (2002).
15. Murthy, N., Robichaud, J. R., Tirrell, D. A., Stayton, P. S. & Hoffman, A. S. The design and synthesis of polymers for eukaryotic membrane disruption. *J Control Release* 61, 137-143 (1999).
16. Foster, S., Duvall, C. L., Crownover, E. F., Hoffman, A. S. & Stayton, P. S. Intracellular delivery of a protein antigen with an endosomal-releasing polymer enhances CD8 T-cell production and prophylactic vaccine efficacy. *Bioconjug Chem* 21, 2205-2212 (2010).
17. Crownover, E., Duvall, C. L., Convertine, A., Hoffman, A. S. & Stayton, P. S. RAFT-synthesized graft copolymers that enhance pH-dependent membrane destabilization and protein circulation times. *J Control Release* 155, 167-174 (2011).
18. Sorkin, A. & Von Zastrow, M. Signal transduction and endocytosis: close encounters of many kinds. *Nat Rev Mol Cell Biol* 3, 600-614 (2002).
19. Evans, B. C. et al. Ex vivo red blood cell hemolysis assay for the evaluation of pH-responsive endosomolytic agents for cytosolic delivery of biomacromolecular drugs. *J Vis Exp*, e50166 (2013).
20. Humphries, W. H. t. & Payne, C. K. Imaging lysosomal enzyme activity in live cells using self-quenched substrates. *Anal Biochem* 424, 178-183 (2012).
21. Rousseau, S. et al Inhibition of SAPK2a/p38 prevents hnRNP A0 phosphorylation by MAPKAP-K2 and its interaction with cytokine mRNAs. *EMBO J* 21, 6505-6514 (2002).
22. Hitti, E. et al. Mitogen-activated protein kinase-activated protein kinase 2 regulates tumor necrosis factor mRNA stability and translation mainly by altering tristetraprolin expression, stability, and binding to adenine/uridine-rich element. *Mol Cell Biol* 26, 2399-2407 (2006).
23. Ronkina, N. et al. MAPKAP kinases MK2 and MK3 in inflammation: complex regulation of TNF biosynthesis via expression and phosphorylation of tristetraprolin. *Biochem Pharmacol* 80, 1915-1920 (2010).
24. Chen, H. F., Xie, L. D. & Xu, C. S. Role of heat shock protein 27 phosphorylation in migration of vascular smooth muscle cells. *Mol Cell Biochem* 327, 1-6 (2009).
25. Schleimer, K. et al. Training a sophisticated microsurgical technique: interposition of external jugular vein graft in the common carotid artery in rats. *J Vis Exp* (2012).
26. Mueller, L. et al. TNF-alpha similarly induces IL-6 and MCP-1 in fibroblasts from colorectal liver metastases and normal liver fibroblasts. *Biochem Biophys Res Commun* 397, 586-591 (2010).
27. Mitchell, R. N. & Libby, P. Vascular remodeling in transplant vasculopathy. *Circ Res* 100, 967-978 (2007).
28. Stark, V. K., Hoch, J. R., Warner, T. F. & Hullett, D. A. Monocyte chemotactic protein-1 expression is associated with the development of vein graft intimal hyperplasia. *Arterioscl Throm Vas* 17, 1614-1621 (1997).
29. Walensky, L. D. et al. Activation of apoptosis in vivo by a hydrocarbon-stapled BH3 helix. *Science* 305, 1466-1470 (2004).
30. Heitz, F., Morris, M. C. & Divita, G. Twenty years of cell-penetrating peptides: from molecular mechanisms to therapeutics. *British Journal of Pharmacology* 157, 195-206 (2009).
31. LaBelle, J. L. et al. A stapled BIM peptide overcomes apoptotic resistance in hematologic cancers. *J Clin Invest* 122, 2018-2031 (2012).
32. Walensky, L. D. et al. A stapled BID BH3 helix directly binds and activates BAX. *Mol Cell* 24, 199-210 (2006).
33. Okamoto, T. et al. Stabilizing the pro-apoptotic BimBH3 helix (BimSAHB) does not necessarily enhance affinity or biological activity. *ACS Chem Biol* 8, 297-302 (2013).
34. Mislick, K. A. & Baldeschwieler, J. D. Evidence for the role of proteoglycans in cation-mediated gene transfer. *Proc Natl Acad Sci U S A* 93, 12349-12354 (1996).
35. Richard, J. P. et al. Cellular uptake of unconjugated TAT peptide involves clathrin-dependent endocytosis and heparan sulfate receptors. *J Biol Chem* 280, 15300-15306 (2005).
36. Mietus-Snyder, M., Friera, A., Glass, C. K. & Pitas, R. E. Regulation of scavenger receptor expression in smooth muscle cells by protein kinase C: a role for oxidative stress. *Arterioscler Thromb Vasc Biol* 17, 969-978 (1997).
37. Li, H., Freeman, M. W. & Libby, P. Regulation of smooth muscle cell scavenger receptor expression in vivo by atherogenic diets and in vitro by cytokines *J Clin Invest* 95, 122-133 (1995).
38. Voigt, J., Christensen, J. & Shastri, V. P. Differential uptake of nanoparticles by endothelial cells through polyelectrolytes with affinity for caveolae. *Proc Natl Acad Sci U S A* 111, 2942-2947 (2014).
39. Alam, M. R. et al. The biological effect of an antisense oligonucleotide depends on its route of endocytosis and trafficking. *Oligonucleotides* 20, 103-109 (2010).
40. Meier, O. et al. Adenovirus triggers macropinocytosis and endosomal leakage together with its clathrin-mediated uptake. *J Cell Biol* 158, 1119-1131 (2002).
41. Rossman, J. S., Leser, G. P. & Lamb, R. A. Filamentous influenza virus enters cells via macropinocytosis. *J Virol* 86, 10950-10960 (2012).
42. Hewlett, L. J., Prescott, A. R. & Watts, C. The coated pit and macropinocytic pathways serve distinct endosome populations. *J Cell Biol* 124, 689-703 (1994).
43. Wadia, J. S., Stan, R. V. & Dowdy, S. F. Transducible TAT-HA fusogenic peptide enhances escape of TAT-fusion proteins after lipid raft macropinocytosis. *Nat Med* 10, 310-315 (2004).
44. Muto, A. et al Inhibition of Mitogen Activated Protein Kinase Activated Protein Kinase II with MMI-0100 reduces intimal hyperplasia ex vivo and in vivo. *Vascul Pharmacol* 56, 47-55 (2012).
45. Kalra, M. & Miller, V. M. Early remodeling of saphenous vein grafts: proliferation, migration and apoptosis of adventitial and medial cells occur simultaneously with changes in graft diameter and blood flow. *J Vasc Res* 37, 576-584 (2000).
46. Zwolak, R. M., Adams, M. C. & Clowes, A. W. Kinetics of vein graft hyperplasia: association with tangential stress. *J Vasc Surg* 5, 126-136 (1987).
47. Alexander, J. H. et al. The PRoject of Ex-vivo Vein graft ENgineering via Transfection IV (PREVENT IV) trial: study rationale, design, and baseline patient characteristics. *Am Heart J* 150, 643-649 (2005).
48. Goldberg, M., Langer, R. & Jia, X. Nanostructured materials for applications in drug delivery and tissue engineering. *J Biomater Sci Polym Ed* 18, 241-268 (2007).
49. Li, H., Nelson, C. E., Evans, B. C. & Duvall, C. L. Delivery of intracellular-acting biologics in pro-apoptotic therapies. *Curr Pharm Des* 17, 293-319 (2011).
50. Ferrito, M. a. T., D. A. Poly(2-ethylacrylic acid). *Macromolecular Syntheses* 11, 59-62 (1992).
51. Convertine, A. J., Benoit, D. S., Duvall, C. L., Hoffman, A. S. & Stayton, P. S. Development of a novel endosomolytic diblock copolymer for siRNA delivery. *J Control Release* 133, 221-229 (2009).
52. Henry, S. M., El-Sayed, M. E., Pirie, C. M., Hoffman, A. S. & Stayton, P. S. pH-responsive poly(styrene-alt-maleic anhydride) alkylamide copolymers for intracellular drug delivery. *Biomacromolecules* 7, 2407-2414 (2006).
53. Bolte, S. & Cordelieres, F. P. A guided tour into subcellular colocalization analysis in light microscopy. *J Microsc-Oxford* 224, 213-232 (2006).
54. Jiang, Z. et al. A novel vein graft model: adaptation to differential flow environments. *Am J Physiol Heart Circ Physiol* 286, H240-245 (2004).
55. Duvall et al. *Mol Pharm.* 2010; 7(2):468-476.

Incorporation by Reference

All publications, patents, and patent applications mentioned in this description are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A composition comprising:
   A cationic peptide electrostatically bound to an anionic pH-responsive polymer comprising a poly(($C_1$-$C_6$)alkyl-acrylic acid) at a pH of between about 6.0 and about 8.0;
   wherein the ($C_1$-$C_6$)alkyl group and the carboxylic acid group of the poly(($C_1$-$C_6$)alkyl-acrylic acid) are attached to the same carbon;
   wherein the anionic pH-responsive polymer has a pKa of between 5.0 and about 7.4;
   wherein the pH is above the pKa of the anionic pH-responsive polymer;
   wherein the peptide is one or more sequences selected from SEQ. ID. NOS: 1-4; and
   wherein the cationic active agent and the anionic pH-responsive polymer at least partially disassemble at a pH below about the pKa of the pH-responsive polymer.

2. The composition of claim 1, wherein the cationic peptide electrostatically bound to the anionic pH-responsive polymer form a polyplex having a size of about 50 nm to about 500 nm.

3. A vascular graft, wherein the vascular graft comprises the composition of claim 1.

4. A method of treating a vascular condition, comprising:
   administering an effective amount of the composition of claim 1 to a subject in need thereof.

5. The method of claim 4, wherein the vascular condition is intimal hyperplasia.

6. The method of claim 4, wherein the step of administering comprises implanting a vascular graft that includes the composition of claim 1 in a subject in need thereof.

* * * * *

SEQUENCE LISTING

```
<160> NUMBER OF SEQ ID NOS: 4

<210> SEQ ID NO 1
<211> LENGTH: 22
<212> TYPE: PRT
<213> ORGANISM: Artificial Sequence
<220> FEATURE:
<223> OTHER INFORMATION: MK2i Sequence

<400> SEQUENCE: 1

Tyr Ala Arg Ala Ala Ala Arg Gln Ala Arg Ala Lys Ala Leu Ala Arg
1               5                   10                  15

Gln Leu Gly Val Ala Ala
            20

<210> SEQ ID NO 2
<211> LENGTH: 24
<212> TYPE: PRT
<213> ORGANISM: Artificial Sequence
<220> FEATURE:
<223> OTHER INFORMATION: AZX-100 Sequence

<400> SEQUENCE: 2

Tyr Ala Arg Ala Ala Ala Arg Gln Ala Arg Ala Trp Leu Arg Arg Ala
1               5                   10                  15

Ser Ala Pro Leu Pro Gly Leu Lys
            20

<210> SEQ ID NO 3
<211> LENGTH: 22
<212> TYPE: PRT
<213> ORGANISM: Artificial Sequence
<220> FEATURE:
<223> OTHER INFORMATION: RN22 Sequence

<400> SEQUENCE: 3

Arg Arg Arg Lys Phe Val Arg Ser Arg Arg Pro Arg Thr Ala Ser Cys
1               5                   10                  15

Ala Leu Ala Phe Val Asn
            20

<210> SEQ ID NO 4
<211> LENGTH: 35
<212> TYPE: PRT
<213> ORGANISM: Artificial Sequence
<220> FEATURE:
<223> OTHER INFORMATION: Penetratin-Bak-BH3 Sequence

<400> SEQUENCE: 4

Arg Gln Ile Lys Ile Trp Phe Gln Asn Arg Arg Met Lys Trp Lys Lys
1               5                   10                  15
```

-continued

```
Met Gly Gln Val Gly Arg Gln Leu Ala Ile Ile Gly Asp Asp Ile Asn
            20                  25                  30
Arg Arg Tyr
        35
```

UNITED STATES PATENT AND TRADEMARK OFFICE
CERTIFICATE OF CORRECTION

PATENT NO. : 10,835,549 B2
APPLICATION NO. : 14/784017
DATED : November 17, 2020
INVENTOR(S) : Duvall et al.

Page 1 of 1

It is certified that error appears in the above-identified patent and that said Letters Patent is hereby corrected as shown below:

In the Specification

Insert as the second paragraph, which appears on Column 1, the following:
--Government Support
This invention was made with government support under grant number HL110056 awarded by the National Institutes of Health. The government has certain rights in the invention.--

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*